(12) United States Patent
Itabashi et al.

(10) Patent No.: US 11,114,693 B2
(45) Date of Patent: Sep. 7, 2021

(54) ELECTROLYTIC SOLUTION FOR NONAQUEOUS ELECTROLYTIC SOLUTION SECONDARY BATTERIES AND NONAQUEOUS ELECTROLYTIC SOLUTION SECONDARY BATTERY

(71) Applicant: Central Glass Company, Ltd., Ube (JP)

(72) Inventors: Saori Itabashi, Kawagoe (JP); Wataru Kawabata, Ube (JP); Katsutoshi Suzuki, Kawagoe (JP); Kazunari Takeda, Tokyo (JP)

(73) Assignee: Central Glass Company, Ltd., Ube (JP)

( * ) Notice: Subject to any disclaimer, the term of this patent is extended or adjusted under 35 U.S.C. 154(b) by 794 days.

(21) Appl. No.: 15/751,760

(22) PCT Filed: Jun. 27, 2016

(86) PCT No.: PCT/JP2016/069049
§ 371 (c)(1),
(2) Date: Feb. 9, 2018

(87) PCT Pub. No.: WO2017/026181
PCT Pub. Date: Feb. 16, 2017

(65) Prior Publication Data
US 2020/0212485 A1   Jul. 2, 2020

(30) Foreign Application Priority Data
Aug. 12, 2015 (JP) .............................. JP2015-159321

(51) Int. Cl.
*H01M 10/0567* (2010.01)
*H01M 10/0569* (2010.01)
(Continued)

(52) U.S. Cl.
CPC ...... *H01M 10/0567* (2013.01); *C07D 327/00* (2013.01); *C07D 327/10* (2013.01);
(Continued)

(58) Field of Classification Search
CPC ......... H01M 10/0567; H01M 10/0569; H01M 2300/0025; C07D 327/00
See application file for complete search history.

(56) References Cited

U.S. PATENT DOCUMENTS 5,626,981 A   5/1997 Simon et al.
6,033,809 A   3/2000 Hamamoto et al.
(Continued)

FOREIGN PATENT DOCUMENTS

CN   103378371 A   10/2013
CN   107210484 A   9/2017
(Continued)

OTHER PUBLICATIONS

European Search Report issued in counterpart European Application No. 16834878.7 dated Apr. 20, 2018 (seven (7) pages).
(Continued)

*Primary Examiner* — Osei K Amponsah
(74) *Attorney, Agent, or Firm* — Crowell & Moring LLP

(57) ABSTRACT

A nonaqueous electrolytic solution contains a nonaqueous solvent and an electrolyte dissolved in the solvent. The solution includes a difluoro ionic complex (1-Cis) in a cis conformation represented by the formula (1-Cis), and at least one of cyclic sulfonic acid ester, cyclic sulfonic acid ester having an unsaturated bond, cyclic sulfuric acid ester, cyclic disulfonic acid ester, chain disulfonic acid ester, cyclic disulfonic acid anhydride, nitrile group-containing compound, silyl phosphate ester derivative, and silyl borate ester derivative.

(Continued)

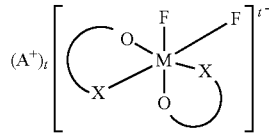

(1-Cis)

16 Claims, 1 Drawing Sheet

(51) Int. Cl.
  C07D 327/00 (2006.01)
  C07D 327/10 (2006.01)
  H01M 10/0525 (2010.01)
(52) U.S. Cl.
  CPC ... *H01M 10/0525* (2013.01); *H01M 10/0569* (2013.01); *H01M 2300/0025* (2013.01)

(56) References Cited

U.S. PATENT DOCUMENTS

| | | | |
|---|---|---|---|
| 6,506,516 | B1 | 1/2003 | Wietelmann et al. |
| 6,693,212 | B1 | 2/2004 | Wietelmann et al. |
| 6,783,896 | B2 | 8/2004 | Tsujioka et al. |
| 6,849,752 | B2 | 2/2005 | Tsujioka et al. |
| 6,919,145 | B1 | 7/2005 | Kotato et al. |
| 7,135,252 | B2 | 11/2006 | Thackeray et al. |
| 7,163,768 | B2 | 1/2007 | Utsugi et al. |
| 7,416,813 | B2 | 8/2008 | Fujihara et al. |
| 8,691,446 | B2 | 4/2014 | Sakata et al. |
| 8,822,084 | B2 | 9/2014 | Tsujioka et al. |
| 9,083,059 | B2 | 7/2015 | Hayakawa et al. |
| 9,209,479 | B2 | 12/2015 | Hiwara et al. |
| 9,227,950 | B2 | 1/2016 | Mio et al. |
| 9,419,305 | B2 | 8/2016 | Choi et al. |
| 2002/0081496 | A1 | 6/2002 | Tsujioka et al. |
| 2003/0100761 | A1 | 5/2003 | Tsujioka et al. |
| 2004/0013946 | A1 | 1/2004 | Abe et al. |
| 2004/0043300 | A1 | 3/2004 | Utsugi et al. |
| 2005/0191553 | A1 | 9/2005 | Fujihara et al. |
| 2005/0208378 | A1 | 9/2005 | Mizutani et al. |
| 2007/0009798 | A1 | 1/2007 | Inagaki et al. |
| 2008/0090154 | A1 | 4/2008 | Ihara et al. |
| 2008/0102369 | A1 | 5/2008 | Sakata et al. |
| 2009/0226808 | A1 | 9/2009 | Hiwara et al. |
| 2011/0183129 | A1 | 7/2011 | Mitsui et al. |
| 2012/0009486 | A1 | 1/2012 | Hayakawa et al. |
| 2013/0022880 | A1* | 1/2013 | Tsujioka ........... H01M 10/0567 429/345 |
| 2013/0171514 | A1 | 7/2013 | Mio et al. |
| 2013/0288139 | A1 | 10/2013 | Choi et al. |
| 2013/0330626 | A1 | 12/2013 | Kajiyama et al. |
| 2014/0193706 | A1 | 7/2014 | Morinaka et al. |
| 2015/0118579 | A1 | 4/2015 | Kondo et al. |
| 2015/0147643 | A1 | 5/2015 | Morinaka et al. |
| 2015/0194671 | A1 | 7/2015 | Nakahara et al. |
| 2015/0207142 | A1 | 7/2015 | Takijiri et al. |
| 2015/0229002 | A1 | 8/2015 | Kawasoe et al. |
| 2016/0211551 | A1 | 7/2016 | Miyasato et al. |
| 2018/0062204 | A1 | 3/2018 | Takahashi et al. |
| 2018/0241082 | A1 | 8/2018 | Suzuki et al. |

FOREIGN PATENT DOCUMENTS

| | | |
|---|---|---|
| CN | 107210485 A | 9/2017 |
| EP | 3 246 982 A1 | 11/2017 |
| EP | 3 246 983 A1 | 11/2017 |
| JP | 5-74486 A | 3/1993 |
| JP | 8-45545 A | 2/1996 |
| JP | 2000-3724 | 1/2000 |
| JP | 2001-6729 A | 1/2001 |
| JP | 2002-110235 A | 4/2002 |
| JP | 2002-151077 A | 5/2002 |
| JP | 2002-519352 A | 7/2002 |
| JP | 2002-329528 A | 11/2002 |
| JP | 2002-373703 A | 12/2002 |
| JP | 2003-505464 A | 2/2003 |
| JP | 2003-137890 A | 5/2003 |
| JP | 2004-179146 A | 6/2004 |
| JP | 2004-185931 A | 7/2004 |
| JP | 2004-281368 A | 10/2004 |
| JP | 2005-5115 A | 1/2005 |
| JP | 2006-196250 A | 7/2006 |
| JP | 2007-18883 A | 1/2007 |
| JP | 2007-179883 A | 7/2007 |
| JP | 2007-335143 A | 12/2007 |
| JP | 2008-16424 A | 1/2008 |
| JP | 2008-108586 A | 5/2008 |
| JP | 2008-270201 A | 11/2008 |
| JP | 2009-70827 A | 4/2009 |
| JP | 2009-137834 A | 6/2009 |
| JP | 2009-176752 A | 8/2009 |
| JP | 2010-219011 A | 9/2010 |
| JP | 2011-222193 A | 11/2011 |
| JP | 2013-30284 A | 2/2013 |
| JP | 2013-232417 A | 11/2013 |
| WO | WO 2004/042851 A2 | 5/2004 |
| WO | WO 2004/100293 A1 | 11/2004 |
| WO | WO 2007/043624 A1 | 4/2007 |
| WO | WO 2007/083155 A1 | 7/2007 |
| WO | WO 2010/110159 A1 | 9/2010 |
| WO | WO 2011/125397 A1 | 10/2011 |
| WO | WO 2012/053644 A1 | 4/2012 |
| WO | WO 2013/118661 A1 | 8/2013 |
| WO | WO 2013/180174 A1 | 12/2013 |
| WO | WO 2013/180175 A1 | 12/2013 |
| WO | WO 2014/034043 A1 | 3/2014 |
| WO | WO 2014/038174 A1 | 3/2014 |
| WO | WO 2015/045989 A1 | 4/2015 |
| WO | WO 2016/117279 A1 | 7/2016 |
| WO | WO 2016/117280 A1 | 7/2016 |

OTHER PUBLICATIONS

Chinese-language Office Action issued in counterpart Chinese Application No. 201680045555.5 dated Oct. 25, 2019 (14 pages).
Dean et al., "Spectroscopic Studies of Inorganic Fluoro-complexes, Part III Fluorine-19 Nuclear Magnetic Resonance Studies of Silicon(iv), Germanium(iv), and Titanium(iv) Fluoro-complexes," J. Chem. Soc. (A), 1970, vol. 15, pp. 2569-2574.
International Search Report (PCT/ISA/210) issued in PCT Application No. PCT/JP2016/069049 dated Sep. 13, 2016 with English-language translation (five (5) pages).
Japanese-language Written Opinion (PCT/ISA/237) issued in PCT Application No. PCT/JP2016/069049 dated Sep. 13, 2016 (six (6) pages).
Edited by The Comittee of Battery Technology, The Electrochemical Society of Japan, "Denchi Handbook", 1st edition, 1st print, Ohmsha, Ltd., Feb. 10, 2010, pp. 533 to 546.

* cited by examiner

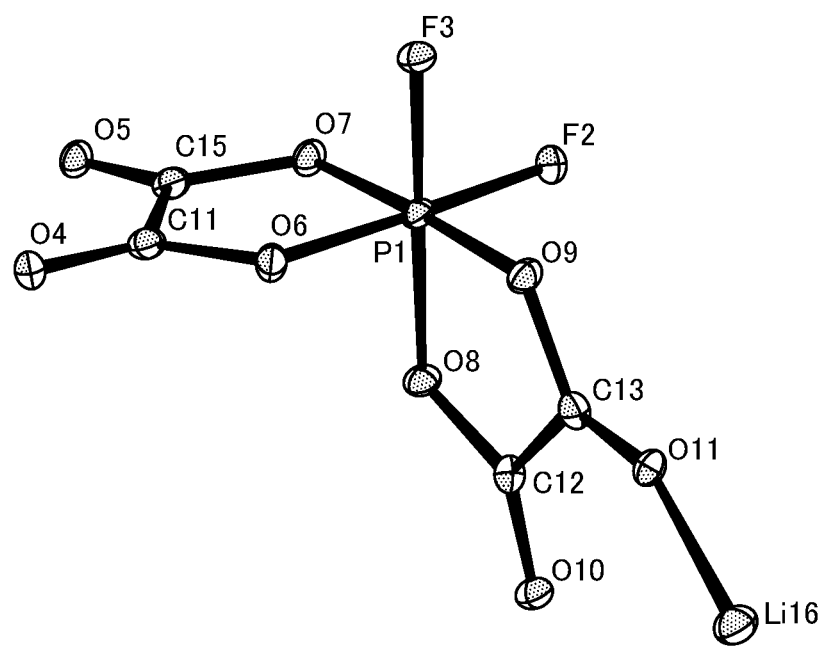

ELECTROLYTIC SOLUTION FOR NONAQUEOUS ELECTROLYTIC SOLUTION SECONDARY BATTERIES AND NONAQUEOUS ELECTROLYTIC SOLUTION SECONDARY BATTERY

TECHNICAL FIELD

The present invention relates to a nonaqueous electrolytic solution having excellent output characteristics at low temperature, and a battery such as a lithium secondary battery using the nonaqueous electrolytic solution. Further, the present invention relates to an additive useful for the nonaqueous electrolytic solution.

BACKGROUND ART

In recent years, there have been rapidly increasing demands for not only electricity storage systems for small-sized and high energy density applications, for example, information-related apparatus, communication apparatus, i.e., personal computers, video cameras, digital cameras, portable telephones, and smartphones; but also batteries with large capacity, high output and high energy density which can be used for electric vehicles, hybrid vehicles, and auxiliary power systems of fuel-cell vehicles. Moreover, there have been increasing demands for batteries which can be used for a long time even in electricity storage systems for large-sized and high power applications, for example, electric power storages. As one of the candidates for such electricity storage systems, nonaqueous electrolytic solution batteries have been under active development, such as lithium ion batteries, lithium batteries, and lithium ion capacitors.

Lithium secondary batteries mainly include a positive electrode, a nonaqueous electrolytic solution, and a negative electrode. As negative electrodes for lithium secondary batteries, known are, for example, metal lithium, metal compounds (for example, elemental metals, oxides, alloys with lithium, and the like) capable of occluding and releasing lithium, carbon materials, and the like. In particular, lithium secondary batteries where carbon materials capable of occluding and releasing lithium such as corks, artificial graphite, natural graphite, and the like are used have been put into wide practical use. For example, it is reported that in a lithium secondary battery where a highly crystallized carbon material such as natural graphite and artificial graphite is used as a negative electrode material, a nonaqueous solvent in a nonaqueous electrolytic solution may be reductively decomposed on the surface of a negative electrode upon charging, resulting in generation of decomposition products or gases. This may interfere with the desired electrochemical reactions of the battery, which in turn, may decrease cycle characteristics.

A negative electrode may react with lithium cations or a solvent of an electrolytic solution when lithium cations are intercalated into the negative electrode upon charging at the first cycle. This may form a film containing lithium oxide, lithium carbonate, and lithium alkylcarbonate as the main components on the surface of the negative electrode. This film on the surface of the electrode which is called a Solid Electrolyte Interface (SEI) may, in nature, have significant impacts on battery performance. For example, it may reduce reductive decomposition of a solvent to prevent deterioration of battery performance.

As described above, one of the disadvantages is that lithium may not be smoothly occluded into and released from a negative electrode due to adverse effects such as accumulation of decomposition products and generation of gases from a nonaqueous solvent, and pulverization of a negative electrode material, resulting in significant deterioration of battery characteristics such as cycle characteristics.

Meanwhile, as a positive electrode, known are, for example, $LiCoO_2$, $LiMn_2O_4$, $LiNiO_2$, $LiFePO_4$, and the like. It is reported that in lithium secondary batteries where these materials are used, a nonaqueous solvent in a nonaqueous electrolytic solution may partly undergo local oxidative decomposition at the interface between a positive electrode material and the nonaqueous electrolytic solution when the temperature is increased during charging. This results in generation of decomposition products and gases. As a result, the desired electrochemical reaction of the battery may be interfered with, which in turn, may decrease battery performances such as cycle characteristics. As in the negative electrode, a film may also be formed on the surface of the positive electrode due to oxidatively decomposed products. This film is also known to play an important role. For example, oxidative decomposition of a solvent may be prevented, and the battery gas yield may be reduced.

As described above, conventional lithium secondary batteries have a problem in that decomposition products and gases generated when a nonaqueous electrolytic solution decomposes on a positive electrode and a negative electrode may interfere with the movement of lithium ions, and may cause the expansion of a battery. These may be responsible for decreased battery performance.

In order to overcome the above problems and further improve battery performance such as long term durability and output characteristics, it is important to form an SEI having a high ion conductivity, a low electron conductivity, and a long-term stability. To this end, attempts have been widely made for intentionally forming a good SEI by adding a small amount (usually 0.01 mass % or more and 10 mass % or less) of a compound called an additive to an electrolytic solution.

For example, Patent Document 1 describes that a nonaqueous electrolytic solution including a cyclic compound having a disulfonic acid anhydride group (—S(=O)$_2$—O—S(=O)$_2$—) and succinonitrile can improve cycle characteristics. Moreover, this Patent Document describes that further inclusion of bis(oxalato)lithium borate and bis(trifluoromethanesulfonyl)imidelithium (LiTFSI) can provide further improvement in properties.

A nonaqueous electrolytic solution is disclosed containing a phosphorus-boron complex and the like as an additive for forming an effective SEI, such as a lithium difluoro(oxalato) borate (Patent Document 2).

Patent Document 3 discloses an electrolytic solution including both a difluoro(bisoxalato) phosphate salt and a tetrafluoro(oxalato) phosphate salt, which can improve a low-temperature property (the discharge capacity ratio of −20° C./25° C.) at 0° C. or below as well as cycle characteristics and high-temperature storage properties.

Patent Document 4 describes that a nonaqueous electrolytic solution including a lithium phosphate compound including difluoro(bisoxalato)lithium phosphate and tetrafluoro(oxalato)lithium phosphate in an amount of more than 0 and 4.0 mass % or less relative to the total weight of the nonaqueous electrolytic solution and a cyclic sulfone compound (unsaturated sultone compound and others) in an amount of more than 0 mass % and 3.0 mass % or less relative to the total weight of the nonaqueous electrolytic solution can suppress gas generation during the initial charge and discharge of a battery and gas generation even when a battery is used for a long period of time under a high-temperature environment.

It is noted that Patent Document 5 discloses a method of manufacturing a phosphorus-boron complex such as lithium difluorooxalatoborate used as an electrolyte for electrochemical devices. Further, Patent Document 6 discloses a method of manufacturing lithium tris(oxalato)phosphate.

Nonpatent Document 1 discloses a method of manufacturing a fluoro complex having silicon or the like in the complex center.

Patent Document 1: PCT International Publication No. WO2010/110159
Patent Document 2: Japanese Unexamined Patent Application, Publication No. 2002-110235
Patent Document 3: Japanese Unexamined Patent Application, Publication No. 2011-222193
Patent Document 4: PCT International Publication No. WO2014/038174
Patent Document 5: Japanese Unexamined Patent Application, Publication No. 2003-137890
Patent Document 6: Japanese Unexamined Patent Application (Translation of PCT Application), Publication No. 2003-505464
Non-Patent Document 1: J. Chem. Soc. (A), 1970, 15, 2569-2574

DISCLOSURE OF THE INVENTION

Problems to be Solved by the Invention

Nonetheless, the nonaqueous electrolytic solutions described above are considered as insufficient in terms of low-temperature properties and high-temperature storage properties, and do not satisfy recent demands for high-performance batteries. Therefore, further improvements have been desired. That is, although not a small number of practical nonaqueous electrolytic solution batteries, which are typically lithium ion batteries, are already available, an electrolytic solution having sufficient properties has not yet been obtained for applications where batteries may potentially be used under more harsh environments, including in-vehicle batteries.

Specifically, high output characteristics at a low temperature are strongly desired to allow a nonaqueous electrolytic solution battery to operate at a high output without aid of thermal insulation and heating even in cold climate areas. In order to achieve this, various electrolytic solutions have been proposed to date. However, the majority of them remain unsatisfactory in that the output characteristics are significantly decreased after batteries are used to some extent (charge-discharge cycles have been performed for certain times; or storage history at a high temperature is long) although the initial output characteristics are improved. Therefore, an electrolytic solution is strongly desired which shows high output characteristics at low temperature even after a certain number of charge-discharge cycles or after stored at high temperature. Moreover, good high-rate properties are required even after a certain number of charge-discharge cycles have been performed in order to enable high-speed charging and high-power discharging.

Means for Solving the Problems

In view of the above circumstances, the present inventors conducted extensive studies about six-coordinate ionic complexes which can be present in their cis- or trans-isomers. After comparing effects of separate addition of the cis- and trans-isomer, the present inventors found that a cis isomer shows a higher effect for improving output characteristics at low temperature after cycle durability tests. Further, an object of the present invention is to provide a nonaqueous electrolytic solution and a nonaqueous electrolytic solution battery capable of showing high output characteristics at a low temperature even after the battery is used to some extent, and capable of showing large charge and discharge capacities at a high rate under ordinary temperature, and further capable of showing sufficient performance again at low temperature even after stored at a high temperature, in which a six-coordinate ionic complex in the cis configuration and a specific compound are both included. Specifically, the present invention can provide the followings.

For example, a first invention of the present embodiment is a nonaqueous electrolytic solution containing a nonaqueous solvent and an electrolyte dissolved in the nonaqueous solvent, the nonaqueous electrolytic solution comprising: (I) a difluoro ionic complex (1-Cis) in the cis conformation represented by the general formula (1-Cis), and (II) at least one compound selected from the group consisting of cyclic sulfonic acid ester, cyclic sulfonic acid ester having an unsaturated bond, cyclic sulfuric acid ester, cyclic disulfonic acid ester, chain disulfonic acid ester, cyclic disulfonic acid anhydride, nitrile group-containing compound, silyl phosphate ester derivative, and silyl borate ester derivative.

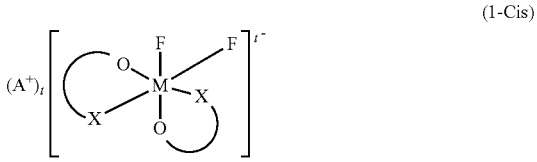

(1-Cis)

wherein in (1-Cis),

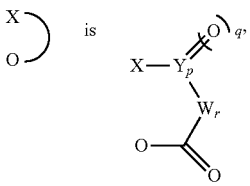

In the general formula (1-Cis), $A^+$ is any one selected from the group consisting of a metal ion, a proton, and an onium ion, and M is any one selected from the group consisting of Si, P, As, and Sb.

F is a fluorine atom, and O is an oxygen atom.

t is 2 when M is Si, and t is 1 when M is P, As, or Sb.

X is an oxygen atom or —N($R^1$)—. N is a nitrogen atom, and $R^1$ is a hydrocarbon group having 1 to 10 carbon atoms and optionally having a hetero atom and/or a halogen atom (the hydrocarbon group optionally having a branched-chain or ring structure when the number of carbon atoms is 3 or more), X and W optionally form a direct bond to form a structure represented by the following general formulae (1-Cis-1) to (1-Cis-3) when X is —N($R^1$)—, and p is 0. $R^1$ is not present in the following general formula (1-Cis-2) where the direct bond is a double bond.

Y is a carbon atom or a sulfur atom. q is 1 when Y is a carbon atom. q is 1 or 2 when Y is a sulfur atom.

W represents a hydrocarbon group having 1 to 10 carbon atoms and optionally having a hetero atom and/or a halogen atom (the hydrocarbon group optionally having a branched-chain or ring structure when the number of carbon atoms is 3 or more), or —N($R^2$)—. Here, $R^2$ represents a hydrogen atom, an alkaline metal, or a hydrocarbon group having 1 to 10 carbon atoms and optionally having a hetero atom and/or a halogen atom. $R^2$ optionally have a branched-chain or ring structure when the number of carbon atoms is 3 or more. p is 0 or 1, and q is an integer of 0 to 2, and r is an integer of 0 to 2. Further, $p+r \geq 1$.

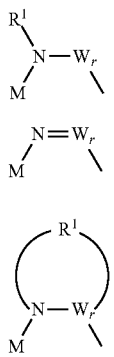

(1-Cis-1)

(1-Cis-2)

(1-Cis-3)

Effects of the Invention

The present invention can provide a nonaqueous electrolytic solution and a nonaqueous electrolytic solution battery capable of showing high output characteristics at a low temperature even after the battery is used to some extent, and capable of showing sufficient performance again at low temperature even after stored at a high temperature.

BRIEF DESCRIPTION OF THE DRAWINGS

FIG. 1 shows analysis results from single crystal X-ray structure analysis of (1a-Cis) according to Synthesis Example 1.

PREFERRED MODE FOR CARRYING OUT THE INVENTION

1. Nonaqueous Electrolytic Solution

A nonaqueous electrolytic solution according to the present invention comprises (I) a difluoro ionic complex (1-Cis) in the cis conformation represented by the general formula (1-Cis), and (II) at least one compound selected from the group consisting of cyclic sulfonic acid ester, cyclic sulfonic acid ester having an unsaturated bond, cyclic sulfuric acid ester, cyclic disulfonic acid ester, chain disulfonic acid ester, cyclic disulfonic acid anhydride, nitrile group-containing compound, silyl phosphate ester derivative, and silyl borate ester derivative:

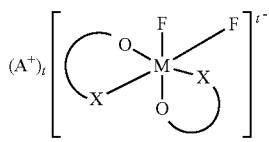

wherein in (1-Cis),

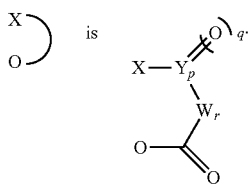

(I) Difluoro Ionic Cis Complex (1-Cis)

First, (I) difluoro ionic cis complex (1-Cis) will be described. The difluoro ionic complex represented by the following general formula (1) is a six-coordinate complex in which a bidentate ligand is coordinated to the central element M, and fluorine (hereinafter, referred to as F) is further bidentately coordinated. A complex in which a ligand is coordinated to the central element M (Si, P, As, Sb) through oxygen or nitrogen is stable, and very slowly undergoes isomerization due to exchange of ligands in the absence of a catalyst. This can allow for separation of the difluoro ionic complex (1) into two conformational isomers: a cis isomer (1-Cis) in which two fluorine atoms are attached in the same side when viewed from the central element and a trans isomer (1-Trans) in which they are attached in the opposite sides as represented by the following general formulae:

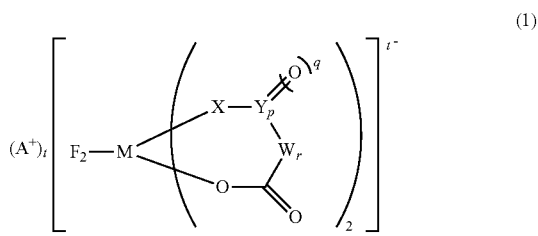

(1)

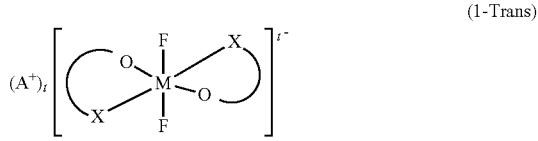

(1-Trans)

wherein in (1-Trans)

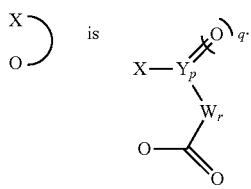

Conformational isomers can be isolated as follows, for example. A reaction liquid of the difluoro ionic complex (1) obtained after excessively promoting a reaction under a modified version of the conditions described in Patent Document 5 (Japanese Unexamined Patent Application, Publication No. 2003-137890), or a reaction liquid of the difluoro ionic complex (1) obtained by fluorinating a three-molecule coordination product synthesized in accordance with Patent Document 6 (Japanese Unexamined Patent Application (Translation of PCT Application), Publication No. 2003-505464) may be concentrated to obtain a cis/trans mixture. When the mixture are repeatedly crystallized in a mixed solvent of a carbonate ester and a chlorinated solvent (both in the filtrate and the mother liquor), (1-Cis) and (1-Trans) each with a purity of 99.9 mol % or more can be obtained separately. Further, (1-Cis) and (1-Trans) may be each obtained by selective synthesis.

(1-Cis) and (1-Trans) each preferably have a purity of 95 mol % or more, more preferably 98 mol % or more, and even more preferably 99 mol % or more.

A difluoro ionic complex to be added to the electrolytic solution for nonaqueous electrolytic solution batteries according to the present invention is not a mixture of the equal amount of cis/trans, but the percentage of (1-Cis) in the difluoro ionic complex to be included in the electrolytic solution for nonaqueous electrolytic solution batteries is preferably 95 mol % or more. That is, the mass ratio (1-Trans)/(1-Cis) of (1-Trans) to (1-Cis) is preferably 0.05 or less even when (1-Trans) is included in the electrolytic solution for nonaqueous electrolytic solution batteries.

In the general formula (1-Cis), $A^+$ is any one selected from the group consisting of a metal ion, a proton, and an onium ion, and M is any one selected from the group consisting of Si, P, As, and Sb regardless of whether the difluoro ionic complex is a cis conformer or a trans conformer, F is a fluorine atom, and O is an oxygen atom.

t is 2 when M is Si, and t is 1 when M is P, As, or Sb.

X is an oxygen atom or —N($R^1$)—. N is a nitrogen atom, and $R^1$ is a hydrocarbon group having 1 to 10 carbon atoms and optionally having a hetero atom and/or a halogen atom (the hydrocarbon group optionally has a branched-chain or ring structure when the number of carbon atoms is 3 or more).

X and W optionally form a direct bond to form a structure represented by the following general formulae (2) to (4) when X is —N($R^1$)—, and p is 0. $R^1$ is not present in the following general formula (3) where the direct bond is a double bond.

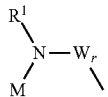
(2)

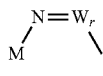
(3)

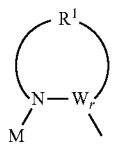
(4)

Y is a carbon atom or a sulfur atom. q is 1 when Y is a carbon atom.

q is 1 or 2, when Y is a sulfur atom.

W represents a hydrocarbon group having 1 to 10 carbon atoms and optionally having a hetero atom and/or a halogen atom (the hydrocarbon group optionally has a branched-chain or ring structure when the number of carbon atoms is 3 or more) or —N($R^2$)—. Here $R^2$ represents a hydrogen atom, an alkaline metal, or a hydrocarbon group having 1 to 10 carbon atoms and optionally having a hetero atom and/or a halogen atom. $R^2$ optionally has a branched-chain or ring structure when the number of carbon atoms is 3 or more.

p is 0 or 1, and q is an integer of 0 to 2, and r is an integer of 0 to 2. Further, p+r≥1.

No matter whether the difluoro ionic complex is a cis isomer or a trans isomer, elements in the difluoro ionic complex (1) are preferably in any of the following combinations selected from (1a) to (1d) below.

(1a) M=P; X=O; Y=C; p, q, and t=1; and r=0
(1b) M=P; X=O; W=C($CF_3$)$_2$; p and q=0; and r and t=1
(1c) M=Si; X=O; Y=C; p and q=1; t=2; and r=0
(1d) M=P; X=N($R^1$); Y=C; $R^1$=$CH_3$; p, q, and t=1; and r=0

Further, there is no particular limitation for $A^+$ as a cation of the difluoro ionic complex (1), where $A^+$ is any one selected from the group consisting of a metal ion, a proton, and an onium ion, as long as it does not impair the performance of the nonaqueous electrolytic solution and the nonaqueous electrolytic solution battery according to the present invention, but a lithium ion, a sodium ion, a potassium ion, or a quaternary alkylammonium ion is preferred in view of helping ionic conductance in a nonaqueous electrolytic solution battery. There is no particular limitation for the quaternary alkylammonium ion, but examples include trimethylpropylammonium and 1-butyl-1-methylpyrrolidinium.

For example, the difluoro ionic complexes (1a-Cis) and (1a-Trans) in which A=Li; M=P; X=O; Y=C; p, q, and t=1; and r=0 are not readily isomerized under neutral conditions. The ratio of (1a-Cis) and (1a-Trans) does not change at 40° C. after 4 hours in solutions of ethylmethyl carbonate where (1a-Cis) and (1a-Trans) are mixed in 1:9 or 5:5.

The nonaqueous electrolytic solution according to the present invention preferably contains an electrolyte, a nonaqueous solvent or a polymer mixture, and one or more ionic complexes selected from the ionic complexes in the cis-configuration represented by the general formula (1-Cis) in an amount of 0.001 mass % or more and 20.0 mass % or less relative to the nonaqueous electrolytic solution. Inclusion of (1-Cis) can significantly improve output characteristics (in particular, output characteristics at low temperature after charge and discharge are repeated). The content of (1-Cis) in the nonaqueous electrolytic solution is preferably 0.01 mass % or more and 10.0 mass % or less. More preferably, the content is 0.1 mass % or more and 3 mass % or less. A content of less than 0.001 mass % may result in an insufficient effect for improving output characteristics of a nonaqueous electrolytic solution battery at a low temperature. On the other hand, a content of more than 20 mass % may excessively increase the viscosity of an electrolytic solution to interfere with movement of cations within a nonaqueous electrolytic solution battery, resulting in decreased battery performance. It is noted that the content relative to the nonaqueous electrolytic solution as used in the present invention means a content (mass %) when the total amount of an electrolyte, (1-Cis), a compound stated in the (II), (1-Trans), (1-Tetra), the group (V), and other additives is taken as 100 mass %.

(II) Specific compounds selected from cyclic sulfonic acid ester and others

Next, (II) specific compounds selected from cyclic sulfonic acid ester and others will be described. The nonaqueous electrolytic solution according to the present invention contains (II) at least one compound selected from the group consisting of cyclic sulfonic acid ester, cyclic sulfonic acid ester having an unsaturated bond, cyclic sulfuric acid ester, cyclic disulfonic acid ester, chain disulfonic acid ester, cyclic disulfonic acid anhydride, nitrile group-containing compound, silyl phosphate ester derivative, and silyl borate ester derivative.

The total content of the compound stated in the (II) contained in the nonaqueous electrolytic solution according to the present invention is preferably 0.01 mass % or more and 10 mass % or less relative to the nonaqueous electrolytic solution. When the compound stated in the (II) is excessively contained, a passivation film may excessively be formed on the surface of a negative-electrode active material, and a film may excessively be formed even in the positive electrode side. This may result in deteriorated battery characteristics.

In a case where the compound stated in the (II) includes cyclic sulfonic acid ester, the content thereof is preferably 0.01 mass % or more and 5 mass % or less relative to the nonaqueous electrolytic solution.

In a case where the compound stated in the (II) includes cyclic sulfonic acid ester having an unsaturated bond, the content thereof is preferably 0.01 mass % or more and 3 mass % or less relative to the nonaqueous electrolytic solution, more preferably 0.1 mass % or more and 1 mass % or less.

In a case where the compound stated in the (II) includes cyclic sulfuric acid ester, the content thereof is preferably 0.01 mass % or more and 5 mass % or less relative to the nonaqueous electrolytic solution, more preferably 0.1 mass % or more and 2 mass % or less, and in particular preferably 0.5 mass % or more and 2 mass % or less.

In a case where the compound stated in the (II) includes cyclic disulfonic acid ester, the content thereof is preferably 0.01 mass % or more and 5 mass % or less relative to the nonaqueous electrolytic solution, more preferably 0.1 mass % or more and 2 mass % or less, and more preferably 0.5 mass % or more and 2 mass % or less.

In a case where the compound stated in the (II) includes chain disulfonic acid ester, the content of the chain disulfonic acid ester is preferably 0.01 mass % or more and 5 mass % or less relative to the nonaqueous electrolytic solution, more preferably 0.1 mass % or more and 2 mass % or less, and more preferably 0.5 mass % or more and 2 mass % or less.

In a case where the compound stated in the (II) includes cyclic disulfonic acid anhydride, the content thereof is preferably 0.01 mass % or more and 3 mass % or less relative to the nonaqueous electrolytic solution, more preferably 0.1 mass % or more and 2 mass % or less, and more preferably 0.5 mass % or more and 2 mass % or less.

In a case where the compound stated in the (II) includes a nitrile group-containing compound, the content thereof is preferably 0.01 mass % or more and 5 mass % or less relative to the nonaqueous electrolytic solution, more preferably 0.1 mass % or more and 2 mass % or less, and more preferably 0.5 mass % or more and 2 mass % or less.

In a case where the compound stated in the (II) includes a silyl phosphate ester derivative, the content thereof is preferably 0.01 mass % or more and 5 mass % or less relative to the nonaqueous electrolytic solution, more preferably 0.1 mass % or more and 2 mass % or less, and more preferably 0.5 mass % or more and 2 mass % or less.

In a case where the compound stated in the (II) includes a silyl borate ester derivative, the content thereof is preferably 0.01 mass % or more and 5 mass % or less relative to the nonaqueous electrolytic solution, more preferably 0.1 mass % or more and 2 mass % or less, and more preferably 0.5 mass % or more and 2 mass % or less.

Cyclic Sulfonic Acid Ester and Others

In a case where the compound stated in the (II) include cyclic sulfonic acid ester, the cyclic sulfonic acid ester is preferably represented by the following formula (II-1a). Further, in a case where the compound stated in the (II) includes cyclic sulfonic acid ester having an unsaturated bond, the cyclic sulfonic acid ester having an unsaturated bond is preferably represented by the following formula (II-1b).

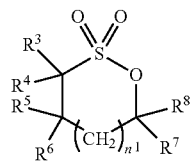

(II-1a)

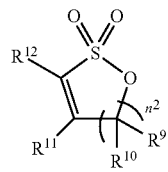

(II-1b)

(Cyclic Sulfonic Acid Ester Represented by the Formula (II-1a))

In the formula (II-1a), O represents an oxygen atom, and S represents a sulfur atom, and $n^1$ is an integer of 0 or more and 2 or less. Further, $R^3$, $R^4$, $R^5$, $R^6$, $R^7$, and $R^8$ are each independently a hydrogen atom, substituted or unsubstituted alkyl group having 1 to 6 carbon atoms, or substituted or unsubstituted fluoroalkyl group having 1 to 4 carbon atoms.

Example of the cyclic sulfonic acid ester represented by the formula (II-1a) include, for example, 1,3-propanesultone (1,3-PS), α-trifluoromethyl-γ-sultone, β-trifluoromethyl-γ-sultone, γ-trifluoromethyl-γ-sultone, α-methyl-γ-sultone, α,β-di(trifluoromethyl)-γ-sultone, α,α-di(trifluoromethyl)-γ-sultone, α-undecafluoropentyl-γ-sultone, α-heptafluoropropyl-γ-sultone, 1,4-butanesultone (1,4-BS), 1,3-pentanesultone, and the like.

Among these, 1,3-propanesultone (1,3-PS) is suitable considering that a decomposition film is thought to be formed on the negative electrode of a nonaqueous electrolytic solution battery as described in Japanese Unexamined Patent Application, Publication No. 2009-70827 and others.

Cyclic sulfonic acid esters may be used alone or in combination of two or more. When the nonaqueous electrolytic solution containing the above cyclic sulfonic acid ester is used for a battery, a film is formed on a positive electrode and a negative electrode.

For example, when charging a test nonaqueous electrolytic solution battery including a nonaqueous electrolytic solution containing the compound represented by the general formula (1-Cis) and 1,3-PS, the compound represented by the general formula (1-Cis) appears to first form a film on a negative electrode, and then 1,3-PS appears to form a film. As a result, a composite film of the compound represented by the general formula (1-Cis) and 1,3-PS appears to be formed. Moreover, a film is also formed in the positive electrode side, enabling reduced oxidative decomposition of a nonaqueous solvent in the positive electrode side under a high-temperature environment.

(Cyclic Sulfonic Acid Ester Having an Unsaturated Bond Represented by Formula (II-1b))

In the formula (II-1b), O represents an oxygen atom, and S represents a sulfur atom, and $n^2$ is an integer of 1 or more and 3 or less. Further, $R^9$, $R^{10}$, $R^{11}$, and $R^{12}$ are each independently a hydrogen atom, a substituted or unsubstituted alkyl group having 1 to 5 carbon atoms, or a substituted or unsubstituted fluoroalkyl group having 1 to 4 carbon atoms.

Examples of the cyclic sulfonic acid ester having an unsaturated bond represented by the general formula (II-1b) include, for example, 1,3-propenesultone, 1,4-butenesultone, 2,4-pentenesultone, 3,5-pentenesultone, 1-fluoro-1,3-propenesultone, 1-trifluoromethyl-1,3-propenesultone, 1,1,1-trifluoro-2,4-butenesultone, 1,4-butenesultone, 1,5-pentenesultone, and the like. Among these, 1,3-propenesultone (1,3-PRS) and 1,4-butenesultone are more preferably used in view of reactivity within a battery system.

Cyclic sulfonic acid esters having unsaturated bonds may be used alone or in combination of two or more. When the nonaqueous electrolytic solution containing the above cyclic sulfonic acid ester having an unsaturated bond is used for a battery, a film is formed on a positive electrode and a negative electrode.

For example, when charging a test nonaqueous electrolytic solution battery including a nonaqueous electrolytic solution containing the compound represented by the general formula (1-Cis) and 1,3-PRS, the compound represented by the general formula (1-Cis) appears to first form a film on a negative electrode, and then 1,3-PRS appears to form a film. As a result, a composite film of the compound represented by the general formula (1-Cis) and 1,3-PRS appears to be formed. Further, a film is also formed in the positive electrode side, enabling reduced oxidative decomposition of a nonaqueous solvent in the positive electrode side under a high-temperature environment.

Cyclic Sulfuric Acid Ester

In a case where the compound stated in the (II) includes cyclic sulfuric acid ester, the cyclic sulfuric acid ester is preferably represented by the formulae (II-2a) and/or (II-2b).

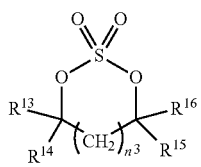

(II-2a)

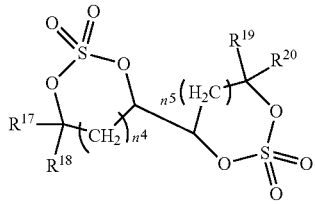

(II-2b)

In the formula (II-2a), O presents an oxygen atom, and S represents a sulfur atom, and C represents a carbon atom, and $n^3$ is an integer of 0 or more and 1 or less, and $R^{13}$, $R^{14}$, $R^{15}$, and $R^{16}$ are each independently a hydrogen atom, a substituted or unsubstituted alkyl group having 1 to 5 carbon atoms, a substituted or unsubstituted alkenyl group having 2 to 5 carbon atoms, a substituted or unsubstituted alkynyl group having 2 to 5 carbon atoms, or a substituted or unsubstituted fluoroalkyl group having 1 to 4 carbon atoms, provided that $R^{13}$ or $R^{14}$ and $R^{15}$ or $R^{16}$ may form a single bond with each other when $n^3$ is 0.

Examples of the cyclic sulfuric acid ester represented by the general formula (II-2a) include, for example, compounds represented by the formulae (II-2a-1) to (II-2a-8), and others. Among these, the compound represented by the formula (II-2a-4) is more preferred. It is preferred in view of a high property-improving effect and chemical stability. It is noted that the cyclic sulfuric acid ester represented by the general formula (II-2a) is not be limited to the compounds represented by the formulae (II-2a-1) to (II-2a-8), and other compounds may also be used.

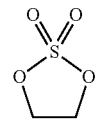

(II-2a-1)

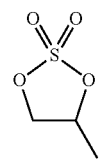

(II-2a-2)

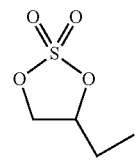

(II-2a-3)

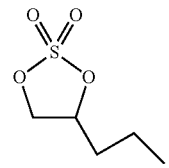

(II-2a-4)

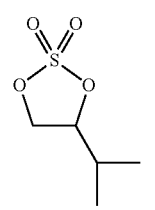

(II-2a-5)

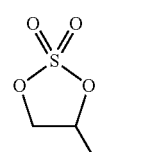

(II-2a-6)

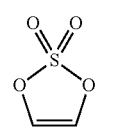

(II-2a-7)

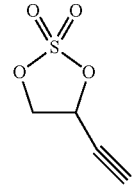

(II-2a-8)

In the formula (II-2b), O represents an oxygen atom, and S represents a sulfur atom, and C represents a carbon atom, and $n^4$ and $n^5$ are each an integer of 0 or more and 1 or less, and $R^{17}$, $R^{18}$, $R^{19}$, and $R^{20}$ are each independently a hydrogen atom, a substituted or unsubstituted alkyl group having 1 to 5 carbon atoms, or a substituted or unsubstituted fluoroalkyl group having 1 to 4 carbon atoms.

Examples of the cyclic sulfuric acid ester represented by the general formula (II-2b) include, for example, compounds represented by the formulae (II-2b-1) to (II-2b-3), and others. Among these, the compound represented by the formula (II-2b-1) is more preferred. It is noted that the cyclic sulfuric acid ester represented by the general formula (II-2b) is not be limited to the compounds represented by the formulae (II-2b-1) to (II-2b-3), and other compounds may also be used.

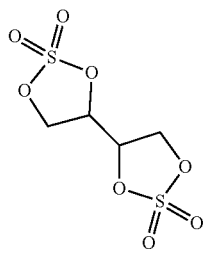
(II-2b-1)

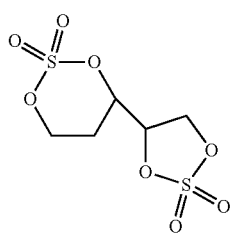
(II-2b-2)

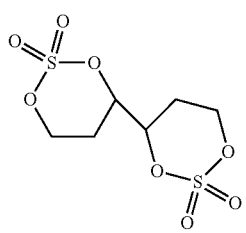
(II-2b-3)

The cyclic sulfuric acid esters represented by the general formulae (II-2a) and (II-2b) may be used alone, or in combination of two or more.

When the nonaqueous electrolytic solution containing the above cyclic sulfuric acid ester is used for a battery, a film is formed on a positive electrode and a negative electrode. For example, when charging a test nonaqueous electrolytic solution battery including a nonaqueous electrolytic solution containing the compound represented by the general formula (1-Cis) and the compound represented by the formula (II-2a-4), the compound represented by the general formula (1-Cis) appears to first form a film on a negative electrode, and then the compound represented by the formula (II-2a-4) appears to form a film. As a result, a composite film of the compound represented by the general formula (1-Cis) and the compound represented by the formula (II-2a-4) appears to be formed. Further, a film is also formed in the positive electrode side, enabling reduced oxidative decomposition of a nonaqueous solvent in the positive electrode side under a high-temperature environment.

Cyclic Disulfonic Acid Ester

In a case where the compound stated in the (II) includes cyclic disulfonic acid ester, the cyclic disulfonic acid ester is preferably represented by any one or more of the groups selected from the formulae (II-3a), (II-3b), and (II-3c).

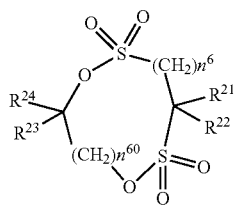
(II-3a)

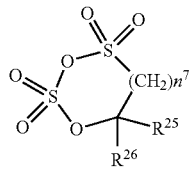
(II-3b)

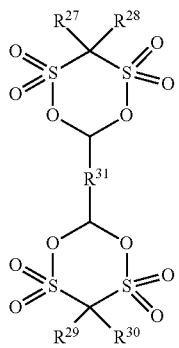
(II-3c)

In the formula (II-3a), O represents an oxygen atom, and S represents a sulfur atom, and $n^6$ is an integer of 0 or more and 4 or less, and $R^{21}$ and $R^{22}$ are each independently a hydrogen atom, a halogen atom, or a substituted or unsubstituted alkyl group having 1 to 5 carbon atoms, and $R^{23}$ and $R^{24}$ are each independently a hydrogen atom, a halogen atom, a substituted or unsubstituted alkyl group having 1 to 5 carbon atoms, or a substituted or unsubstituted fluoroalkyl group having 1 to 4 carbon atoms. $n^{60}$ is an integer of 0 or more and 4 or less.

Examples of the cyclic disulfonic acid ester represented by the general formula (II-3a) include, for example, compounds represented by the formulae (II-3a-1) to (II-3a-29), and others. Among these, the compound represented by the formula (II-3a-1), (II-3a-2), (II-3a-10), (II-3a-15), or (II-3a-16) is more preferred. It is noted that the cyclic disulfonic acid ester represented by the general formula (II-3a) is not be limited to the compounds represented by the formulae (II-3a-1) to (II-3a-29), and other compounds may also be used.

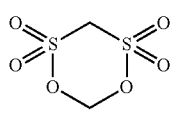
(II-3a-1)

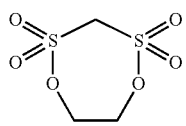
(II-3a-2)

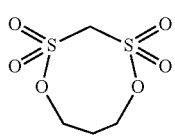 (II-3a-3)
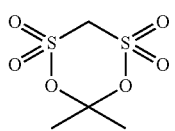 (II-3a-4)
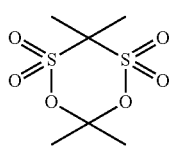 (II-3a-5)
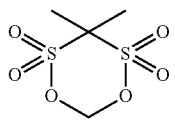 (II-3a-6)
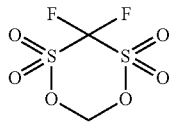 (II-3a-7)
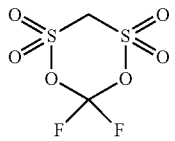 (II-3a-8)
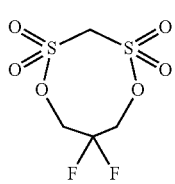 (II-3a-9)
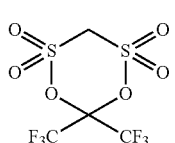 (II-3a-10)
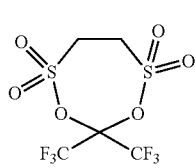 (II-3a-11)
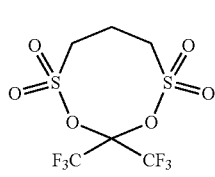 (II-3a-12)
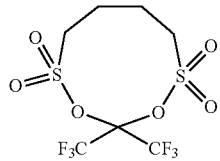 (II-3a-13)
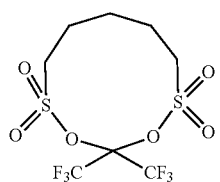 (II-3a-14)
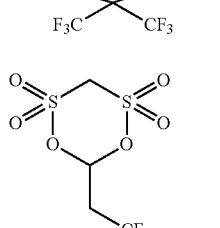 (II-3a-15)
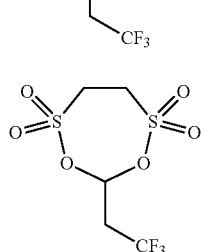 (II-3a-16)
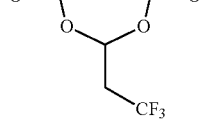 (II-3a-17)
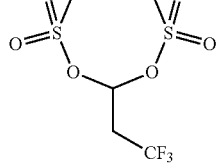 (II-3a-18)
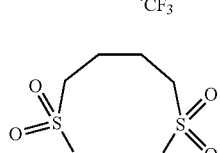 (II-3a-19)
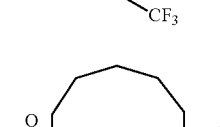 (II-3a-19)
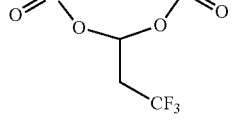 (II-3a-19)
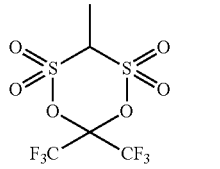 (II-3a-20)

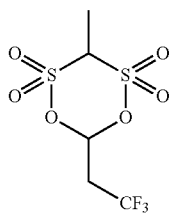
(II-3a-21)

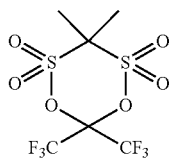
(II-3a-22)

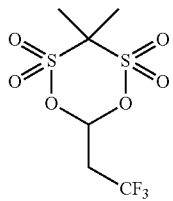
(II-3a-23)

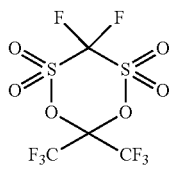
(II-3a-24)

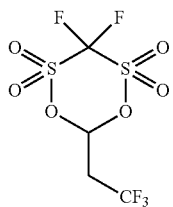
(II-3a-25)

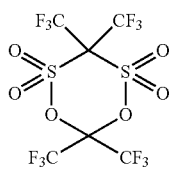
(II-3a-26)

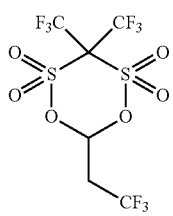
(II-3a-27)

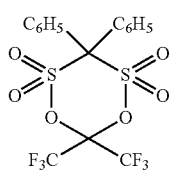
(II-3a-28)

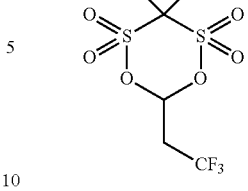
(II-3a-29)

In the formula (II-3b), O represents an oxygen atom, and S represents a sulfur atom, and $n^7$ is an integer of 0 or more and 3 or less, and $R^{25}$ and $R^{26}$ are each independently a hydrogen atom, a halogen atom, a substituted or unsubstituted alkyl group having 1 to 5 carbon atoms, or a substituted or unsubstituted fluoroalkyl group having 1 to 4 carbon atoms.

Examples of the cyclic disulfonic acid ester represented by the general formula (II-3b) include compounds represented by the formulae (II-3b-1) to (II-3b-5), and others. Among these, the compound represented by the formulae (II-3b-1), (II-3b-2), or (II-3b-5) is more preferred. It is noted that the cyclic disulfonic acid ester represented by the general formula (II-3b) is not be limited to the compounds represented by the formulae (II-3b-1) to (II-3b-5), and other compounds may also be used.

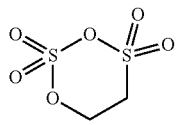
(II-3b-1)

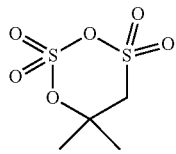
(II-3b-2)

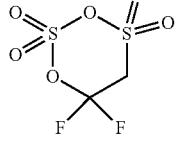
(II-3b-3)

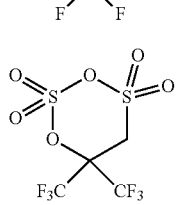
(II-3b-4)

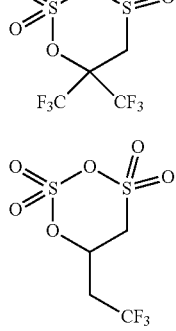
(II-3b-5)

In the formula (II-3c), O represents an oxygen atom, and S represents a sulfur atom, and $R^{27}$, $R^{28}$, $R^{29}$, and $R^{30}$ are each independently a hydrogen atom, a substituted or unsubstituted alkyl group having 1 to 5 carbon atoms, and $R^{31}$ is a substituted or unsubstituted alkyl group having 1 to 5 carbon atoms or a substituted or unsubstituted fluoroalkyl group having 1 to 4 carbon atoms.

Examples of the cyclic disulfonic acid ester represented by the general formula (II-3c) include compounds represented by the formulae (II-3c-1) to (II-3c-6), and others. Among these, the compound represented by the formula (II-3c-1) or (II-3c-2) is more preferred. It is noted that the cyclic disulfonic acid ester represented by the general formula (II-3c) is not be limited to the compounds represented by the formulae (II-3c-1) to (II-3c-6), and other compounds may also be used.

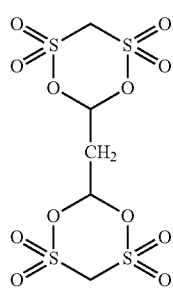
(II-3c-1)

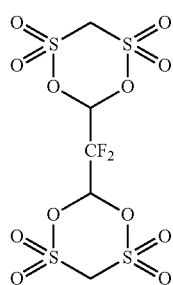
(II-3c-2)

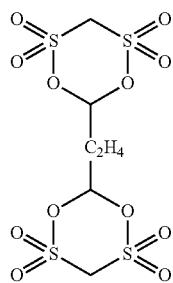
(II-3c-3)

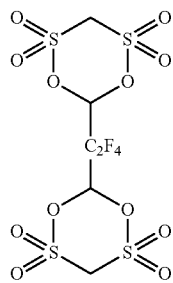
(II-3c-4)

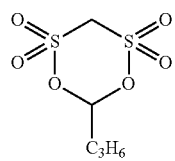
(II-3c-5)

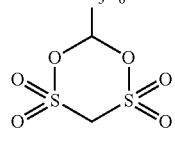

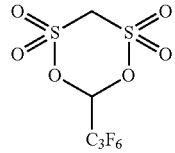
(II-3c-6)

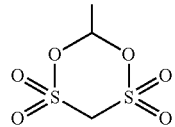

Cyclic disulfonic acid esters represented by the general formulae (II-3a), (II-3b), and (II-3c) may be used alone or in combination of two or more.

When the nonaqueous electrolytic solution containing the above cyclic disulfonic acid ester is used for a battery, a film is formed on a positive electrode and a negative electrode. For example, when charging a test nonaqueous electrolytic solution battery including a nonaqueous electrolytic solution containing the compound represented by the general formula (1-Cis) and the compound represented by the formula (II-3a-15), the compound represented by the general formula (1-Cis) appears to first form a film on a negative electrode, and then the compound represented by the formula (II-3a-15) appears to form a film. As a result, a composite film of the compound represented by the general formula (1-Cis) and the compound represented by the formula (II-3a-15) appears to be formed. Further, a film is also formed in the positive electrode side, enabling reduced oxidative decomposition of a nonaqueous solvent in the positive electrode side under a high-temperature environment.

Chain Disulfonic Acid Ester

In a case where the compound stated in the (II) includes chain disulfonic acid ester, the chain disulfonic acid ester is preferably represented by the formulae (II-4a) and/or (II-4b).

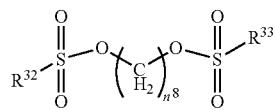
(II-4a)

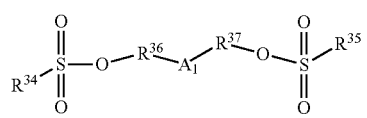
(II-4b)

In the formula (II-4a), O represents an oxygen atom, and S represents a sulfur atom, and C represents a carbon atom, and $n^8$ is an integer of 1 or more and 4 or less, and $R^{32}$ and $R^{33}$ are each independently an optionally branched alkyl group having 1 to 6 carbon atoms.

Examples of the chain disulfonic acid ester represented by the formula (II-4a) include, for example, ethyleneglycol dimethanesulfonate, 1,3-propanediol dimethanesulfonate, 1,4-butanediol dimethanesulfonate, 1,3-propanediol diethanesulfonate, 1,4-butanediol diethanesulfonate, 1,4-butanediol propanesulfonate, ethyleneglycol dibenzenesulfonate, 1,3-propanediol dibenzenesulfonate, 1,4-butanediol dibenzenesulfonate, 1,4-butanediol di-p-toluenesulfonate, and the like. Among these, 1,4-butanediol dimethanesulfonate and 1,3-propanediol dimethanesulfonate are more preferred. They are preferred in view of a high property-improving effect and readily availability.

In the formula (II-4b), O represents an oxygen atom, and S represents a sulfur atom, and $R^{34}$ and $R^{35}$ are each independently an optionally branched alkyl group having 1 to 6 carbon atoms, and $R^{36}$ and $R^{37}$ represent an unsubstituted methylene group or methylene group having an alkyl group having 1 to 4 carbon atoms, and $A_1$ is a vinylene group, or a 2-butenylene group, or an ethynylene group.

Examples of the chain disulfonic acid ester represented by the formula (II-4b) include, for example, 2-butene-1,4-diol dimethanesulfonate, 3-hexene-2,5-diol dimethanesulfonate, 2,5-dimethyl-3-hexene-2,5-diol dimethanesulfonate, 2-butene-1,4-diol diethanesulfonate, 2-butene-1,4-diol di(2-propane)sulfonate, 2-butene-1,4-diol dibutenesulfonate, 2-butene-1,4-diol methaneisopropanesulfonate, 2-butene-1,4-diol methaneethanesulfonate, 3-hexene-1,6-diol dimethanesulfonate, 3-hexene-1,6-diol diethanesulfonate, 2-butyne-1,4-diol dimethanesulfonate, 2-butyne-1,4-diol diethanesulfonate, 2-butene-1,4-diol dibutanesulfonate, and the like. Among these, 2-butene-1,4-diol dimethanesulfonate, 2-butene-1,4-diol diethanesulfonate, and 2-butyne-1,4-diol dimethanesulfonate are more preferred. They are preferred in view of a high property-improving effect and readily availability.

Cyclic Disulfonic Acid Anhydride

In a case where the compound represented by the formula (II) includes a cyclic disulfonic acid anhydride, the cyclic disulfonic acid anhydride is preferably represented by the formula (II-5a).

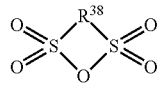

(II-5a)

In the formula (II-5a), O represents an oxygen atom, and S represents a sulfur atom, and $R^{38}$ is an alkylene group or fluorinated alkylene group having 2 to 4 carbon atoms, an alkenylene group or fluorinated alkenylene group having 2 to 4 carbon atoms, or an arylene group or fluorinated arylene group.

Examples of the cyclic disulfonic acid anhydride represented by the general formula (II-5a) include compounds represented by the formulae (II-5a-1) to (II-5a-12), and others. Geometrical isomers of these compounds are also included. Among these, the compound represented by the formula (II-5a-1) or (II-5a-2) is more preferred. It is noted that the cyclic disulfonic acid anhydride represented by the general formula (II-5a) is not limited to the compounds represented by the formulae (II-5a-1) to (II-5a-12), and other compounds may also be used.

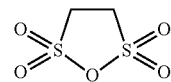

(II-5a-1)

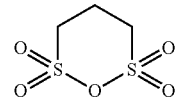

(II-5a-2)

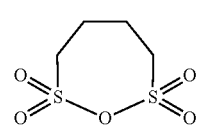

(II-5a-3)

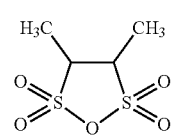

(II-5a-4)

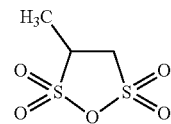

(II-5a-5)

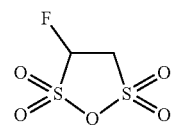

(II-5a-6)

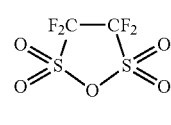

(II-5a-7)

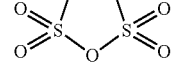

(II-5a-8)

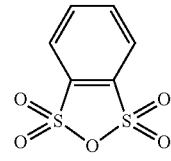

(II-5a-9)

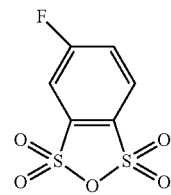

(II-5a-10)

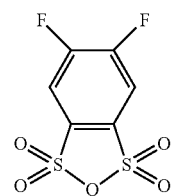

(II-5a-11)

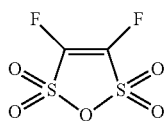
(II-5a-12)

Nitrile Group-Containing Compound

In a case where the compound stated in the (II) includes a nitrile group-containing compound, the nitrile group-containing compound is preferably represented by the formula (II-6a).

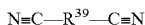
(II-6a)

In the formula (II-6a), N represents a nitrogen atom, and C represents a carbon atom, and $R^{39}$ is a compound represented by a linear or branched hydrocarbon chain having 1 to 10 carbon atoms.

Examples of the dinitrile compound represented by the general formula (II-6a) include malononitrile, succinonitrile, glutaronitrile, adiponitrile, 1,5-dicyanopentane, 1,6-dicyanohexane, 1,7-dicyanoheptane, 1,8-dicyanooctane, 1,9-dicyanononane, 1,10-dicyanodecane, 1,12-dicyanododecane, tetramethylsuccinonitrile, 2-methylglutaronitrile, 2,4-dimethylglutaronitrile, 2,2,4,4-tetramethylglutaronitrile, 1,4-dicyanopentane, 2,5-dimethyl-2,5-hexanedicarbonitrile, 2,6-dicyanoheptane, 2,7-dicyanooctane, 2,8-dicyanononane, 1,6-dicyanodecane, 1,2-dicyanobenzene, 1,3-dicyanobenzene, 1,4-dicyanobenzene, and the like.

Silyl Ester Derivative

In a case where the compound stated in the (II) includes a silyl phosphate ester derivative, the silyl phosphate ester derivative is preferably represented by the formula (II-7a). Further, in a case where the compound stated in the (II) includes a silyl borate ester derivative, the silyl borate ester derivative is preferably represented by the formula (II-7b).

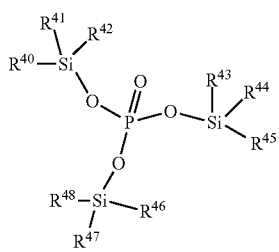
(II-7a)

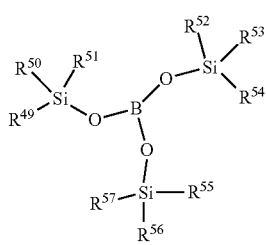
(II-7b)

In the formula (II-7a), O represents an oxygen atom, and P represents a phosphorus atom, and Si represents a silicon atom, and $R^{40}$ to $R^{48}$ are each independently a hydrogen atom, or a substituted or unsubstituted alkyl group having 1 to 5 carbon atoms.

Examples of the silyl phosphate ester derivative represented by the general formula (II-7a) include tris(trimethylsilyl) phosphate, tris(triethylsilyl) phosphate, tris(vinyldimethylsilyl) phosphate, tris(triisopropylsilyl) phosphate, tris(dimethylethylsilyl) phosphate, tris(butyldimethylsilyl) phosphate, and the like. Among these, tris(trimethylsilyl) phosphate is more preferred. It is preferred in view of a high property-improving effect and readily availability.

In the formula (II-7b), O represents an oxygen atom, and B represents a boron atom, and Si represents a silicon atom, and $R^{49}$ to $R^{57}$ are each independently a hydrogen atom, or a substituted or unsubstituted alkyl group having 1 to 5 carbon atoms.

Examples of the silyl borate ester derivative represented by the general formula (II-7b) include tris(trimethylsilyl) borate, tris(triethylsilyl) borate, tris(triisopropylsilyl) borate, tris(dimethylethylsilyl) borate, tris(butyldimethylsilyl) borate, and the like. Among these, tris(trimethylsilyl) borate is more preferred. It is preferred in view of a high property-improving effect and readily availability.

(III) Difluoro Ionic Trans Complex (1-Trans)

The difluoro ionic complex contained in the nonaqueous electrolytic solution according to the present invention may be any as long as it is not a mixture of equal amount of cis/trans, but 95 mol % or more of the difluoro ionic complex contained in the electrolytic solution for nonaqueous electrolytic solution batteries is preferably (1-Cis). That is, the mass ratio to the difluoro ionic complex (1-Cis):(1-Trans)/(1-Cis) is preferably 0.05 or less even when the difluoro ionic complex (1-Trans) as a trans isomer of the difluoro ionic complex (1-Cis) is included in the electrolytic solution for nonaqueous electrolytic solution batteries.

However, a certain amount of (1-Trans) relative to (1-Cis) is preferably included in the nonaqueous electrolytic solution according to the present invention in view of enhanced low-temperature output characteristics after storage at a high temperature.

There is no particular limitation for the mass ratio (1-Trans)/(1-Cis) of the difluoro ionic complex (1-Trans) to the difluoro ionic complex (1-Cis), but is preferably 0.0001 or more and 0.05 or less, more preferably 0.001 or more and 0.03 or less, and even more preferably 0.002 or more and 0.01 or less.

In the present specification, methods of quantifying the mass ratio (1-Trans)/(1-Cis) of (1-Trans) to (1-Cis) in an electrolytic solution include NMR analysis, liquid chromatography-mass spectrometry (LC-MS), and the like. In NMR analysis, (1-Trans) and (1-Cis) each have a peak in different positions in NMR, and thus the mass ratio can be quantified by measuring the areas of their identified peaks. In LC-MS, the peaks of (1-Trans) and (1-Cis) can be separated using a column, and thus the mass ratio can be quantified by measuring their peak areas.

(IV) Tetrafluoro Ionic Complex (1-Tetra)

Preferably, the nonaqueous electrolytic solution according to the present invention further includes a tetrafluoro ionic complex (1-Tetra) having tetradentate F atoms represented by the following general formula (1-Tetra) because increase in the internal pressure of a container during long-term storage can be controlled. However it is not an essential aspect.

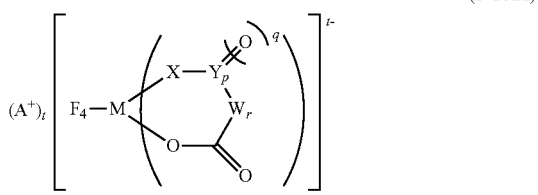

(1-Tetra)

In the general formula (1-Tetra), $A^+$ is any one selected from the group consisting of a metal ion, a proton, and an onium ion, and M is any one selected from the group consisting of Si, P, As, and Sb.

F is a fluorine atom, and O is an oxygen atom.

t is 2 when M is Si, and t is 1 when M is P, As, or Sb.

X is an oxygen atom or $-N(R^1)-$. N is a nitrogen atom, and $R^1$ is a hydrocarbon group having 1 to 10 carbon atoms and optionally having a hetero atom and/or a halogen atom (the hydrocarbon group optionally has a branched-chain or ring structure when the number of carbon atoms is 3 or more).

X and W optionally form a direct bond to take one or more structures selected from the following general formulae (1-Tetra-1) to (1-Tetra-3) when X is $-N(R^1)-$, and p is 0. $R^1$ is not present in the following general formula (1-Tetra-2) where the direct bond is a double bond.

Y is a carbon atom or a sulfur atom. q is 1 when Y is a carbon atom.

q is 1 or 2, when Y is a sulfur atom. W represents a hydrocarbon group having 1 to 10 carbon atoms and optionally having a hetero atom and/or a halogen atom (the hydrocarbon group optionally has a branched-chain or ring structure when the number of carbon atoms is 3 or more) or $-N(R^2)-$. Here $R^2$ represents a hydrogen atom, an alkaline metal, or a hydrocarbon group having 1 to 10 carbon atoms and optionally having a hetero atom and/or a halogen atom. $R^2$ optionally has a branched-chain or ring structure when the number of carbon atoms is 3 or more.

p is 0 or 1, and q is an integer of 0 to 2, and r is an integer of 0 to 2. Further, $p+r \geq 1$.

Elements in the anion moiety of the tetrafluoro ionic complex (1-Tetra) are preferably at least one of the combinations selected from (Tetra-a), (Tetra-b), (Tetra-c), and (Tetra-d).

(Tetra-a) M=P; X=O; Y=C; p, q, and t=1; and r=0
(Tetra-b) M=P; X=O; W=C(CF$_3$)$_2$; p and q=0; and r and t=1
(Tetra-c) M=Si; X=O; Y=C; p and q=1; t=2; and r=0
(Tetra-d) M=P; X=N(R$^1$); Y=C; R$^1$=CH$_3$; p, q, and t=1; and r=0

Further, there is no particular limitation for $A^+$ as a cation of the tetrafluoro ionic complex (1-Tetra), where $A^+$ is any one selected from the group consisting of a metal ion, a proton, and an onium ion, as long as it does not impair the performance of the nonaqueous electrolytic solution and the nonaqueous electrolytic solution battery according to the present invention, but a lithium ion, a sodium ion, a potassium ion, or a quaternary alkylammonium ion is preferred in view of helping ionic conductance in a nonaqueous electrolytic solution battery. There is no particular limitation for the quaternary alkylammonium ion, but examples include trimethylpropylammonium and 1-butyl-1-methylpyrrolidinium.

There is no particular limitation for the mass ratio (1-Tetra)/(1-Cis) of the tetrafluoro ionic complex (1-Tetra) to the difluoro ionic complex (1-Cis), but it is preferably 0.02 or more and 0.25 or less, more preferably 0.05 or more and 0.22 or less, and in particular preferably 0.07 or more and 0.20 or less.

In the present specification, methods of quantifying (1-Tetra)/(1-Cis) include NMR analysis, liquid chromatography-mass spectrometry (LC-MS), and the like. In NMR analysis, (1-Tetra) and (1-Cis) each have a peak in different positions in NMR, and thus the mass ratio can be quantified by measuring the areas of their identified peaks. Further, in LC-MS, the peaks of (1-Tetra) and (1-Cis) can be separated using a column, and thus the mass ratio can be quantified by measuring their peak areas.

The ionic complex preferably includes both a tetrafluoro ionic complex (5a, Synthesis Example 2 below) in which A=Li, M=P, X=O, Y=C, p, q, t=1, and r=0 and a difluoro ionic complex (1a, Synthesis Example 1) in which A=Li, M=P, X=O, Y=C, p, q, t=1, and r=0. An electrolytic solution containing both the tetrafluoro ionic complex (5a) and the difluoro ionic complex (1a) can improve cycle characteristics, high-temperature storage properties, and low-temperature properties (the discharge capacity rate of −20° C./25° C.) at 0° C. or less. It is noted that a conformational isomer does not exist for the tetrafluoro ionic complex (1-Tetra).

DISCUSSION

Although a six-coordinate ionic complex having two types of ligands (one of them is F) which can be present as its cis- or trans-isomer as shown in the difluoro ionic complex (1) has been used as described in Patent Document 2 (Japanese Unexamined Patent Application, Publication No. 2002-110235), the effects of the cis isomer alone and the trans isomer alone have not closely studied separately. In the present application, a cis isomer alone or a trans isomer alone was separately added to compare their individual effects. Results revealed that the cis isomer showed a better effect for improving output characteristics at low temperature after cycle durability tests.

When voltage is applied to a nonaqueous electrolytic solution containing a difluorophosphate complex having P as the central element selected from the difluoro ionic complexes (1), the difluorophosphate complex is reductively decomposed to generate a reduction-reaction decomposition product (intermediate) with a very short life time in the system. It may react with a functional group present on the surface of a negative electrode to form a SEI on the negative electrode. The SEI mainly includes a derivative of difluorophosphoric acid and a derivative of carbonic acid.

Reduction-reaction decomposition products from reduction reactions are likely different between the cis isomer and the trans isomer due to steric and electronic factors, resulting in different selectivity and rates for a reaction with a functional group on the surface of an electrode.

Discussion for Steric Factors

First, steric factors will be discussed with regard to the initiation of a reduction reaction between a negative electrode and difluorophosphate complexes (cis, trans). A difluorophosphate complex receives an electron from a negative electrode at a portion of a ligand other than F (for example, a carbon atom on the carbonyl group in the case of 1a) where the reduction reaction is initiated. Accordingly, the electron needs to approach the negative electrode from a side where F is not bonded to initiate the reduction reaction. The trans isomer has F atoms bonded at the upper and lower sides of the molecule. Consequently, the reduction reaction is initiated only when an electron approaches an electrode from either right or left, i. e., from a range of total 180° in the horizontal direction except for 180° in the vertical direction. In contrast, the cis isomer has F atoms only in the same side, and thus an electron can approach from a range of 200° to 250° in the opposite side. This increases the probability of initiation of the reduction reaction as compared with the trans isomer.

Discussion for Electronic Factors

Next, electronic factors will be discussed. The LUMO level is slightly lower for the cis isomer than for the trans isomer. Therefore, the cis isomer more readily receives an electron from an electrode, leading to a more rapidly proceeding reduction reaction.

Further, the difluorophosphate complex before decomposition is a six-coordinate phosphorus compound while the difluoro phosphoric acid derivative as the main component of SEI after decomposition is a five-coordinate phosphorus compound. It undergoes trans form from six-coordination to five-coordination when the difluorophosphate complex decomposes to generate a highly active intermediate, and the intermediate reacts with a functional group on the surface of a negative electrode. For the trans isomer, the bond angle of F—P—F before decomposition (six-coordination) is 180° while the bond angle of F—P—F after decomposition (five-coordination) is about 100°. Therefore, a large structural change is required. On the other hand, the cis isomer shows only a small change of from 90° (before decomposition, six-coordination) to about 100° (after decomposition, five-coordination). As clearly understood from the above, the energy required for the transition state of the reductive decomposition reaction is smaller in the cis isomer without a large structural change, and thus the reductive decomposition of the cis isomer is more favored than that of the trans isomer. This is not limited to a complex having phosphorus as the central element, but also can be applied to arsenic, antimony, and silicon.

Discussion for Different Performances of SEI

Considering that the reductive decomposition reaction proceeds in different rates between the cis isomer and the trans isomer, the difference in the performance of SEI formed therefrom will be discussed.

The reductive decomposition reaction rapidly proceeds in the cis isomer to rapidly form an SEI which mainly contains a derivative of difluorophosphoric acid and a derivative of carbonic acid. To date, it has been revealed that an SEI consisting of a derivative of difluorophosphoric acid has an excellent effect for improving the cycle characteristics, high-temperature storage properties, and output characteristics of a battery while an SEI consisting of a derivative of carbonic acid has an excellent effect for improving the cycle characteristics and high-temperature storage properties. The reductive decomposition reaction of the trans isomer is slower as compared with that of the cis isomer, and thus prompt formation of an SEI consisting only of a derivative of difluorophosphoric acid and a derivative of carbonic acid is difficult to obtain. Due to this, the reduction reaction of a solvent also proceeds concomitantly with it, resulting in formation of an SEI mainly containing a mixture of a derivative of difluorophosphoric acid and a derivative of carbonic acid from the difluorophosphate complex, and carbonic acid and an alkyl carbonate salt from a solvent. (The difluorophosphate complex is much more susceptible to decomposition than a solvent, but the number of solvent molecules is enormously large, and thus decomposition of a solvent also proceeds although it is very little.) An SEI consisting of an alkyl carbonate salt included therein can improve cycle characteristics and high-temperature storage properties, but may decrease cation conductivity as compared with an SEI consisting of a derivative of carbonic acid due to a reduced ratio of oxygen. Therefore, output characteristics may be improved only marginally, or may even be decreased.

As described above, the different rates of the reductive decomposition reaction between the cis isomer and the trans isomer may alter the selectivity of the reductive decomposition reaction (the presence or absence of solvent decomposition), resulting in different main components in SEIs formed therefrom. This is likely responsible for the difference in the effects of SEIs for improving the battery performance in the end.

As described above, output characteristics at low temperature after high-temperature storage can be improved by adding (1-Trans) in a certain amount relative to (1-Cis). The reasons of this will be discussed similarly in terms of the different properties of SEIs between the cis isomer and the trans isomer. In a lithium battery, lithium is gradually released from a negative electrode in a fully charged condition to react with a solvent during high-temperature storage as oxidative decomposition of the solvent proceeds on the surface of a positive electrode maintained at a high potential. Due to this, highly resistive decomposition products accumulate on the positive and negative electrodes. Further, reversibly available lithium is decreased, resulting in decreased battery performance (the charge-and-discharge rate and capacity are decreased). A negative-electrode SEI consisting of an alkyl carbonate salt has a low ionic conductivity, and thus is disadvantageous for output characteristics. However, it can reduce the release of lithium from the negative electrode during high-temperature storage to prevent a decreased capacity after high-temperature storage. As a result, a high capacity is maintained after high-temperature storage. When high-rate discharge capacities (output characteristics) at low temperature are compared after high-temperature storage, the amount of electricity obtained at high-rate discharge as compared with low-rate discharge is lower as compared with an electrolytic solution of (1-Cis) only. However, the absolute values of the amount of electricity obtained at high-rate discharge is higher for an electrolytic solution having a certain amount of (1-Trans) relative to (1-Cis) than an electrolytic solution having (1-Cis) only because the starting capacity is higher.

In the tetrafluoro ionic complex (1-Tetra) having tetradentate F atoms, a ligand other than F has lower electron density as compared with the difluoro ionic complex (1) having bidentate F atoms because of the strong electron-withdrawing effect of F. This makes the ligand more susceptible to a nucleophilic attack. Therefore, if a trace amount of water is present in an electrolytic solution, (1-Tetra) is selectively hydrolyzed instead of (1). For example, when the central element M is P, the moiety of tetrafluorophosphoric acid of (1-Tetra) is converted into a salt of hexafluorophosphoric acid by hydrolysis (a ligand other than F is disproportioned after leaving). The ligand moiety other than F leaves from the central element P, and is decomposed to release carbon dioxide and carbon monoxide. The amount of carbon dioxide and carbon monoxide released at this time is ½ mol equivalent relative to (1). This can significantly reduce the yield of carbon dioxide and carbon monoxide which otherwise may increase the internal pressure.

Others

Meanwhile, in general, a nonaqueous electrolytic solution is called a nonaqueous electrolyte when a nonaqueous solvent is used, and called a polymeric solid electrolyte when a polymer is used. Polymeric solid electrolytes include those containing a nonaqueous solvent as a plasticizing agent. It is noted that an electrochemical device is referred to as a nonaqueous electrolytic solution battery, the device including the present nonaqueous electrolytic solution; a negative-electrode material enabling reversible insertion and desorption of an alkali metal ion such as a lithium ion and a sodium ion or an alkaline earth metal ion; and a positive-electrode material enabling reversible insertion and desorption of an alkali metal ion such as a lithium ion and a sodium ion or an alkaline earth metal ion.

Electrolyte

There is no particular limitation for the electrolyte, and salts of any cations and any anions can be used. As specific examples, cations include alkali metal ions such as a lithium ion, a sodium ion, and a potassium ion; alkaline earth metal ions; quaternary alkylammonium ions; and the like. Anions include anions of hexafluorophosphoric acid, tetrafluoroboric acid, perchloric acid, hexafluoroarsenic acid, hexafluoroantimonic acid, trifluoromethanesulfonic acid, bis(trifluoromethanesulfonyl)imide, bis(pentafluoroethanesulfonyl)imide, (trifluoromethanesulfonyl) (pentafluoroethanesulfonyl)imide, bis(fluorosulfonyl)imide, (trifluoromethanesulfonyl) (fluorosulfonyl)imide, (pentafluoroethanesulfonyl) (fluorosulfonyl)imide, tris(trifluoromethanesulfonyl)methide, bis(difluorophosphonyl)imide, and the like. These electrolytes may be used alone, or may be used in a mixture in any combination or ratio of two or more depending on applications. Among these, cations of lithium, sodium, magnesium, and quaternary alkylammonium are preferred as cations, and anions of hexafluorophosphoric acid, tetrafluoroboric acid, bis(trifluoromethanesulfonyl)imide, bis(fluorosulfonyl)imide, and bis(difluorophosphonyl)imide are preferred as anions in view of energy density, output characteristics, lifetime, and the like of a battery.

Nonaqueous Solvent

There is no particular limitation for the nonaqueous solvent as long as it is an aprotic solvent in which the ionic complex according to the present invention can be dissolved. For example, carbonates, esters, ethers, lactones, nitriles, amides, sulfones, and the like can be used. Further, they may be used alone or as a mixed solvent of two or more. Specific examples can include ethylmethyl carbonate, dimethyl carbonate, diethyl carbonate, methylpropyl carbonate, ethylpropyl carbonate, methylbutyl carbonate, ethylene carbonate, propylene carbonate, butylene carbonate, methyl acetate, ethyl acetate, methyl propionate, ethyl propionate, diethyl ether, acetonitrile, propionitrile, tetrahydrofuran, 2-methyltetrahydrofuran, furan, tetrahydropyran, 1,3-dioxane, 1,4-dioxane, dibutyl ether, diisopropyl ether, 1,2-dimethoxyethane, N,N-dimethylformamide, dimethyl sulfoxide, sulfolane, γ-butyrolactone, γ-valerolactone, and the like.

Further, a nonaqueous solvent in which the ionic complex according to the present invention and the above electrolyte can be highly soluble is preferably selected from high-permittivity solvents and low-viscosity solvents. Specifically at least one selected from the group consisting of cyclic carbonate as a high-permittivity solvent and chain carbonate as a low-viscosity solvent are preferably included. More preferably, a solvent mixture in which cyclic carbonate and chain carbonate are combined is preferably included. Cyclic carbonate as a high-permittivity solvent shows slow ion transfer due to a high viscosity. Therefore, if viscosity is reduced, ion transport capability can be enhanced to increase ionic conductance over a wide range of temperature. Examples of cyclic carbonates can include ethylene carbonate and propylene carbonate, and examples of chain carbonates can include ethylmethyl carbonate, dimethyl carbonate, diethyl carbonate, and methylpropyl carbonate.

In addition, the nonaqueous solvent preferably further includes at least one compound selected from the group (V) consisting of vinylene carbonate, vinylethylene carbonate, ethynylethylene carbonate, and fluoroethylene carbonate. When at least one compound selected from the group (V) is contained, reductive decomposition of that compound on the surface of a negative electrode forms a stable film which can suppress reductive decomposition of a nonaqueous electrolytic solution on the surface of the negative electrode. This reaction film layer can cover the surface of the negative electrode, preventing side reactions such as decomposition of the nonaqueous solvent which otherwise occurs on the surface of the negative electrode.

Polymer

There is no particular limitation for the polymer which can be used to obtain a polymeric solid electrolyte including the ionic complex according to the present invention as long as it is an aprotic polymer in which the aforementioned ionic complexes and the aforementioned electrolyte can be solved. Examples can include polymers having polyethylene oxide in their main chains or side chains, homopolymers or copolymers of polyvinylidene fluoride, methacrylate ester polymers, polyacrylonitrile, and the like. When a plasticizing agent is added to these polymers, the above aprotic nonaqueous solvents may be used.

Electrolyte Concentration

In the present invention, there is no particular limitation for the concentration of an electrolyte in these ion conductors, but the lower limit is preferably 0.5 mol/L or more, more preferably 0.7 mol/L or more, and even more preferably 0.9 mol/L or more, and the upper limit is 5.0 mol/L or less, preferably 4.0 mol/L or less, and more preferably 2.0 mol/L or less. A concentration of less than 0.5 mol/L may decrease cycle characteristics and output characteristics of a nonaqueous electrolytic solution battery due to decreased ion conductivity. On the other hand, a concentration of more than 5.0 mol/L may increase the viscosity of a nonaqueous electrolytic solution, decreasing cycle characteristics and output characteristics of a nonaqueous electrolytic solution battery again due to decreased ion conductivity.

Method of Manufacturing Nonaqueous Electrolytic Solution

When a lithium salt is dissolved in manufacture of a nonaqueous electrolytic solution for use as, for example, a nonaqueous electrolytic solution for lithium-ion secondary batteries, the solution temperature of the nonaqueous electrolytic solution is controlled at 40° C. or below. This can prevent generation of free acid such as hydrogen fluoride (HF) which may be produced when a lithium salt in the nonaqueous electrolytic solution reacts with water in the system to undergo decomposition. As a result, decomposition of a nonaqueous solvent can also be prevented. Therefore, deterioration of the nonaqueous electrolytic solution can be prevented effectively. Further, in the step of dissolving a lithium salt, the lithium salt is added in small portions until the concentration of the entire lithium salt becomes 0.5 to 4.0 mol/L to prepare a solution. This can prevent generation of free acids such as HF in a similar manner.

For example, the following are preferably performed to maintain the solution temperature at 40° C. or below. A portion in a range of 10 to 35 mass % of the entire lithium salt is first added and dissolved in a nonaqueous solvent, and another portion in a range of 10 to 35 mass % of the entire lithium salt is then added and dissolved. This operation is repeated for 2 to 9 times, and then finally the remaining lithium salt is gradually added and dissolved.

In particular, when the nonaqueous electrolytic solution according to the present invention is prepared, an increased solution temperature of the nonaqueous electrolytic solution during preparation may promote the aforementioned side reactions. Therefore, deterioration of the nonaqueous electrolytic solution can be prevented by preventing an increase in temperature so that the solution temperature of the nonaqueous electrolytic solution is controlled at 40° C. or below. This can assure the quality of the nonaqueous electrolytic solution.

Additives

Further, a common additive may be added in any ratio to the nonaqueous electrolytic solution according to the present invention unless the spirit of the present invention is impaired. Specific examples can include compounds having effects for preventing overcharging, for forming a film on a negative-electrode, and for protecting a positive electrode such as cyclohexylbenzene, biphenyl, tert-butylbenzene, tert-amylbenzene, biphenyl, o-terphenyl, 4-fluorobiphenyl, fluorobenzene, 2,4-difluorobenzene, and difluoroanisole. Further, the nonaqueous electrolytic solution can be used after solidified with a gelatinizing agent or a crosslinked polymer as used in a nonaqueous electrolytic solution battery called a polymer battery.

2. Nonaqueous Electrolytic Solution Battery

The nonaqueous electrolytic solution battery according to the present invention includes (a) the present nonaqueous electrolytic solution, (b) a positive electrode, (c) a negative electrode, and (d) a separator.

(a) Present Nonaqueous Electrolytic Solution

The nonaqueous electrolytic solution battery according to the present invention includes the nonaqueous electrolytic solution as described in 1. Nonaqueous electrolytic solution.

(b) Positive Electrode (b) the positive electrode preferably includes at least one oxide and/or polyanion compound as a positive-electrode active material.

Positive-Electrode Active Material

For a lithium-ion secondary battery in which cations in an nonaqueous electrolytic solution are mostly lithium ions, there is no particular limitation for (b) the positive-electrode active material for a positive electrode as long as it is capable of charge and discharge, but examples of it include at least one selected from the group consisting of (A) a lithium-transition metal composite oxide having a layer structure and containing at least one selected from the group consisting of metal of nickel, manganese, and cobalt; (B) a lithium-manganese composite oxide having the spinel structure; (C) a lithium-containing olivine-type phosphate salt; and (D) a lithium-rich layered transition metal oxide having the stratified rock-salt structure.

((A) Lithium-Transition Metal Composite Oxide)

Examples of (A) the lithium-transition metal composite oxide having a layer structure and containing at least one metal of nickel, manganese, and cobalt as a positive-electrode active material include, for example, lithium-cobalt composite oxides, lithium-nickel composite oxides, lithium-nickel-cobalt composite oxides, lithium-nickel-cobalt-aluminum composite oxides, lithium-cobalt-manganese composite oxides, lithium-nickel-manganese composite oxides, lithium-nickel-manganese-cobalt composite oxides, and the like. Those in which some of the main transition metal atoms of these lithium-transition metal composite oxides are replaced with other elements such as Al, Ti, V, Cr, Fe, Cu, Zn, Mg, Ga, Zr, Si, B, Ba, Y, and Sn can also be used.

Specific examples of lithium-cobalt composite oxides and lithium-nickel composite oxides can include $LiCoO_2$, $LiNiO_2$, and lithium cobalt oxides having a hetero element such as Mg, Zr, Al, and Ti ($LiCo_{0.98}Mg_{0.01}Zr_{0.01}O_2$, $LiCo_{0.98}Mg_{0.01}Al_{0.01}O_2$, $LiCo_{0.975}Mg_{0.01}Zr_{0.005}Al_{0.01}O_2$, and the like). Lithium cobalt oxides having a rare earth compound adhered on the surface as described in WO2014/034043 may also be used. Further, those in which a portion of the particle surface of $LiCoO_2$ particulate powder is coated with aluminum oxide as described in Japanese Unexamined Patent Application, Publication No. 2002-151077 and others may be used.

Lithium-nickel-cobalt composite oxides and lithium-nickel-cobalt-aluminum composite oxides may be represented by the general formula (1-1).

$$Li_aNi_{1-b-c}Co_bM^1_cO_2 \qquad (1\text{-}1)$$

In the formula (1-1), $M^1$ is at least one element selected from Al, Fe, Mg, Zr, Ti, and B, and a is $0.9 \le a \le 1.2$, and b and c satisfy the requirements of $0.1 \le b \le 0.3$ and $0 \le c \le 0.1$, respectively.

These can be prepared in accordance with, for example, the method of manufacture as described in Japanese Unexamined Patent Application, Publication No. 2009-137834 and others. Specific examples include $LiNi_{0.8}Co_{0.2}O_2$, $LiNi_{0.85}Co_{0.10}Al_{0.05}O_2$, $LiNi_{0.87}Co_{0.10}Al_{0.03}O_2$, $LiNi_{0.6}Co_{0.3}Al_{0.1}O_2$, and the like.

Specific examples of lithium-cobalt-manganese composite oxides and lithium-nickel-manganese composite oxides include $LiNi_{0.5}Mn_{0.5}O_2$, $LiCo_{0.5}Mn_{0.5}O_2$, and the like.

Lithium-nickel-manganese-cobalt composite oxides include lithium-containing composite oxides represented by the general formula (1-2).

$$Li_dNi_eMn_fCo_gM^2_hO_2 \qquad (1\text{-}2)$$

In the formula (1-2), $M^2$ is at least one element selected from Al, Fe, Mg, Zr, Ti, B, and Sn, and d is $0.9 \le d \le 1.2$, and e, f, g, and h satisfy the requirements of $e+f+g+h=1$, $0 \le e \le 0.7$, $0 \le f \le 0.5$, $0 \le g \le 0.5$, and $h \ge 0$.

Preferred are lithium-nickel-manganese-cobalt composite oxides containing manganese in the range specified in the general formula (1-2) in order to improve structural stability and high-temperature safety of a lithium secondary battery. In particular, more preferred is those further containing cobalt in the range specified in the general formula (1-2) in order to improve high-rate properties of a lithium-ion secondary battery.

Specific examples include $Li[Ni_{1/3}Mn_{1/3}Co_{1/3}]O_2$, $Li[Ni_{0.45}Mn_{0.35}Co_{0.2}]O_2$, $Li[Ni_{0.5}Mn_{0.3}Co_{0.2}]O_2$, $Li[Ni_{0.6}Mn_{0.2}Co_{0.2}]O_2$, $Li[Ni_{0.49}Mn_{0.3}Co_{0.2}Zr_{0.01}]O_2$, Li[Ni$_{0.49}$Mn$_{0.3}$Co$_{0.2}$Mg$_{0.01}$]O$_2$, and the like, which have a charge-discharge range, for example, at 4.3 V or above.

((B) Lithium-Manganese Composite Oxide Having the Spinel Structure)

Examples of (B) the lithium-manganese composite oxide having the spinel structure as a positive-electrode active material include, for example, a spinel-type lithium-manganese composite oxide represented by the general formula (1-3).

$$Li_j(Mn_{2-k}M^3{}_k)O_4 \quad (1\text{-}3)$$

In the formula (1-3), M$^3$ is at least one metal element selected from Ni, Co, Fe, Mg, Cr, Cu, Al, and Ti, and j is 1.05≤j≤1.15, and k is 0≤k≤0.20.

Specific examples include LiMn$_2$O$_4$, LiMn$_{1.95}$Al$_{0.05}$O$_4$, LiMn$_{1.9}$Al$_{0.1}$O$_4$, LiMn$_{1.9}$Ni$_{0.1}$O$_4$, and LiMn$_{1.5}$Ni$_{0.5}$O$_4$, and the like.

((C) Lithium-Containing Olivine-Type Phosphate Salt)

Examples of (C) the lithium-containing olivine-type phosphate salt as a positive-electrode active material include, for example, those represented by the general formula (1-4).

$$LiFe_{1-n}M^4{}_nPO_4 \quad (1\text{-}4)$$

In the formula (1-4), M$^4$ is at least one selected from Co, Ni, Mn, Cu, Zn, Nb, Mg, Al, Ti, W, Zr, and Cd, and n is 0≤n≤1.

Specific example include LiFePO$_4$, LiCoPO$_4$, LiNiPO$_4$, LiMnPO$_4$, and the like. Among these, LiFePO$_4$ and/or LiMnPO$_4$ are preferred.

((D) Lithium-Rich Layered Transition-Metal Oxide)

Examples of (D) the lithium-rich layered transition-metal oxide having the stratified rock-salt structure as a positive-electrode active material include, for example, those represented by the general formula (1-5).

$$xLiM^5O_2\cdot(1-x)Li_2M^6O_3 \quad (1\text{-}5)$$

In the formula (1-5), x is a number satisfying 0<x<1, and M$^5$ is at least one metal element having a mean oxidation number of 3$^+$, and M$^6$ is at least one metal element having a mean oxidation number of 4$^+$. In the formula (1-5), M$^5$ is at least one metal element selected from Mn, Ni, Co, Fe, V, and Cr preferably having a valence of 3. That valence may be a mean oxidation number of 3 where a metal with a valence of 2 and a metal with a valence of 4 are used in the equivalent amount.

Further, in the formula (1-5), M$^6$ is preferably one or more metal elements selected from Mn, Zr, and Ti. Specific examples include 0.5[LiNi$_{0.5}$Mn$_{0.5}$O$_2$]·0.5[Li$_2$MnO$_3$], 0.5 [LiNi$_{2/3}$Co$_{1/3}$Mn$_{2/3}$O$_2$]·0.5 [Li$_2$MnO$_3$], 0.5 [LiNi$_{0.375}$Co$_{0.25}$Mn$_{0.375}$O$_2$ ]·0.5 [Li$_2$MnO$_3$], 0.5 [LiNi$_{0.375}$Co$_{0.125}$Fe$_{0.125}$Mn$_{0.375}$O$_2$ ]·0.5 [Li$_2$MnO$_3$], 0.45 [LiNi$_{0.375}$Co$_{0.25}$Mn$_{0.375}$O$_2$]·0.10 [Li$_2$TiO$_3$]·0.45 [Li$_2$MnO$_3$], and the like.

The positive-electrode active material (D) represented by the general formula (1-5) is known to have a high capacity in high-voltage charging at 4.4 V or more (in terms of Li) (for example, see U.S. Pat. No. 7,135,252).

These positive-electrode active materials can be prepared in accordance with the methods of manufacture and others described in, for example Japanese Unexamined Patent Application, Publication No. 2008-270201, WO2013/118661, Japanese Unexamined Patent Application, Publication No. 2013-030284, and the like.

The positive-electrode active material needs to contain at least one selected from (A) to (D) described above as the main component. Examples of other additives which may be added include, for example, transition element chalcogenides such as FeS$_2$, TiS$_2$, V$_2$O$_5$, MoO$_3$, and MoS$_2$; or electrically conductive polymers such as polyacethylene, poly(p-phenylene), polyaniline, and polypyrrole; activated carbon; radical-generating polymers; carbon materials; and the like.

Positive-Electrode Current Collector (b) The positive electrode has a positive-electrode current collector. As the positive-electrode current collector, for example, aluminum, stainless steel, nickel, titanium, or alloys thereof can be used.

Positive-Electrode Active-Material Layer

In (b) the positive electrode, for example, a positive-electrode active-material layer is formed on at least one surface of the positive-electrode current collector. The positive-electrode active-material layer includes, for example, the aforementioned positive-electrode active material, a binding agent, and, if desired, an electrically conductive agent.

Examples of the binding agent include polytetrafluoroethylene, poly(vinylidene fluoride), a styrene-butadiene rubber (SBR) resin, or the like.

As the electrically conductive agent, for example, carbon materials can be used such as acetylene black, Ketjen black, carbon fiber, or graphite (granular graphite and flaky graphite). Acetylene black and Ketjen black with low crystallinity are preferably used for the positive electrode.

(c) Negative Electrode (c) The negative electrode includes a negative-electrode active material.

Negative-Electrode Active Material

For a lithium-ion secondary battery in which cations in an nonaqueous electrolytic solution are mostly lithium ions, examples of the negative-electrode active material of (c) the negative electrode include, for example, those capable of doping/de-doping lithium ions which contain, for example, at least one selected from (E) a carbon material having a d value of the lattice plane [002] of 0.340 nm or less as determined by X ray diffraction; (F) a carbon material having a d value of the lattice plane [002] of more than 0.340 nm as determined by X ray diffraction; (G) an oxide of one or more metals selected from Si, Sn, and Al; (H) one or more metals selected from Si, Sn, and Al or an alloy comprising the one or more metals, or an alloy of lithium and the one or more metals or the alloy; (I) a lithium titanium oxide. These negative-electrode active materials may be used alone or in combination of two or more.

((E) Carbon material having a d value of the lattice plane [002] of 0.340 nm or less as determined by X ray diffraction)

Examples of (E) the carbon material having a d value of the lattice plane [002] of 0.340 nm or less as determined by X ray diffraction as a negative-electrode active material include, for example, pyrolytic carbons, cokes (for example, pitch coke, needle coke, petroleum coke, and the like), graphites, calcined products of organic polymer compounds (for example, those obtained by calcining and carbonizing a phenol resin, a furan resin, and the like at an appropriate temperature), carbon fiber, and activated carbon. These may be graphitized. The above carbon materials preferably have an interplanar spacing (d002) of the plane [002] of 0.340 nm or less as measured by the X-ray diffraction method. In particular, preferred is a graphite having a true density of 1.70 g/cm$^3$ or more or a high-crystallinity carbon material having characteristics similar to that.

((F) Carbon Material Having a d Value of the Lattice Plane [002] of More than 0.340 nm as Determined by X Ray Diffraction)

Examples of (F) the carbon material having a d value of the lattice plane [002] of more than 0.340 nm as determined by X ray diffraction as a negative-electrode active material include amorphous carbon, which is a carbon material showing almost no change in the layer structure even upon heat treatment at a high temperature of 2000° C. or more. For example, non-graphitizable carbon (hard carbon), mesocarbon microbeads (MCMB) calcined at 1500° C. or less, mesophase pitch carbon fiber (MCF), and the like. A representative example is Carbotron® P available from Kureha Corporation.

((G) Oxide of one or more metals selected from Si, Sn, and Al)

Examples of (G) the oxide of one or more metals selected from Si, Sn, and Al as a negative-electrode active material include, for example, silicon oxides, tin oxides, and the like, which are capable of doping/de-doping lithium ions.

Examples include $SiO_x$ having a structure in which ultra-fine particles of Si are dispersed in $SiO_2$ and the like. When this material is used as a negative-electrode active material, charge and discharge can be smoothly performed because Si reacted with Li is of ultrafine particles. Further, when a compound (paste) for forming a negative-electrode active-material layer is made of this material, the coatability and the adhesiveness of a negative-electrode mixture layer with a current collector are also good because $SiO_x$ particles themselves having the above structure have small surface areas.

It is noted that a higher capacity and better charge-discharge cycle characteristics can be simultaneously obtained when $SiO_x$ is used along with graphite as (E) the negative-electrode active material in a specific ratio. This is because $SiO_x$ shows a large volume change upon charge and discharge.

((H) One or more metals selected from Si, Sn, and Al or an alloy comprising the one or more metals, or an alloy of lithium and the one or more metals or the alloy)

Examples of (H) the one or more metals selected from Si, Sn, and Al or an alloy comprising the one or more metals, or an alloy of lithium and the one or more metals or the alloy as a negative-electrode active material include, for example, metals such as silicon, tin, and aluminum; silicon alloys; tin alloys; aluminum alloys; and the like. Materials in which these metals and alloys are alloyed with lithium during charge and discharge can also be used.

Preferred specific examples of these include elemental metals (for example, powdered materials) such as, for example, silicon (Si) and tin (Sn); alloys of the above metals; compounds containing the above metals; alloys including tin (Sn) and cobalt (Co) in the above metals; and the like as described in WO2004/100293, Japanese Unexamined Patent Application, Publication No. 2008-016424, and the like. Use of the above metals for electrodes is preferred because a high charge capacity can be obtained, and expansion and contraction of the volume upon charge and discharge are relatively small. Further, these metals are known to be alloyed with Li upon charging, leading to a high charge capacity when they are used for negative electrodes of lithium-ion secondary batteries. Therefore, use of these metals is also preferred in this regard.

Further, a negative-electrode active material formed from silicon pillars having a submicron diameter, a negative-electrode active material including silicon fiber, and the like as described in WO2004/042851, WO2007/083155, and the like can be used.

((I) Lithium Titanium Oxide)

Examples of (I) the lithium titanium oxide as a negative-electrode active material can include, for example, lithium titanates having the spinel structure, lithium titanates having the ramsdellite structure, and the like.

Lithium titanates having the spinel structure can include, for example, $Li_{4+\alpha}Ti_5O_{12}$ ($\alpha$ varies within the range of $0 \leq \alpha \leq 3$ due to charge and discharge reactions). Further, lithium titanates having the ramsdellite structure include, for example, $Li_{2+\beta}Ti_3O_7$ ($\beta$ varies within the range of $0 \leq \beta \leq 3$ due to charge and discharge reactions). These negative-electrode active materials can be prepared in accordance with the methods of manufacture and the like as described in, for example in Japanese Unexamined Patent Application, Publication No. 2007-018883, Japanese Unexamined Patent Application, Publication No. 2009-176752, and the like.

For example, hard carbon; oxides such as $TiO_2$, $V_2O_5$, and $MoO_3$; and the like may be used as a negative-electrode active material in a sodium-ion secondary battery where cations in a nonaqueous electrolytic solution are mostly sodium ions. For example, the followings can be used as a positive-electrode active material in a sodium-ion secondary battery where cations in a nonaqueous electrolytic solution are mostly sodium ions: sodium-containing transition metal composite oxides such as $NaFeO_2$, $NaCrO_2$, $NaNiO_2$, $NaMnO_2$, and $NaCoO_2$; mixtures of multiple transition metals such as Fe, Cr, Ni, Mn, and Co of those sodium-containing transition metal composite oxides; those in which some of the transition metals of these sodium-containing transition metal composite oxides are replaced with different metals other than the transition metals; phosphate compounds of transition metals such as $Na_2FeP_2O_7$ and $NaCo_3(PO_4)_2P_2O_7$; sulfides such as $TiS_2$ and $FeS_2$; or electrically conductive polymers such as polyacethylene, poly(p-phenylene), polyaniline, and polypyrrole; activated carbon; radical-generating polymers; carbon materials; and the like.

Negative-Electrode Current Collector (c) The negative electrode has a negative-electrode current collector. As the negative-electrode current collector, for example, copper, stainless steel, nickel, titanium, or alloys thereof can be used.

Negative-Electrode Active-Material Layer

In (c) the negative electrode, for example, a negative-electrode active-material layer is formed on at least one surface of the negative-electrode current collector. The negative-electrode active-material layer includes, for example, the aforementioned negative-electrode active material, a binding agent, and, if desired, an electrically conductive agent.

Examples of the binding agent include polytetrafluoroethylene, poly(vinylidene fluoride), a styrene-butadiene rubber (SBR) resin, or the like.

Examples of the electrically conductive agent include, for example, carbon materials such as acetylene black, Ketjen black, carbon fiber, or graphite (granular graphite and flaky graphite).

Method of Manufacturing Electrodes ((b) the Positive Electrode and (c) the Negative Electrode)

An electrode can be obtained, for example, by dispersing and kneading predetermined loading amounts of an active material, a binding agent, and, if desired, an electrically conductive agent into a solvent such as N-methyl-2-pyrrolidone (NMP) and water, and applying the resulting paste on a current collector, and drying to form an active-material layer. The resulting electrode is preferably compressed by a method such as roll press to adjust the electrode to a suitable density.

(d) Separator

The nonaqueous electrolytic solution battery according to the present invention includes (d) the separator. As a separator for preventing contact between (b) the positive electrode and (c) the negative electrode, non-woven fabrics and porous sheets made of polyolefins such as polypropylene and polyethylene; cellulose; paper; or glass fiber; and the like. These films are preferably microporous so that penetration by an electrolytic solution can be facilitated for easy permeation of ions.

Polyolefin separators include, for example, lithium-ion permeable membranes capable of electrically insulating the positive electrode from the negative electrode, for example, microporous polymer films such as porous polyolefin films. Specific examples of porous polyolefin films include, for example, porous polyethylene films alone, or multilayer films in which a porous polyethylene film and a porous polypropylene film are layered. Examples also include composite films with a porous polyethylene film and a polypropylene film, and the like.

Housing

As a housing for nonaqueous electrolytic solution batteries which can be used when assembling the present nonaqueous electrolytic solution battery, for example, metal cans of a coin-type, a cylinder-type, a rectangle-type, and the like; and laminate housings can be used. Materials for metal cans include, for example, nickel-plated steel sheets, stainless steel sheets, nickel-plated stainless steel sheets, aluminum or an alloy thereof, nickel, titanium, and the like. As laminate housings, for example, laminate films such as an aluminum laminate film, a stainless steel laminate film, laminate films of silica-coated polypropylene and polyethylene can be used.

There is no particular limitation for the configuration of the nonaqueous electrolytic solution battery according to the present embodiment, but the configuration may be such that an electrode element having a positive electrode and a negative electrode arranged in a countering manner, and a nonaqueous electrolytic solution are included inside a housing. There is no particular limitation for the shape of the nonaqueous electrolytic solution battery, but a coin-like, cylindrical, rectangular, or aluminum laminate sheet-like electrochemical device may be assembled with the components described above.

EXAMPLES

Below, the present invention will be described in more detail with reference to Examples, but the present invention shall not be limited to these in any sense. It is noted that Examples with sub-numbers may be collectively denoted, for example, Examples 1-1 to 1-56 may be collectively referred to as Example 1. The same may apply to Example 2 and so on and Comparative Examples, and electrolyte Nos.

Synthesis Examples 1 to 12

Below, the methods of synthesizing 12 types of difluoro ionic complexes (cis/trans isomers) and tetrafluoro ionic complexes will be described. The method disclosed in Patent Document 5 (Japanese Unexamined Patent Application, Publication No. 2003-137890), Nonpatent Document 1 (J. Chem. Soc. (A), 1970, 15, 2569-2574), and Patent Document 6 (Japanese Unexamined Patent Application (Translation of PCT Application), Publication No. 2003-505464) were adapted to synthesize ionic complexes. However, methods other than these may also be used for synthesis.

Synthesis Example 1

Synthesis of a difluoro ionic cis complex (1a-Cis) and a difluoro ionic trans complex (1a-Trans) in which the central metal M is P, and the ligand is oxalic acid, and the cation A is Li.

Synthesis Example 2

Synthesis of a tetrafluoro ionic complex (5a-Tetra) in which the central metal M is P, and the ligand is oxalic acid, and the cation A is Li.

Synthesis Example 3

Synthesis of a difluoro ionic cis complex (1b-Cis) and a difluoro ionic trans complex (1b-Trans) in which the central metal M is P, and the ligand is hexafluoroisobutanoic acid (HHIB), and the cation A is Li.

Synthesis Example 4

Synthesis of (6a-Cis) and (6a-Trans) as Na adducts of (1a-Cis) and (1a-Trans).

Synthesis Example 5

Synthesis of (5b-Tetra) as an Na adduct of (5a-Tetra).

Synthesis Example 6

Synthesis of (6b-Cis) and (6b-Trans) as K adducts of (1a-Cis) and (1a-Trans).

Synthesis Example 7

Synthesis of (6c-Cis) and (6c-Trans) as trimethylpropylammonium cation (TMPA) adducts of (1a-Cis) and (1a-Trans).

Synthesis Example 8

Synthesis of (6d-Cis) and (6d-Trans) as 1-butyl-1-methylpyrrolidinium cation (PP13) adducts of (1a-Cis) and (1a-Trans).

Synthesis Example 9

Synthesis of (1c-Cis) in which the anion moiety of (1-Cis) is (Cis-c), and A is Li, and (1c-Trans) in which the anion moiety of (1-Trans) is (Trans-c), and A is Li. Here, in each of (Cis-c) and (Trans-c), M=Si, X=O, Y=C, p, q=1, t=2, and r=0.

Synthesis Example 10

Synthesis of (5c-Tetra) as a K adduct of (5a-Tetra).

Synthesis Example 11

Synthesis of (5d-Tetra) as a TMPA adduct of (5a-Tetra).

Synthesis Example 12

Synthesis of (5e-Tetra) as a PP13 adduct of (5a-Tetra).

In any cases, raw materials and products were handled under a nitrogen atmosphere of a dew point of −50° C. or less. Further, a glass reactor used was dried at 150° C. for 12 hours or more, and then cooled to room temperature under a nitrogen stream of a dew point of −50° C. or less before use.

Synthesis Example 1

Synthesis of (1a-Cis) and (1a-Trans)

Lithium tris(oxalato)phosphate as a three-coordinate complex of oxalic acid was obtained according to the method disclosed in Patent Document 6 (Japanese Unexamined Patent Application (Translation of PCT Application), Publication No. 2003-505464). Lithium tris(oxalato)phosphate (30 g, 99.4 mmol) was dissolved in dimethyl carbonate (hereinafter, referred to as DMC) (120 mL), and hydrogen fluoride (hereinafter, referred to as HF) (11.9 g, 596.4 mmol) was then added. After stirring at 25° C. for 48 hours, residual HF and DMC were removed under reduced pressure. Then, DMC (60 mL) was added, and the concentrated residue was dissolved as much as possible, and then concentrated until the concentration of an Li salt became about 45 mass %. After removing insoluble components including oxalic acid by filtration, 49 g of a DMC solution of a mixture of (1a-Cis) and (1a-Trans) was obtained.

Dichloromethane (hereinafter, referred to as "$CH_2Cl_2$") was added to the DMC solution of the mixture at room temperature, and stirred for 12 hours to obtain a precipitated solid. The solid was separated from the mother liquor by filtration, and the mother liquor was distilled to remove DMC under reduced pressure until a solid was obtained. The precipitated solid and the solid obtained from the mother liquor were separately dissolved in DMC to separately prepare DMC with a concentration of 45 mass %, and $CH_2Cl_2$ was then added to allow a solid to precipitate. The solids were recovered separately by filtration, and the preparation of a DMC solution with a concentration of about 45 mass % and the precipitation of a solid were further repeated for several times by a similar procedure to obtain (1a-Cis) and (1a-Trans) with F and P purities of 99.9 mol % (as determined by NMR).

(1a-Cis) and (1a-Trans) were dissolved separately in acetonitrile, and subjected to LC/MS (the ESI method, polarity: negative, fragment voltage: 50 V) to measure molecular weight. A parent ion was observed at m/z 244.9 for both, which is consistent with a theoretical mass number of 244.93 (the anion moiety). Further, the steric conformation was determined by the single crystal X-ray structure analysis for (1a-Cis). FIG. 1 shows the analysis results of (1a-Cis).

The steric conformation was also determined by the single crystal X-ray structure analysis for (1a-Trans). (1a-Cis) and (1a-Trans) clearly have the same atomic composition but different structures because they have the same mass, and F-NMR and P-NMR show their peaks at different positions.

Synthesis Example 2

Synthesis of (5a-Tetra)

Reactions were performed according to the method described in Patent Document 5 (Japanese Unexamined Patent Application, Publication No. 2003-137890). To a 500 mL glass flask, added were 20.0 g (132 mmol) of $LiPF_6$, 110 mL of dimethyl carbonate (DMC), and 11.9 g (132 mmol) of oxalic acid. At this point, $LiPF_6$ was completely dissolved, but the majority of oxalic acid remained unresolved. With stirring at 25° C., 13.4 g (79 mmol) of $SiCl_4$ was added dropwise to the flask, and stirring was then continued for 4 hours. Subsequently, tetrafluorosilane and hydrochloric acid were removed under reduced pressure to obtain a crude DMC solution containing the ionic complex (5a-Tetra) as the main component (a purity of 91 mol %).

This solution was concentrated until the concentration of an Li salt became about 50 mass % to obtain 51 g of a concentrated liquid. After removing insoluble components by filtration, $CH_2Cl_2$ was added with stirring at room temperature. After stirring for 12 hours, a precipitated solid was recovered by filtration. Again, it was dissolved in DMC to prepare a DMC solution with an concentration of an Li-salt of about 50 mass %, and then the addition of $CH_2Cl_2$, precipitation of a solid, and recovery of a solid were performed by a similar procedure to obtain (5a-Tetra) with F and P purities of 99.9%.

Synthesis Example 3

Synthesis of (1b-Cis) and (1b-Trans) (1b-Cis) and (1b-Trans) were each obtained as in Synthesis Example 1 except that hexafluoro-2-hydroxyisobutyric acid was used as a raw material instead of oxalic acid.

Synthesis Example 4

Synthesis of (6a-Cis) and (6a-Trans) as Na adducts of (1a-Cis) and (1a-Trans)

A Dow Chemical strongly acidic cation exchange resin 252 (hereinafter, referred to as the ion exchange resin) was weighed out to give 500 g, and immersed in 0.1 N aqueous sodium hydroxide (2.5 kg), and stirred at 25° C. for 6 hours. The ion exchange resin was collected by filtration, and washed thoroughly with pure water until the pH of a wash liquid became 8 or less. Then, water was removed by drying under reduced pressure for 12 hours (120° C., 1.3 kPa).

The (1a-Cis)/EMC solution with a concentration of 10 mass % was prepared, to which the dried ion exchange resin in a weight corresponding to half of the weight of the liquid was added, and stirred at 25° C. for 6 hours. Then, the ion exchange resin was removed by filtration to obtain a (6a-Cis)/EMC solution (with a concentration of about 10 mass %) in which cations of $Li^+$ had been exchanged with $Na^+$. The ratio of $Na^+/Li^+$ was 99.5 when cations were quantified by ion chromatography.

Further, the (6a-Trans)/EMC solution with a concentration of about 10 mass % was obtained as in the method described above except that the (1a-Trans)/EMC solution with the same concentration was substituted for the (1a-Cis)/EMC solution.

Synthesis Example 5

Synthesis of (5b-Tetra) as an Na adduct of (5a-Tetra)

A (5b-Tetra)/EMC solution with a concentration of about 10 mass % in which cations of $Li^+$ had been exchanged with $Na^+$ was obtained by substituting a (5a-Tetra)/EMC solution for the (1a-Cis)/EMC solution used in Synthesis Example 4. The ratio of $Na^+/Li^+$ was 99.4 when cations were quantified by ion chromatography.

Synthesis Example 6

Synthesis of (6b-Cis) and (6b-Trans) as K adducts of (1a-Cis) and (1a-Trans) (6b-Cis)/EMC and (6 b-Trans)/EMC solutions with a concentration of about 10 mass % in which cations of $Li^+$ had been exchanged with $K^+$ were obtained by substituting 0.1 N aqueous potassium hydroxide (2.5 kg) for 0.1 N aqueous sodium hydroxide (2.5 kg) used in Synthesis Example 4. The ratio of $K^+/Li^+$ was 99.6 for both solutions when cations were quantified by ion chromatography.

Synthesis Example 7

Synthesis of (6c-Cis) and (6c-Trans) as TMPA adducts of (1a-Cis) and (1a-Trans)

To 90 g of EMC, 5.7 g (41.7 mmol) of trimethylpropylammonium chloride and 10.0 g (39.7 mmol) of (1a-Cis) were added, and stirred at 45° C. for 6 hours. After cooled to 5° C., insoluble materials were removed by filtration to obtain a (6c-Cis)/EMC solution (with a concentration of about 13 mass %) in which cations of $Li^+$ had been exchanged with trimethylpropylammonium cations (hereinafter, referred to as TMPA).

Further, the (6c-Trans)/EMC solution with a concentration of about 13 mass % was obtained as in the method described above except that (1a-Trans) in the same weight was substituted for (1a-Cis). The ratio of $TMPA/Li^+$ was 98.5 for both solutions when cations were quantified by ion chromatography.

Synthesis Example 8

Synthesis of (6d-Cis) and (6d-Trans) as PP13 adducts of (1a-Cis) and (1a-Trans)

To 90 g of EMC, 7.4 g (41.7 mmol) of 1-butyl-1-methylpyrrolidinium chloride and 10.0 g (39.7 mmol) of (1a-Cis) were added, and stirred at 45° C. for 6 hours. After cooled to 5° C., insoluble materials were removed by filtration to obtain a (6d-Cis)/EMC solution (with a concentration of about 15 mass %) in which cations of $Li^+$ had been exchanged with 1-butyl-1-methylpyrrolidinium cations (hereinafter, referred to as PP13).

Further, the (6d-Trans)/EMC solution with a concentration of about 15 mass % was obtained as in the method described above except that (1a-Trans) in the same weight was substituted for (1a-Cis). The ratio of $PP13/Li^+$ was 98.3 for both solutions when cations were quantified by ion chromatography.

Synthesis Example 9

Synthesis of (1c-Cis) and (1c-Trans) (1c-Cis) in which the anion moiety of the above (1-Cis) was (Cis-c) and A=Li, and (1c-Trans) in which the anion moiety of the above (1-Trans) was (Trans-c) and A=Li were each obtained by adapting the method described in Non-Patent Document 1 (J. Chem. Soc. (A), 1970, 15, 2569-2574).

Synthesis Example 10

Synthesis of (5c-Tetra) as a K adduct of (5a-Tetra)

A (5c-Tetra)/EMC solution with a concentration of about 10 mass % in which cations of $Li^+$ had been exchanged with $K^+$ was obtained by using 0.1 N aqueous potassium hydroxide (2.5 kg) instead of 0.1 N of aqueous sodium hydroxide (2.5 kg) used in Synthesis Example 4, and using a (5a-Tetra)/EMC solution instead of the (1a-Trans)/EMC solution. The ratio of $K^+/Li^+$ was 99.2 when cations were quantified by ion chromatography.

Synthesis Example 11

Synthesis of (5d-Tetra) as a TMPA adduct of (5a-Tetra)

A (5d-Tetra)/EMC solution (with concentration of about 11 mass %) in which cations of $Li^+$ had been exchanged with trimethylpropylammonium cations (hereinafter, TMPA) was obtained by using 7.9 g (39.7 mmol) of (5a-Tetra) instead of 10.0 g (39.7 mmol) of (1a-Trans) used in Synthesis Example 7. The ratio of $TMPA/Li^+$ was 98.6 when cations were quantified by ion chromatography.

Synthesis Example 12

Synthesis of (5e-Tetra) as a PP13 adduct of (5a-Tetra)

A (5e-Tetra)/EMC solution (with a concentration of about 13 mass %) in which cations of $Li^+$ had been exchanged with 1-butyl-1-methylpyrrolidinium cations (hereinafter, PP13) was obtained by using 7.9 g (39.7 mmol) of (5a-Tetra) instead of 10.0 g (39.7 mmol) of (1a-Trans) used in Synthesis Example 8. The ratio of $PP13/Li^+$ was 98.2 when cations were quantified by ion chromatography.

Preparation of Nonaqueous Electrolytic Solution No. 1 According to the Present Invention and Comparative Electrolytic Solution No. 1

In a dry box under a nitrogen atmosphere of a dew point of −50° C. or less, $LiPF_6$ as an electrolyte was dissolved and prepared in a preheated and dissolved nonaqueous solvent of ethylene carbonate (EC) and ethylmethyl carbonate (EMC) (volume ratio 1:2) so that the concentration of $LiPF_6$ was 1 mol/liter, and then various ionic complex/EMC solutions according to the present invention, the group (II) compounds, and others as described above were added in predetermined amounts to prepare the nonaqueous electrolytic solutions Nos. 1-1 to 1-56 according to the present invention and the comparative electrolytic solutions Nos. 1-1 to 1-6 as shown in Table 1.

It is noted that these preparations were performed as follows while cooled to control the solution temperature at 40° C. or below. First, 30 mass % of the entire $LiPF_6$ was added and dissolved in a predetermined amount of EMC, and another 30 mass % of the entire $LiPF_6$ was then added and dissolved. This operation was repeated for one more time, and then finally the remaining 10 mass % of $LiPF_6$ was added and dissolved. Subsequently, predetermined amounts of EC and EMC were added and mixed, and then various ionic complex/EMC solutions, the group (II) compounds, and others shown in Table 1 below were added, and the volume ratio of EC and EMC was finally adjusted to 1:2, and then stirred for 1 hour.

Evaluation: Storage Stability

Each of the nonaqueous electrolytic solutions No. 1 and the comparative electrolytic solutions No. 1 was subjected to accelerated tests to evaluate the stability after storage.

20 L stainless steel pressure containers equipped with a pressure gage were filled with 21 kg of the electrolytic solutions respectively, and stored at an environmental temperature of 45° C. for two months. Then, the internal pressure of the container was measured at an environmental temperature of 25° C. to calculate the gas yield generated during storage. The gas yields of the nonaqueous electrolytic solutions No. 1 and the comparative electrolytic solutions No. 1 are shown in Table 1 as relative values when the gas yield of the comparative electrolytic solution No. 1-1 is taken as 100.

The nonaqueous electrolytic solutions containing 3 types of compounds: the difluoro ionic complex (1a-Cis) in the cis configuration from Synthesis Example 1, 1,3-PS, and the tetrafluoro ionic complex (5a-Tetra) from Synthesis Example 2 (the electrolytic solutions Nos. 1-15 to 1-17), and similarly the nonaqueous electrolytic solutions containing 4 types of compounds: (1a-Cis), 1,3-PS, (1a-Trans), and the tetrafluoro ionic complex (5a-Tetra) (the electrolytic solutions Nos. 1-18 to 1-24) showed smaller gas yields during storage, preventing an increase in the internal pressure as compared with the nonaqueous electrolytic solutions which do not contain the tetrafluoro ionic complex (5a-Tetra) (for example, based on comparisons of "the electrolytic solution No. 1-4," with "the electrolytic solutions Nos. 1-15 to 1-17" and comparison of "the electrolytic solution No. 1-13" with the electrolytic solution No. 1-21").

Further, this gas-yield reducing effect was found to be enhanced as the ratio of the tetrafluoro ionic complex (5a-Tetra) to the difluoro ionic complex (1a-Cis), i. e., tetrafluoro ionic complex (1-Tetra)/difluoro ionic complex (1-Cis) (by the mass ratio) increased from 0.07 to 0.14 and 0.20 (for example, see "the electrolytic solutions Nos. 1-15 to 1-17").

TABLE 1

| Electrolytic solution No, | Group (I) compound (Cis isomer) | Content (mass %) | Group (II) compound | Content (mass %) | Group (III) compound Trans isomer | Content (mass %) | Trans isomer/ Cis isomer (mass ratio) |
|---|---|---|---|---|---|---|---|
| Electrolytic solution No. 1-1 | Synthesis Example 1 (1a-Cis) | 0.05 | 1,3-PS | 2.0 | — | — | — |
| Electrolytic solution No. 1-2 | | 0.1 | | 2.0 | — | — | — |
| Electrolytic solution No. 1-3 | | 0.8 | | 2.0 | — | — | — |
| Electrolytic solution No. 1-4 | | 1.0 | | 2.0 | — | — | — |
| Electrolytic solution No. 1-5 | | 3.0 | | 2.0 | — | — | — |
| Electrolytic solution No. 1-6 | | 5.0 | | 2.0 | — | — | — |
| Electrolytic solution No. 1-7 | Synthesis Example 1 (1a-Cis) | 1.0 | 1,3-PS | 0.05 | — | — | — |
| Electrolytic solution No. 1-8 | | 1.0 | | 0.1 | — | — | — |
| Electrolytic solution No. 1-9 | | 1.0 | | 0.5 | — | — | — |
| Electrolytic solution No. 1-10 | | 1.0 | | 1.0 | — | — | — |
| Electrolytic solution No. 1-11 | | 1.0 | | 5.0 | — | — | — |
| Electrolytic solution No. 1-12 | Synthesis Example 1 (1a-Cis) | 1.0 | 1,3-PS | 2.0 | Synthesis Example 1 (1a-Trans) | 0.002 | 0.002 |
| Electrolytic solution No. 1-13 | | 1.0 | | 2.0 | | 0.004 | 0.004 |
| Electrolytic solution No. 1-14 | | 1.0 | | 2.0 | | 0.01 | 0.01 |
| Electrolytic solution No. 1-15 | Synthesis Example 1 (1a-Cis) | 1.0 | 1,3-PS | 2.0 | — | — | — |
| Electrolytic solution No. 1-16 | | 1.0 | | 2.6 | — | — | — |
| Electrolytic solution No. 1-17 | | 1.0 | | 2.6 | — | — | — |
| Electrolytic solution No. 1-18 | Synthesis Example 1 (1a-Cis) | 0.5 | 1,3-PS | 0.2 | Synthesis Example 1 (1a-Trans) | 0.001 | 0.002 |
| Electrolytic solution No. 1-19 | | 0.5 | | 2.0 | | 0.0025 | 0.005 |
| Electrolytic solution No. 1-20 | | 1.0 | | 0.2 | | 0.002 | 0.002 |
| Electrolytic solution No. 1-21 | | 1.0 | | 2.0 | | 0.004 | 0.004 |
| Electrolytic solution No. 1-22 | | 1.0 | | 3.0 | | 0.01 | 0.01 |
| Electrolytic solution No. 1-23 | | 3.0 | | 2.0 | | 0.015 | 0.005 |
| Electrolytic solution No. 1-24 | | 3.0 | | 3.0 | | 0.03 | 0.01 |
| Electrolytic solution No. 1-25 | Synthesis Example 1 (1a-Cis) Synthesis Example 3 (1b-Cis) | 0.5 0.5 | 1,3-PS | 2.0 | Synthesis Example 1 (1a-Trans) | 0.004 | 0.004 |
| Electrolytic solution No. 1-26 | Synthesis Example 1 (1a-Cis) | 1.0 | 1,3-PS 1,4-BS | 1.0 1.0 | Synthesis Example 1 (1a-Trans) | 0.004 | 0.004 |
| Electrolytic solution No. 1-27 | Synthesis Example 1 (1a-Cis) | 1.0 | 1,3-PS | 2.0 | Synthesis Example 1 (1a-Trans) Synthesis Example 3 (1b-Trans) | 0.002 0.002 | 0.002 0.002 |
| Electrolytic solution No. 1-28 | Synthesis Example 1 (1a-Cis) | 1.0 | 1,3-PS | 2.0 | Synthesis Example 1 (1a-Trans) | 0.004 | 0.004 |
| Electrolytic solution No. 1-29 | Synthesis Example 3 (1b-Cis) | 1.0 | 1,3-PS | 2.0 | Synthesis Example 1 (1a-Trans) | 0.004 | 0.004 |
| Electrolytic solution No. 1-30 | Synthesis Example 1 (1a-Cis) | 1.0 | | 2.0 | Synthesis Example 3 (1b-Trans) | 0.004 | 0.004 |
| Electrolytic solution No. 1-31 | Synthesis Example 1 (1a-Cis) | 1.0 | | 2.0 | Synthesis Example 1 (1a-Trans) | 0.004 | 0.004 |
| Electrolytic solution No. 1-32 | Synthesis Example 4 (6a-Cis) | 1.0 | 1,3-PS | 2.0 | Synthesis Example 1 (1a-Trans) | 0.004 | 0.004 |
| Electrolytic solution No. 1-33 | Synthesis Example 6 (6b-Cis) | 1.0 | | 2.0 | | 0.004 | 0.004 |
| Electrolytic solution No. 1-34 | Synthesis Example 7 (6c-Cis) | 1.0 | | 2.0 | | 0.004 | 0.004 |
| Electrolytic solution No. 1-35 | Synthesis Example 8 (6d-Cis) | 1.0 | | 2.0 | | 0.004 | 0.004 |

TABLE 1-continued

| Electrolytic solution No. | | | | | | | |
|---|---|---|---|---|---|---|---|
| Electrolytic solution No. 1-36 | Synthesis Example 9 (1c-Cis) | 0.8 | | 2.0 | | 0.004 | 0.004 |
| Electrolytic solution No. 1-37 | Synthesis Example 1 (1a-Cis) | 1.0 | 1,3-PS | 2.0 | Synthesis Example 4 (6a-Trans) | 0.004 | 0.004 |
| Electrolytic solution No. 1-38 | | 1.0 | | 2.0 | Synthesis Example 6 (6b-Trans) | 0.004 | 0.004 |
| Electrolytic solution No. 1-39 | | 1.0 | | 2.0 | Synthesis Example 7 (6c-Trans) | 0.004 | 0.004 |
| Electrolytic solution No. 1-40 | | 1.0 | | 2.0 | Synthesis Example 8 (6d-Trans) | 0.004 | 0.004 |
| Electrolytic solution No. 1-41 | | 1.0 | | 2.0 | Synthesis Example 9 (1c-Trans) | 0.004 | 0.004 |
| Electrolytic solution No. 1-42 | Synthesis Example 1 (1a-Cis) | 1.0 | 1,3-PS | 2.0 | Synthesis Example 1 (1a-Trans) | 0.004 | 0.004 |
| Electrolytic solution No. 1-43 | | 1.0 | | 2.0 | | 0.004 | 0.004 |
| Electrolytic solution No. 1-44 | | 1.0 | | 2.0 | | 0.004 | 0.004 |
| Electrolytic solution No. 1-45 | Synthesis Example 1 (1a-Cis) | 1.0 | 1,3-PS | 2.0 | Synthesis Example 1 (1a-Trans) | 0.004 | 0.004 |
| Electrolytic solution No. 1-46 | | 1.0 | | 2.0 | | 0.004 | 0.004 |
| Electrolytic solution No. 1-47 | | 1.0 | | 2.0 | | 0.004 | 0.004 |
| Electrolytic solution No. 1-48 | Synthesis Example 1 (1a-Cis) | 1.0 | 1,3-PS | 2.0 | Synthesis Example 1 (1a-Trans) | 0.004 | 0.004 |
| Electrolytic solution No. 1-49 | | 1.0 | | 2.0 | | 0.004 | 0.004 |
| Electrolytic solution No. 1-50 | | 1.0 | | 2.0 | | 0.004 | 0.004 |
| Electrolytic solution No. 1-51 | Synthesis Example 1 (1a-Cis) | 1.0 | 1,3-PS | 2.0 | Synthesis Example 1 (1a-Trans) | 0.004 | 0.004 |
| Electrolytic solution No. 1-52 | | 1.0 | | 2.6 | | 0.004 | 0.004 |
| Electrolytic solution No. 1-53 | | 1.0 | | 2.0 | | 0.004 | 0.004 |
| Electrolytic solution No. 1-54 | Synthesis Example 1 (1a-Cis) | 1.0 | 1,3-PS | 2.0 | Synthesis Example 1 (1a-Trans) | 0.004 | 0.004 |
| Electrolytic solution No. 1-55 | | 1.0 | | 2.0 | | 0.004 | 0.004 |
| Electrolytic solution No. 1-56 | | 1.0 | | 2.0 | | 0.004 | 0.004 |
| Comparative electrolytic solution No. 1-1 | — | — | — | — | — | — | — |
| Comparative electrolytic solution No. 1-2 | Synthesis Example 1 (1a-Cis) | 1.0 | — | — | — | — | — |
| Comparative electrolytic solution No. 1-3 | Synthesis Example 1 (1a-Cis) Synthesis Example 3 (1b-Cis) | 0.5 0.5 | — | — | — | — | — |
| Comparative electrolytic solution No. 1-4 | — | — | 1,3-PS | 2.0 | — | — | — |
| Comparative electrolytic solution No. 1-5 | — | — | 1,3-PS | 2.0 | Synthesis Example 1 (1a-Trans) | 1.0 | — |
| Comparative electrolytic solution No. 1-6 | — | — | 1,3-PS | 2.0 | Synthesis Example 1 (1a-Trans) | 1.0 | — |

| Electrolytic solution No. | Group (IV) compound Tetrafluoro complex | Content (mass %) | Tetrafluoro complex/Cis isomer (mass ratio) | Group (V) compound | Content (mass %) | Gas yield during storage of electrolytic solution |
|---|---|---|---|---|---|---|
| Electrolytic solution No. 1-1 | — | — | — | — | — | 125.2 |
| Electrolytic solution No. 1-2 | — | — | — | — | — | 130.6 |
| Electrolytic solution No. 1-3 | — | — | — | — | — | 155.6 |
| Electrolytic solution No. 1-4 | — | — | — | — | — | 175.3 |
| Electrolytic solution No. 1-5 | — | — | — | — | — | 205.2 |
| Electrolytic solution No. 1-6 | — | — | — | — | — | 225.4 |
| Electrolytic solution No. 1-7 | — | — | — | — | — | 155.0 |
| Electrolytic solution No. 1-8 | — | — | — | — | — | 155.3 |
| Electrolytic solution No. 1-9 | — | — | — | — | — | 180.3 |
| Electrolytic solution No. 1-10 | — | — | — | — | — | 195.3 |
| Electrolytic solution No. 1-11 | — | — | — | — | — | 215.3 |
| Electrolytic solution No. 1-12 | — | — | — | — | — | 180.2 |
| Electrolytic solution No. 1-13 | — | — | — | — | — | 180.7 |
| Electrolytic solution No. 1-14 | — | — | — | — | — | 185.6 |
| Electrolytic solution No. 1-15 | Synthesis Example 2 (5a-Tetra) | 0.07 | 0.07 | — | — | 165.3 |
| Electrolytic solution No. 1-16 | | 0.14 | 0.14 | — | — | 155.3 |
| Electrolytic solution No. 1-17 | | 0.20 | 0.20 | — | — | 140.6 |
| Electrolytic solution No. 1-18 | Synthesis Example 2 (5a-Tetra) | 0.035 | 0.07 | — | — | 145.7 |
| Electrolytic solution No. 1-19 | | 0.06 | 0.12 | — | — | 135.1 |
| Electrolytic solution No. 1-20 | | 0.07 | 0.07 | — | — | 145.2 |

TABLE 1-continued

| | | | | | | |
|---|---|---|---|---|---|---|
| Electrolytic solution No. 1-21 | | 0.14 | 0.14 | — | — | 155.6 |
| Electrolytic solution No. 1-22 | | 0.20 | 0.20 | — | — | 160.7 |
| Electrolytic solution No. 1-23 | | 0.36 | 0.12 | — | — | 180.9 |
| Electrolytic solution No. 1-24 | | 0.60 | 0.20 | — | — | 205.3 |
| Electrolytic solution No. 1-25 | Synthesis Example 2 (5a-Tetra) | 0.14 | 0.14 | — | — | 152.8 |
| Electrolytic solution No. 1-26 | Synthesis Example 2 (5a-Tetra) | 0.14 | 0.14 | — | — | 155.2 |
| Electrolytic solution No. 1-27 | Synthesis Example 2 (5a-Tetra) | 0.14 | 0.14 | — | — | 154.0 |
| Electrolytic solution No. 1-28 | Synthesis Example 2 (5a-Tetra) | 0.07 | 0.07 | — | — | 159.3 |
| | Synthesis Example 5 (5b-Tetra) | 0.07 | 0.07 | | | |
| Electrolytic solution No. 1-29 | Synthesis Example 2 (5a-Tetra) | 0.14 | 0.14 | — | — | 154.3 |
| Electrolytic solution No. 1-30 | Synthesis Example 2 (5a-Tetra) | 0.14 | 0.14 | — | — | 155.4 |
| Electrolytic solution No. 1-31 | Synthesis Example 5 (5b-Tetra) | 0.14 | 0.14 | — | — | 158.3 |
| Electrolytic solution No. 1-32 | Synthesis | 0.14 | 0.14 | — | — | 160.0 |
| Electrolytic solution No. 1-33 | Example 2 | 0.14 | 0.14 | — | — | 163.0 |
| Electrolytic solution No. 1-34 | (5a-Tetra) | 0.14 | 0.14 | — | — | 161.5 |
| Electrolytic solution No. 1-35 | | 0.14 | 0.14 | — | — | 162.5 |
| Electrolytic solution No. 1-36 | | 0.14 | 0.14 | — | — | 163.9 |
| Electrolytic solution No. 1-37 | Synthesis | 0.14 | 0.14 | — | — | 159.8 |
| Electrolytic solution No. 1-38 | Example 2 | 0.14 | 0.14 | — | — | 162.6 |
| Electrolytic solution No. 1-39 | (5a-Tetra) | 0.14 | 0.14 | — | — | 161.4 |
| Electrolytic solution No. 1-40 | | 0.14 | 0.14 | — | — | 162.2 |
| Electrolytic solution No. 1-41 | | 0.14 | 0.14 | — | — | 163.5 |
| Electrolytic solution No. 1-42 | Synthesis | 0.14 | 0.14 | VC | 0.1 | 160.0 |
| Electrolytic solution No. 1-43 | Example 2 | 0.14 | 0.14 | | 1.0 | 171.4 |
| Electrolytic solution No. 1-44 | (5a-Tetra) | 0.14 | 0.14 | | 3.0 | 215.2 |
| Electrolytic solution No. 1-45 | Synthesis | 0.14 | 0.14 | VEC | 0.1 | 160.9 |
| Electrolytic solution No. 1-46 | Example 2 | 0.14 | 0.14 | | 1.0 | 172.4 |
| Electrolytic solution No. 1-47 | (5a-Tetra) | 0.14 | 0.14 | | 3.0 | 216.4 |
| Electrolytic solution No. 1-48 | Synthesis | 0.14 | 0.14 | EEC | 0.1 | 161.6 |
| Electrolytic solution No. 1-49 | Example 2 | 0.14 | 0.14 | | 1.0 | 173.1 |
| Electrolytic solution No. 1-50 | (5a-Tetra) | 0.14 | 0.14 | | 3.0 | 217.4 |
| Electrolytic solution No. 1-51 | Synthesis | 0.14 | 0.14 | FEC | 0.5 | 162.1 |
| Electrolytic solution No. 1-52 | Example 2 | 0.14 | 0.14 | | 2.0 | 173.6 |
| Electrolytic solution No. 1-53 | (5a-Tetra) | 0.14 | 0.14 | | 5.0 | 217.9 |
| Electrolytic solution No. 1-54 | Synthesis Example 10 (5c-Tetra) | 0.14 | 0.14 | — | — | 157.3 |
| Electrolytic solution No. 1-55 | Synthesis Example 11 (5d-Tetra) | 0.14 | 0.14 | — | — | 157.7 |
| Electrolytic solution No. 1-56 | Synthesis Example 12 (5e-Tetra) | 0.14 | 0.14 | — | — | 157.0 |
| Comparative electrolytic solution No. 1-1 | — | — | — | — | — | 100.0 |
| Comparative electrolytic solution No. 1-2 | — | — | — | — | — | 170.5 |
| Comparative electrolytic solution No. 1-3 | — | — | — | — | — | 171.2 |
| Comparative electrolytic solution No. 1-4 | — | — | — | — | — | 124.9 |
| Comparative electrolytic solution No. 1-5 | — | — | — | — | — | 177.6 |
| Comparative electrolytic solution No. 1-6 | Synthesis Example 2 (5a-Tetra) | 0.14 | — | — | — | 155.7 |

Production of NMC Positive Electrode

A LiNi$_{1/3}$Mn$_{1/3}$Co$_{1/3}$O$_2$ (NMC) powder as a positive-electrode active material was dry-mixed with acetylene black (electrically conductive agent), and then uniformly dispersed and mixed into the N-methyl-2-pyrrolidone (NMP) in which poly(vinylidene fluoride) (PVDF) was pre-dissolved, and NMP for adjusting the viscosity was further added to prepare an NMC mixture paste. The resulting paste was applied to an aluminum foil (current collector), dried, and pressurized. Then the aluminum foil was processed into a predetermined size to obtain a test NMC positive electrode. The ratio of solid contents in the positive electrode was NMC:electrically conductive agent: PVDF=85:5:10 (by the mass ratio).

Production of Graphite Negative Electrode

A graphite powder as a negative-electrode active material was uniformly dispersed and mixed into NMP in which PVDF as a binding agent was pre-dissolved, and NMP for adjusting the viscosity was further added to prepare a graphite mixture paste. The above paste was applied to a copper foil (current collector), dried, and pressurized. Then the copper foil was processed into a predetermined size to obtain a test graphite negative electrode. The ratio of solid contents in the negative electrode was graphite powder: PVDF=90:10 (by the mass ratio).

Production of Nonaqueous Electrolytic Solution Batteries

Aluminum laminate housing cells (with a capacity of 30 mAh) including the above test NMC positive electrode, the above test graphite negative electrode, and a cellulose separator were each impregnated with one of the nonaqueous electrolytic solutions Nos. 1-1 to 1-56 and the comparative electrolytic solutions Nos. 1-1 to 1-6 to obtain the nonaqueous electrolytic solution batteries according to Examples 1-1 to 1-56 and Comparative Examples 1-1 to 1-6. Example 1, Comparative Example 1: Evaluation of test cells Evaluation 1: Low-temperature property (0° C.) after 500 cycles at 60° C.

Each of the nonaqueous electrolytic solution batteries according to Example 1 and Comparative Example 1 was evaluated as described below.

First, the resulting cells were subjected to conditioning at an environmental temperature of 25° C. under the following conditions. That is, as the initial charge/discharge, constant-current and constant-voltage charge was performed at a 0.1 C rate (3 mA) to a charge upper limit voltage of 4.3 V, and then discharge was performed at a constant current of a 0.2 C rate (6 mA) to a discharge cutoff voltage of 3.0 V. Subsequently, a charge-discharge cycle was repeated 3 times as described below: constant-current and constant-voltage charge was performed at a 0.2 C rate (6 mA) to a charge upper limit voltage of 4.3 V, and then discharge was performed at a constant current of a 0.2 C rate (6 mA) to a discharge cutoff voltage of 3.0 V.

After this conditioning, charge and discharge tests were performed at an environmental temperature of 60° C. The following charge-discharge cycle was repeated for 500 times: constant-current and constant-voltage charge was performed at a 3 C rate (90 mA) to a charge upper limit voltage of 4.3 V, and discharge was performed at a constant current of a 3 C rate (90 mA) to a discharge cutoff voltage of 3.0 V.

Next, the nonaqueous electrolytic solution batteries were cooled to 25° C., and again discharged to 3.0 V. Then constant-current and constant-voltage charge was performed to 4.3 V at a 0.2 C rate at 0° C. Further, discharge was performed at a constant current of a 5 C rate (150 mA) to a discharge cutoff voltage of 3.0 V while maintaining the temperature at 0° C., and the capacity obtained at that time was taken as the low-temperature property (0° C.) after prolonged cycles at 60° C.

Evaluation 2: 5C-Rate Characteristics after 500 Cycles at 60° C.

After performing 500 cycles at an environmental temperature of 60° C. in Evaluation 1 as described above, the nonaqueous electrolytic solution batteries were cooled to 25° C., and then again discharged to 3.0 V. Then constant-current and constant-voltage charge was performed to 4.3 V at a 5 C rate at 25° C. Further, discharge was performed at a constant current of a 5 C rate (150 mA) to a discharge cutoff voltage of 3.0 V while maintaining the temperature at 25° C., and the capacity obtained at that time was taken as the 5C-rate characteristic (25° C.) after prolonged cycles at 60° C.

Evaluation 3: Low-Temperature Property (0° C.) after Stored at 60° C.

Each of the nonaqueous electrolytic solution batteries according to Example 1 and Comparative Example 1 was subjected to storage tests (stored for 10 days after charged to 4.3 V) at an environmental temperature of 60° C.

Next, the nonaqueous electrolytic solution batteries were cooled to 25° C., and again discharged to 3.0 V. Then constant-current and constant-voltage charge was performed to 4.3 V at a 0.2 C rate at 0° C. Further, discharge was performed at a constant current of a 5 C rate (150 mA) to a discharge cutoff voltage of 3.0 V while maintaining the temperature at 0° C., and the capacity obtained at that time was taken as the low-temperature property (0° C.) after stored at 60° C.

Various evaluation results of the nonaqueous electrolytic solution batteries according to Example 1 and Comparative Example 1 are shown in Table 2 as relative values when the corresponding evaluation results of the nonaqueous electrolytic solution battery according to Comparative Example 1-1 are taken as 100.

TABLE 2

|  | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
| --- | --- | --- | --- | --- |
| Example 1-1 | Electrolytic solution No.1-1 | 127.3 | 120.0 | 117.9 |
| Example 1-2 | Electrolytic solution No.1-2 | 131.2 | 124.1 | 121.5 |
| Example 1-3 | Electrolytic solution No.1-3 | 133.3 | 127.2 | 124.4 |
| Example 1-4 | Electrolytic solution No.1-4 | 134.5 | 128.6 | 125.3 |
| Example 1-5 | Electrolytic solution No.1-5 | 133.4 | 127.8 | 124.4 |
| Example 1-6 | Electrolytic solution No.1-6 | 127.7 | 118.9 | 117.6 |
| Example 1-7 | Electrolytic solution No.1-7 | 129.0 | 119.8 | 118.0 |
| Example 1-8 | Electrolytic solution No.1-8 | 132.5 | 127.5 | 118.8 |
| Example 1-9 | Electrolytic solution No.1-9 | 133.8 | 128.1 | 125.1 |
| Example 1-10 | Electrolytic solution No.1-10 | 132.9 | 126.7 | 124.5 |
| Example 1-11 | Electrolytic solution No.1-11 | 129.3 | 119.7 | 117.3 |
| Example 1-12 | Electrolytic solution No.1-12 | 135.3 | 128.8 | 125.9 |
| Example 1-13 | Electrolytic solution No.1-13 | 136.7 | 129.1 | 126.0 |
| Example 1-14 | Electrolytic solution No.1-14 | 137.9 | 129.4 | 126.1 |
| Example 1-15 | Electrolytic solution No.1-15 | 135.5 | 128.7 | 126.0 |
| Example 1-16 | Electrolytic solution No.1-16 | 136.9 | 129.5 | 126.2 |

TABLE 2-continued

| Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|
| Example 1-17 Electrolytic solution No.1-17 | 137.0 | 129.0 | 126.1 |
| Example 1-18 Electrolytic solution No.1-18 | 127.6 | 125.9 | 124.0 |
| Example 1-19 Electrolytic solution No.1-19 | 132.4 | 127.6 | 124.8 |
| Example 1-20 Electrolytic solution No.1-20 | 133.6 | 127.8 | 124.9 |
| Example 1-21 Electrolytic solution No.1-21 | 137.2 | 131.1 | 126.7 |
| Example 1-22 Electrolytic solution No.1-22 | 134.0 | 128.4 | 125.6 |
| Example 1-23 Electrolytic solution No.1-23 | 133.6 | 127.9 | 125.3 |
| Example 1-24 Electrolytic solution No.1-24 | 128.2 | 123.0 | 119.8 |
| Example 1-25 Electrolytic solution No.1-25 | 137.0 | 130.7 | 125.6 |
| Example 1-26 Electrolytic solution No.1-26 | 136.8 | 130.8 | 126.1 |
| Example 1-27 Electrolytic solution No.1-27 | 137.1 | 130.9 | 126.4 |
| Example 1-28 Electrolytic solution No.1-28 | 136.7 | 130.6 | 125.9 |
| Example 1-29 Electrolytic solution No.1-29 | 136.7 | 130.1 | 125.4 |
| Example 1-30 Electrolytic solution No.1-30 | 136.9 | 130.6 | 125.6 |
| Example 1-31 Electrolytic solution No.1-31 | 136.6 | 130.3 | 125.2 |
| Example 1-32 Electrolytic solution No.1-32 | 136.7 | 129.8 | 125.3 |
| Example 1-33 Electrolytic solution No.1-33 | 136.5 | 129.7 | 124.9 |
| Example 1-34 Electrolytic solution No.1-34 | 136.3 | 128.5 | 124.2 |
| Example 1-35 Electrolytic solution No.1-35 | 136.1 | 128.8 | 123.6 |
| Example 1-36 Electrolytic solution No.1-36 | 136.5 | 129.6 | 125.2 |
| Example 1-37 Electrolytic solution No.1-37 | 136.3 | 129.5 | 125.0 |
| Example 1-38 Electrolytic solution No.1-38 | 136.1 | 129.3 | 124.6 |
| Example 1-39 Electrolytic solution No.1-39 | 135.9 | 128.1 | 123.9 |
| Example 1-40 Electrolytic solution No.1-40 | 136.0 | 129.0 | 123.0 |
| Example 1-41 Electrolytic solution No.1-41 | 136.0 | 129.1 | 124.8 |
| Example 1-42 Electrolytic solution No.1-42 | 137.0 | 131.0 | 128.1 |
| Example 1-43 Electrolytic solution No.1-43 | 140.7 | 134.3 | 129.8 |
| Example 1-44 Electrolytic solution No.1-44 | 136.3 | 129.8 | 127.7 |
| Example 1-45 Electrolytic solution No.1-45 | 136.0 | 130.1 | 127.2 |
| Example 1-46 Electrolytic solution No.1-46 | 139.7 | 133.4 | 128.9 |
| Example 1-47 Electrolytic solution No.1-47 | 135.3 | 129.0 | 126.8 |
| Example 1-48 Electrolytic solution No.1-48 | 136.3 | 130.3 | 127.4 |
| Example 1-49 Electrolytic solution No.1-49 | 140.0 | 133.7 | 129.2 |
| Example 1-50 Electrolytic solution No.1-50 | 135.6 | 129.2 | 127.0 |
| Example 1-51 Electrolytic solution No.1-51 | 136.7 | 130.7 | 127.8 |
| Example 1-52 Electrolytic solution No.1-52 | 140.4 | 134.1 | 129.6 |
| Example 1-53 Electrolytic solution No.1-53 | 136.0 | 129.6 | 127.4 |
| Example 1-54 Electrolytic solution No.1-54 | 136.7 | 130.5 | 126.1 |
| Example 1-55 Electrolytic solution No.1-55 | 137.0 | 130.8 | 126.4 |
| Example 1-56 Electrolytic solution No.1-56 | 136.6 | 130.4 | 126.0 |
| Comparative Example 1-1 Comparative electrolytic solution No.1-1 | 100.0 | 100.0 | 100.0 |
| Comparative Example 1-2 Comparative electrolytic solution No.1-2 | 125.1 | 117.8 | 114.9 |
| Comparative Example 1-3 Comparative electrolytic solution No.1-3 | 124.7 | 116.2 | 108.2 |
| Comparative Example 1-4 Comparative electrolytic solution No 1-4 | 121.1 | 113.0 | 109.8 |
| Comparative Example 1-5 Comparative electrolytic solution No.1-5 | 125.5 | 119.2 | 117.5 |
| Comparative Example 1-6 Comparative electrolytic solution No.1-6 | 127.6 | 117.2 | 117.9 |

(Positive Electrode; NMC Negative Electrode; Graphite)

As seen from the results in Tables 1 and 2, Examples 1-1 to 1-56 which include the aforementioned group (I) and (II) compounds as essential ingredients of the nonaqueous electrolytic solution according to the present invention were found to be excellent in the low-temperature property (0° C.) after prolonged cycles at 60° C., the 5C-rate characteristic (25° C.) after prolonged cycles at 60° C., and the low-temperature property (0° C.) after stored at 60° C. as compared with Comparative Example 1-1 in which none of them was included, Comparative Examples 1-4 to 1-6 in which the group (I) compound among these was not included, and Comparative Examples 1-2 and 1-3 in which the group (II) compound among these was not included.

Combined Addition of Group (I) and (II) Compounds

For example, Examples 1-1 to 1-11 in which the difluoro ionic complex in the cis configuration (1a-Cis) from Synthesis Example 1 and 1,3-PS were included were found to be excellent in the low-temperature property (0° C.) after prolonged cycles at 60° C., the 5C-rate characteristic (25° C.) after prolonged cycles at 60° C., and the low-temperature property (0° C.) after stored at 60° C. as compared with Comparative Example 1-1 in which neither the above ionic complex nor 1,3-PS was included, Comparative Examples 1-2 in which only (1a-Cis) among these was included, and Comparative Examples 1-4 in which only 1,3-PS among these was included.

This can be explained as follows. When the difluoro ionic complex (1a-Cis) of the nonaqueous electrolytic solution according to the present invention and a cyclic sulfonic acid ester such 1,3-PC are included, these additives are reductively decomposed on a negative electrode in this order of the difluoro ionic complex (1a-Cis) and then VC during charge at the first cycle to form a stable film (SEI) on the surface of the negative electrode. That is, the above reaction film layer having a high ion conductivity and the SEI having long-term stability and covering the surface of the negative electrode can prevent side reactions such as decomposition of a solvent which otherwise occur on the surface of the negative electrode. This, in turn, can reduce the initial irreversible capacity of the nonaqueous electrolytic solution battery, and also improve long-term durability and output characteristics. Moreover, 1,3-PS also appears to form a film in the positive electrode side, enabling reduced oxidative decomposition of a nonaqueous solvent in the positive electrode side under a high-temperature environment. These appear to reflect significantly improved properties such as the discharge capacity (0° C.) after prolonged cycles at 60° C. and the 5C-rate characteristic (25° C.) as shown in Table 2, which supports that the present novel combination of the difluoro ionic complex (1a-Cis) and sulfonic acid ester such 1,3-PC can provide unprecedented property-improving effects.

Further, comparison of Example 1-4 with Comparative Example 1-5 revealed that the nonaqueous electrolytic solution battery according to Example 1-4 including the difluoro ionic complex (1a-Cis) in the cis configuration and 1,3-PC can show better results as compared with the nonaqueous electrolytic solution battery according to Comparative Example 1-5 including the difluoro ionic complex (1a-Trans) in the trans configuration and 1,3-PC. This can be explained as follows. Reductive decomposition of (1a-Cis) in the cis configuration has a different reaction rate than (1a-Trans) in the trans configuration, leading to different selectivity for the reductive decomposition reaction (the presence or absence of solvent decomposition). This may result in different main components of the SEIs formed therefrom, and may eventually result in different effects for improving battery performance for which the SEIs are responsible.

Comparison of Examples 1-1 to 1-11 revealed that the effect of the difluoro ionic complex (1a-Cis) and 1,3-PS were slightly observed even when the content of each was 0.05 mass %, and enhanced as the content of the ionic complex increased from 0.05 mass % to 0.1, 0.8, and 1.0 mass %.

When the content of the difluoro ionic complex (1a-Cis) was 3.0 mass % (Example 1-5), the effects were slightly decreased as compared with the case where the content was 1.0 mass % (Example 1-4). In the case of 5.0 mass % (Example 1-6), the effects were significantly decreased as compared with the case of 1.0 mass %. This may be assumed as follows. The viscosity of a nonaqueous electrolytic solution is increased when the content of the difluoro ionic complex (1a-Cis) reaches 3 mass % or more. This may interfere with movement of cations within a nonaqueous electrolytic solution battery, resulting in decreased battery performance.

When the content of 1,3-PS was 1.0 mass % (Example 1-10), the effect was slightly decreased as compared with a case where the content was 0.5 mass % (Example 1-9). When the content was 5.0 mass %, the effect was significantly decreased as compared with a case where the content was 0.5 mass %. This can be explained as follows: the battery performance may be decreased due to excessive formation of a passivation film on the surface of a negative-electrode active material, due to excessive film formation even in the positive electrode side when the content of 1,3-PS reaches 1.0 mass % or more, and due to other factors.

Further Addition of Group (III) Compound

Examples 1-12 to 1-14 where the difluoro ionic complex (1a-Cis) in the cis configuration and 1,3-PS were added, and the difluoro ionic complex (1a-Trans) in the trans configuration was further included were found to have a tendency for further increasing the discharge capacity (0° C.) after stored at 60° C. without decreasing the discharge capacity (0° C.) after prolonged cycles at 60° C. as compared with the nonaqueous electrolytic solution battery (Example 1-4) including the above (1a-Cis) and 1,3-PS.

Moreover, in Examples 1-12 to 1-14, as the ratio of the difluoro ionic complex (1a-Trans) in the trans configuration to the difluoro ionic complex (1a-Cis) in the cis configuration, i. e., difluoro ionic complex (1-Trans)/difluoro ionic complex (1-Cis) (by the mass ratio) increased from 0.002 to 0.004 and 0.01, the discharge capacity (0° C.) after stored at 60° C. was found to show a moderate improving tendency without impairing the discharge capacity (0° C.) after prolonged cycles at 60° C.

Moreover, even when the (5a-Tetra) as the group (IV) compound was included, further inclusion of the difluoro ionic complex in the trans conformation (1a-Trans) was found to have a tendency to further improve the discharge capacity (0° C.) after stored at 60° C. without impairing the discharge capacity (0° C.) after prolonged cycles at 60° C. (for example, comparison of Example 1-21 with Example 1-16).

Further Addition of Group (IV) Compound

Examples 1-15 to 1-17 where a nonaqueous electrolytic solution was used containing the difluoro ionic complex (1a-Cis) and 1,3-PS, and further including the tetrafluoro ionic complex (5a-Tetra) were found to have a tendency to further reduce the gas yields during storage of electrolytic solutions without impairing the discharge capacity (0° C.) after prolonged cycles at 60° C. and the 5C-rate characteristic (25° C.) as compared with the nonaqueous electrolytic solution battery (Example 1-4) including (1a-Cis) and 1,3-PS.

Further, in Examples 1-15 to 1-17, as the ratio of the tetrafluoro ionic complex (5a-Tetra) to the difluoro ionic complex (1a-Cis) in the cis configuration, i. e., tetrafluoro ionic complex (5a-Tetra)/difluoro ionic complex (1-Cis) (by the mass ratio) increased from 0.07 to 0.14 and 0.20, the gas yields during storage of electrolytic solutions were found to show an reducing tendency without impairing the discharge capacity (0° C.) after prolonged cycles at 60° C., the 5-C rate characteristic (25° C.), and the discharge capacity (0° C.) after stored at 60° C.

Moreover, in Examples 1-18 to 1-24, even when the difluoro ionic complex (1a-Trans) as a group (III) compound was included, further inclusion of the tetrafluoro ionic complex (5a-Tetra) was found to enable reduction of the gas yields during storage of electrolytic solutions without impairing the discharge capacity (0° C.) after prolonged cycles at 60° C., the 5-C rate characteristic (25° C.), and the discharge capacity (0° C.) after stored at 60° C.

Examples in which the Types of the Group (I) to (IV) Compounds were Changed

Examples 1-25 to 1-31 in which the difluoro ionic complex in the cis configuration (1b-Cis) from Synthesis Example 3 was used as the group (I) compound, and 1,4-BS was used as the group (II) compound, and the difluoro ionic complex in the trans configuration (1b-Trans) from Synthesis Example 3 was used as the group (III) compound, and the tetrafluoro ionic complex (5b-Tetra) from Synthesis Example 5 was used as the group (IV) compound were found to be excellent in the low-temperature property (0° C.) after prolonged cycles at 60° C., the 5C-rate characteristic (25° C.) after prolonged cycles at 60° C., and the low-temperature property (0° C.) after stored at 60° C. (and reduced gas yields during storage of electrolytic solutions) in a similar way as described above.

Examples in which the Cationic Species of the Group (I) Compound was Changed

Comparison of Examples 1-21, 1-32, and 1-33 in which the ionic complexes (1a-Cis), (6a-Cis), and (6b-Cis) having Li$^+$, Na$^+$, and K$^+$ as a cation were used as the group (I) compound revealed that there was no significant difference in the effect thereof, and all showed an excellent low-temperature property (0° C.) after prolonged cycles at 60° C., 5C-rate characteristic (25° C.) after prolonged cycles at 60° C., and low-temperature property (0° C.) after stored at 60° C. (and reduction in the gas yields during storage of electrolytic solutions). Similarly, comparisons of Examples 1-21, 1-34, and 1-35 where the ionic complexes (1a-Cis), (6c-Cis), and (6d-Cis) having Li$^+$, TMPA, and PP13 as cations were used as the group (I) compound revealed that Li$^+$ showed the best results although TMPA and PP13 showed a certain effect. This may be because the content of anion sides as the effective moieties was decreased due to the large molecular weights of the cations of TMPA and PP13, and because some of TMPA and PP13 were reductively or oxidatively decomposed, and decomposition residues were deposited as highly resistive materials on the surface of an electrode.

Example in which the Central Element M of the Group (I) Compound was Changed

As shown in Example 1-36, (1c-Cis) in which the central element of P was replaced with Si had a low solubility, and was not sufficiently dissolved at 1.0 mass %, but showed a relatively good effect when added at 0.8 mass % (comparison of Examples 1-21 and 1-36).

Examples in which the Cationic Species and the Central Element M of the Group (III) Compound were Changed As shown in Examples 1-37 to 1-41, Examples where the difluoro ionic complexes (6a-Trans, 6b-Trans, 6c-Trans, and 6d-Trans) in the trans configuration having different cation species and the difluoro ionic complex (1c-Trans) in the trans configuration in which the central element of P was replaced with Si were used as the group (III) compound similarly showed a superior low-temperature property (0° C.) after prolonged cycles at 60° C., a superior 5C-rate characteristic (25° C.) after prolonged cycles at 60° C., and a superior low-temperature property (0° C.) after stored at 60° C. (and reduced gas yields during storage of electrolytic solutions).

Further Addition of Group (V) Compound

Examples 1-42 to 1-56 including nonaqueous electrolytic solutions containing the difluoro ionic complex in the cis configuration (1a-Cis) from Synthesis Example 1, 1,3-PS, the difluoro ionic complex in the trans configuration (1a-Trans) from Synthesis Example 1, and the tetrafluoro ionic complex (5a-Tetra) from Synthesis Example 2 as well as the group (V) such as VC, VEC, EEC, and FEC were found to have a tendency to improve the discharge capacity (0° C.) after prolonged cycles at 60° C., the 5C-rate characteristic (25° C.), and the discharge capacity (0° C.) after stored at 60° C. depending on the addition amount of the group (V) as compared with the nonaqueous electrolytic solution battery (Example 1-21) including the above (1a-Cis), 1,3-PS, the above (1a-Trans), and the above (5a-Tetra). In some cases, a large addition amount of the group (V) tended to increase the viscosity of a nonaqueous electrolytic solution to interfere with movement of cations within a nonaqueous electrolytic solution battery, resulting in reduced battery performance.

Preparation of Nonaqueous Electrolytic Solutions No. 2 to No. 11 According to the Present Invention, and Comparative Electrolytic Solutions No. 2 to No. 11

The nonaqueous electrolytic solutions No. 2 to No. 11 according to the present invention were prepared in a similar way as in the nonaqueous electrolytic solution No. 1-1. That is, LiPF$_6$ as an electrolyte was dissolved and prepared in a nonaqueous solvent of EC and EMC (volume ratio 1:2) so that the concentration of LiPF$_6$ was 1 mol/liter, and then various ionic complex/EMC solutions according to the present invention, the group (II) compounds, and others were added in predetermined amounts as shown in Tables 3 and 4 below to prepare various nonaqueous electrolytic solutions and comparative electrolytic solutions.

Evaluation: Storage Stability

Each of the nonaqueous electrolytic solutions Nos. 2 to 11 was subjected to accelerated tests to evaluate the stability after storage in a similar way as in the nonaqueous electrolytic solution No. 1-1. The gas yields of these electrolytic solutions are each shown in Tables 3 and 4 as relative values when the gas yield of the comparative electrolytic solution No. 1-1 is taken as 100.

The nonaqueous electrolytic solution containing 3 types of compounds: the difluoro ionic complex (1a-Cis) in the cis configuration from Synthesis Example 1, 1,3-PRS, and the tetrafluoro ionic complex (5a-Tetra) from Synthesis Example 2 (the electrolytic solution No. 2-3), and similarly the nonaqueous electrolytic solution containing 4 types of compounds: (1a-Cis), 1,3-PRS, (1a-Trans), and the tetrafluoro ionic complex (5a-Tetra) showed smaller gas yields during storage, preventing an increase in the internal pressure as compared with the nonaqueous electrolytic solutions which did not contain the tetrafluoro ionic complex (5a-Tetra) (for example, based on comparison of "the electrolytic solution No. 2-1" with "the electrolytic solution No. 2-3" and comparison of "the electrolytic solution No. 2-2" with "the electrolytic solution No. 2-4").

A similar tendency was observed for the electrolytic solutions containing the compounds represented by the formulae (II-2a-4), (II-3a-1), (II-3b-1), and (II-3a-15) instead of 1,3-PRS.

Examples 2 to 11 and Comparative Examples 2 to 11

Production and Evaluation of Nonaqueous Electrolytic Solution Batteries

Aluminum laminate housing cells (with a capacity of 30 mAh) including the test NMC positive electrode, the test graphite negative electrode, and a cellulose separator were each impregnated with one of the various nonaqueous electrolytic solutions and comparative electrolytic solutions shown in Tables 3 and 4 by a similar procedure as in the nonaqueous electrolytic solution battery according to Example 1-1 described above to produce the nonaqueous electrolytic solution batteries according to Examples and Comparative Examples as shown in Tables 5 and 6. These nonaqueous electrolytic solution batteries were subjected to the following evaluations in a similar way as in Example 1-1 described above.

Evaluation 1: Low-temperature property (0° C.) 500 cycles at 60° C.

Evaluation 2: 5C-rate characteristic after 500 cycles after at 60° C.

Evaluation 3: Low-temperature property (0° C.) after stored at 60° C.

Various evaluations of these nonaqueous electrolytic solution batteries are shown in Tables 5 and 6 as relative values when the corresponding evaluation results of the nonaqueous electrolytic solution battery according to Comparative Example 1-1 are taken as 100.

TABLE 3

| Electrolytic solution No, | Group (I) compound (Cis isomer) | Content (mass %) | Group (II) compound | Content (mass %) | Group (III) compound Trans isomer | Content (mass %) | Trans isomer/ Cis isomer (mass ratio) |
|---|---|---|---|---|---|---|---|
| Electrolytic solution No. 2-1 | Synthesis Example 1 (1a-Cis) | 1.0 | 1,3-PRS | 1.0 | — | — | — |
| Electrolytic solution No. 2-2 | Synthesis Example 1 (1a-Cis) | 1.0 | 1,3-PRS | 1.0 | Synthesis Example 1 (1a-Trans) | 0.004 | 0.004 |
| Electrolytic solution No. 2-3 | Synthesis Example 1 (1a-Cis) | 1.0 | 1,3-PRS | 1.0 | — | — | — |
| Electrolytic solution No. 2-4 | Synthesis Example 1 (1a-Cis) | 1.0 | 1,3-PRS | 1.0 | Synthesis Example 1 (1a-Trans) | 0.004 | 0.004 |
| Electrolytic solution No. 2-5 | Synthesis Example 1 (1a-Cis) | 1.0 | 1,3-PRS | 1.0 | Synthesis Example 1 (1a-Trans) | 0.004 | 0.004 |
| Electrolytic solution No. 3-1 | Synthesis Example 1 (1a-Cis) | 1.0 | Formula (II-2a-4) | 1.0 | — | — | — |
| Electrolytic solution No. 3-2 | Synthesis Example 1 (1a-Cis) | 1.0 | Formula (II-2a-4) | 1.0 | Synthesis Example 1 (1a-Trans) | 0.004 | 0.004 |
| Electrolytic solution No. 3-3 | Synthesis Example 1 (1a-Cis) | 1.0 | Formula (II-2a-4) | 1.0 | — | — | — |
| Electrolytic solution No. 3-4 | Synthesis Example 1 (1a-Cis) | 1.0 | Formula (II-2a-4) | 1.0 | Synthesis Example 1 (1a-Trans) | 0.004 | 0.004 |
| Electrolytic solution No. 3-5 | Synthesis Example 1 (1a-Cis) | 1.0 | Formula (II-2a-4) | 1.0 | Synthesis Example 1 (1a-Trans) | 0.004 | 0.004 |
| Electrolytic solution No. 4-1 | Synthesis Example 1 (1a-Cis) | 1.0 | Formula (II-3a-1) | 1.0 | — | — | — |
| Electrolytic solution No. 4-2 | Synthesis Example 1 (1a-Cis) | 1.0 | Formula (II-3b-1) | 1.0 | — | — | — |
| Electrolytic solution No. 4-3 | Synthesis Example 1 (1a-Cis) | 1.0 | Formula (II-3a-1) | 1.0 | Synthesis Example 1 (1a-Trans) | 0.004 | 0.004 |
| Electrolytic solution No. 4-4 | Synthesis Example 1 (1a-Cis) | 1.0 | Formula (II-3b-1) | 1.0 | Synthesis Example 1 (1a-Trans) | 0.004 | 0.004 |
| Electrolytic solution No. 4-5 | Synthesis Example 1 (1a-Cis) | 1.0 | Formula (II-3a-1) | 1.0 | — | — | — |
| Electrolytic solution No. 4-6 | Synthesis Example 1 (1a-Cis) | 1.0 | Formula (II-3a-1) | 1.0 | Synthesis Example 1 (1a-Trans) | 0.004 | 0.004 |
| Electrolytic solution No. 4-7 | Synthesis Example 1 (1a-Cis) | 1.0 | Formula (II-3b-1) | 1.0 | — | — | — |
| Electrolytic solution No. 4-8 | Synthesis Example 1 (1a-Cis) | 1.0 | Formula (II-3b-1) | 1.0 | Synthesis Example 1 (1a-Trans) | 0.004 | 0.004 |
| Electrolytic solution No. 4-9 | Synthesis Example 1 (1a-Cis) | 1.0 | Formula (II-3a-1) | 1.0 | Synthesis Example 1 (1a-Trans) | 0.004 | 0.004 |
| Electrolytic solution No. 4-10 | Synthesis Example 1 (1a-Cis) | 1.0 | Formula (II-3b-1) | 1.0 | Synthesis Example 1 (1a-Trans) | 0.004 | 0.004 |
| Electrolytic solution No. 5-1 | Synthesis Example 1 (1a-Cis) | 1.0 | Formula (II-3a-15) | 1.0 | — | — | — |
| Electrolytic solution No. 5-2 | Synthesis Example 1 (1a-Cis) | 1.0 | Formula (II-3a-15) | 1.0 | Synthesis Example 1 (1a-Trans) | 0.004 | 0.004 |
| Electrolytic solution No. 5-3 | Synthesis Example 1 (1a-Cis) | 1.0 | Formula (II-3a-15) | 1.0 | — | — | — |
| Electrolytic solution No. 5-4 | Synthesis Example 1 (1a-Cis) | 1.0 | Formula (II-3a-15) | 1.0 | Synthesis Example 1 (1a-Trans) | 0.004 | 0.004 |

TABLE 3-continued

| Electrolytic solution No. 5-5 | Synthesis Example 1 (1a-Cis) | 1.0 | Formula (II-3a-15) | 1.0 | Synthesis Example 1 (1a-Trans) | 0.004 | 0.004 |
|---|---|---|---|---|---|---|---|
| Comparative electrolytic solution No. 1-1 | — | — | — | — | — | — | — |
| Comparative electrolytic solution No. 2-1 | — | — | 1,3-PRS | 1.0 | — | — | — |
| Comparative electrolytic solution No. 2-2 | — | — | 1,3-PRS | 1.0 | (1a-Trans) | 1.0 | — |
| Comparative electrolytic solution No. 2-3 | — | — | 1,3-PRS | 1.0 | (1a-Trans) | 1.0 | — |
| Comparative electrolytic solution No. 3-1 | — | — | Formula (II-2a-4) | 1.0 | — | — | — |
| Comparative electrolytic solution No. 3-2 | — | — | Formula (II-2a-4) | 1.0 | Synthesis Example 1 (1a-Trans) | 1.0 | — |
| Comparative electrolytic solution No. 3-3 | — | — | Formula (II-2a-4) | 1.0 | Synthesis Example 1 (1a-Trans) | 1.0 | — |
| Comparative electrolytic solution No. 4-1 | — | — | Formula (II-3a-1) | 1.0 | — | — | — |
| Comparative electrolytic solution No. 4-2 | — | — | Formula (II-3a-1) | 1.0 | Synthesis Example 1 (1a-Trans) | 1.0 | — |
| Comparative electrolytic solution No. 4-3 | — | — | Formula (II-3a-1) | 1.0 | Synthesis Example 1 (1a-Trans) | 1.0 | — |
| Comparative electrolytic solution No. 4-4 | — | — | Formula (II-3b-1) | 1.0 | — | — | — |
| Comparative electrolytic solution No. 4-5 | — | — | Formula (II-3b-1) | 1.0 | Synthesis Example 1 (1a-Trans) | 1.0 | — |
| Comparative electrolytic solution No. 4-6 | — | — | Formula (II-3b-1) | 1.0 | Synthesis Example 1 (1a-Trans) | 1.0 | — |
| Comparative electrolytic solution No. 5-1 | — | — | Formula (II-3a-15) | 1.0 | — | — | — |
| Comparative electrolytic solution No. 5-2 | — | — | Formula (II-3a-15) | 1.0 | Synthesis Example 1 (1a-Trans) | 1.0 | — |
| Comparative electrolytic solution No. 5-3 | — | — | Formula (II-3a-15) | 1.0 | Synthesis Example 1 (1a-Trans) | 1.0 | — |

| Electrolytic solution No. | Group (IV) compound Tetrafluoro complex | Content (mass %) | Tetrafluoro complex/Cis isomer (mass ratio) | Group (V) compound | Content (mass %) | Gas yield during storage of electrolytic solution |
|---|---|---|---|---|---|---|
| Electrolytic solution No. 2-1 | — | — | — | — | — | 175.0 |
| Electrolytic solution No. 2-2 | — | — | — | — | — | 180.4 |
| Electrolytic solution No. 2-3 | Synthesis Example 2 (5a-Tetra) | 0.14 | 0.14 | — | — | 155.0 |
| Electrolytic solution No. 2-4 | Synthesis Example 2 (5a-Tetra) | 0.14 | 0.14 | — | — | 155.3 |
| Electrolytic solution No. 2-5 | Synthesis Example 2 (5a-Tetra) | 0.14 | 0.14 | VC | 1.0 | 171.1 |
| Electrolytic solution No. 3-1 | — | — | — | — | — | 175.5 |
| Electrolytic solution No. 3-2 | — | — | — | — | — | 180.9 |
| Electrolytic solution No. 3-3 | Synthesis Example 2 (5a-Tetra) | 0.14 | 0.14 | — | — | 155.4 |
| Electrolytic solution No. 3-4 | Synthesis Example 2 (5a-Tetra) | 0.14 | 0.14 | — | — | 155.7 |
| Electrolytic solution No. 3-5 | Synthesis Example 2 (5a-Tetra) | 0.14 | 0.14 | VC | 1.0 | 171.6 |
| Electrolytic solution No. 4-1 | — | — | — | — | — | 176.2 |
| Electrolytic solution No. 4-2 | — | — | — | — | — | 176.4 |
| Electrolytic solution No. 4-3 | — | — | — | — | — | 181.6 |
| Electrolytic solution No. 4-4 | — | — | — | — | — | Not measured |

TABLE 3-continued

| Electrolytic solution No. 4-5 | Synthesis Example 2 (5a-Tetra) | 0.14 | 0.14 | — | — | 156.0 |
|---|---|---|---|---|---|---|
| Electrolytic solution No. 4-6 | Synthesis Example 2 (5a-Tetra) | 0.14 | 0.14 | — | — | 156.3 |
| Electrolytic solution No. 4-7 | Synthesis Example 2 (5a-Tetra) | 0.14 | 0.14 | — | — | 156.0 |
| Electrolytic solution No. 4-8 | Synthesis Example 2 (5a-Tetra) | 0.14 | 0.14 | — | — | 156.3 |
| Electrolytic solution No. 4-9 | Synthesis Example 2 (5a-Tetra) | 0.14 | 0.14 | VC | 1.0 | 172.3 |
| Electrolytic solution No. 4-10 | Synthesis Example 2 (5a-Tetra) | 0.14 | 0.14 | VC | 1.0 | Not measured |
| Electrolytic solution No. 5-1 | — | — | — | — | — | 175.1 |
| Electrolytic solution No. 5-2 | — | — | — | — | — | 180.5 |
| Electrolytic solution No. 5-3 | Synthesis Example 2 (5a-Tetra) | 0.14 | 0.14 | — | — | 155.1 |
| Electrolytic solution No. 5-4 | Synthesis Example 2 (5a-Tetra) | 0.14 | 0.14 | — | — | 155.4 |
| Electrolytic solution No. 5-5 | Synthesis Example 2 (5a-Tetra) | 0.14 | 0.14 | VC | 1.0 | 171.2 |
| Comparative electrolytic solution No. 1-1 | — | — | — | — | — | 100.0 |
| Comparative electrolytic solution No. 2-1 | — | — | — | — | — | 124.7 |
| Comparative electrolytic solution No. 2-2 | — | — | — | — | — | 177.3 |
| Comparative electrolytic solution No. 2-3 | (5a-Tetra) | 0.14 | — | — | — | 155.4 |
| Comparative electrolytic solution No. 3-1 | — | — | — | — | — | 125.0 |
| Comparative electrolytic solution No. 3-2 | — | — | — | — | — | 177.8 |
| Comparative electrolytic solution No. 3-3 | Synthesis Example 2 (5a-Tetra) | 0.14 | — | — | — | 155.9 |
| Comparative electrolytic solution No. 4-1 | — | — | — | — | — | 125.5 |
| Comparative electrolytic solution No. 4-2 | — | — | — | — | — | 178.5 |
| Comparative electrolytic solution No. 4-3 | Synthesis Example 2 (5a-Tetra) | 0.14 | — | — | — | 156.5 |
| Comparative electrolytic solution No. 4-4 | — | — | — | — | — | 125.5 |
| Comparative electrolytic solution No. 4-5 | — | — | — | — | — | 178.4 |
| Comparative electrolytic solution No. 4-6 | Synthesis Example 2 (5a-Tetra) | 0.14 | — | — | — | 156.4 |
| Comparative electrolytic solution No. 5-1 | — | — | — | — | — | 124.7 |
| Comparative electrolytic solution No. 5-2 | — | — | — | — | — | 177.4 |
| Comparative electrolytic solution No. 5-3 | Synthesis Example 2 (5a-Tetra) | 0.14 | — | — | — | 155.5 |

TABLE 4

| Electrolytic solution No. | Group (I) compound (Cis isomer) | Content (mass %) | Group (II) compound | Content (mass %) | Group (III) compound Trans isomer | Content (mass %) |
|---|---|---|---|---|---|---|
| Electrolytic solution No. 6-1 | Synthesis Example 1 (1a-Cis) | 1.0 | Butane-DMS | 1.0 | — | — |

TABLE 4-continued

| | | | | | | |
|---|---|---|---|---|---|---|
| Electrolytic solution No. 6-2 | Synthesis Example 1 (1a-Cis) | 1.0 | Butane-DMS | 1.0 | Synthesis Example 1 (1a-Trans) | 0.004 |
| Electrolytic solution No. 6-3 | Synthesis Example 1 (1a-Cis) | 1.0 | Butane-DMS | 1.0 | — | — |
| Electrolytic solution No. 6-4 | Synthesis Example 1 (1a-Cis) | 1.0 | Butane-DMS | 1.0 | Synthesis Example 1 (1a-Trans) | 0.004 |
| Electrolytic solution No. 6-5 | Synthesis Example 1 (1a-Cis) | 1.0 | Butane-DMS | 1.0 | Synthesis Example 1 (1a-Trans) | 0.004 |
| Electrolytic solution No. 7-1 | Synthesis Example 1 (1a-Cis) | 1.0 | 2-Butene-DMS | 1.0 | — | — |
| Electrolytic solution No. 7-2 | Synthesis Example 1 (1a-Cis) | 1.0 | 2-Butene-DMS | 1.0 | Synthesis Example 1 (1a-Trans) | 0.004 |
| Electrolytic solution No. 7-3 | Synthesis Example 1 (1a-Cis) | 1.0 | 2-Butene-DMS | 1.0 | — | — |
| Electrolytic solution No. 7-4 | Synthesis Example 1 (1a-Cis) | 1.0 | 2-Butene-DMS | 1.0 | Synthesis Example 1 (1a-Trans) | 0.004 |
| Electrolytic solution No. 7-5 | Synthesis Example 1 (1a-Cis) | 1.0 | 2-Butyne-DMS | 1.0 | Synthesis Example 1 (1a-Trans) | 0.004 |
| Electrolytic solution No. 7-6 | Synthesis Example 1 (1a-Cis) | 1.0 | 2-Butene-DMS | 1.0 | Synthesis Example 1 (1a-Trans) | 0.004 |
| Electrolytic solution No. 7-7 | Synthesis Example 1 (1a-Cis) | 1.0 | 2-Butyne-DMS | 1.0 | Synthesis Example 1 (1a-Trans) | 0.004 |
| Electrolytic solution No. 8-1 | Synthesis Example 1 (1a-Cis) | 1.0 | Formula (II-5a-1) | 1.0 | — | — |
| Electrolytic solution No. 8-2 | Synthesis Example 1 (1a-Cis) | 1.0 | Formula (II-5a-1) | 1.0 | Synthesis Example 1 (1a-Trans) | 0.004 |
| Electrolytic solution No. 8-3 | Synthesis Example 1 (1a-Cis) | 1.0 | Formula (II-5a-1) | 1.0 | — | — |
| Electrolytic solution No. 8-4 | Synthesis Example 1 (1a-Cis) | 1.0 | Formula (II-5a-1) | 1.0 | Synthesis Example 1 (1a-Trans) | 0.004 |
| Electrolytic solution No. 8-5 | Synthesis Example 1 (1a-Cis) | 1.0 | Formula (II-5a-1) | 1.0 | Synthesis Example 1 (1a-Trans) | 0.004 |
| Electrolytic solution No. 9-1 | Synthesis Example 1 (1a-Cis) | 1.0 | Succinonitrile | 1.0 | — | — |
| Electrolytic solution No. 9-2 | Synthesis Example 1 (1a-Cis) | 1.0 | Succinonitrile | 1.0 | Synthesis Example 1 (1a-Trans) | 0.004 |
| Electrolytic solution No. 9-3 | Synthesis Example 1 (1a-Cis) | 1.0 | Succinonitrile | 1.0 | — | — |
| Electrolytic solution No. 9-4 | Synthesis Example 1 (1a-Cis) | 1.0 | Succinonitrile | 1.0 | Synthesis Example 1 (1a-Trans) | 0.004 |
| Electrolytic solution No. 9-5 | Synthesis Example 1 (1a-Cis) | 1.0 | Succinonitrile | 1.0 | Synthesis Example 1 (1a-Trans) | 0.004 |
| Electrolytic solution No. 10-1 | Synthesis Example 1 (1a-Cis) | 1.0 | TMSP | 1.0 | — | — |
| Electrolytic solution No. 10-2 | Synthesis Example 1 (1a-Cis) | 1.0 | TMSP | 1.0 | Synthesis Example 1 (1a-Trans) | 0.004 |
| Electrolytic solution No. 10-3 | Synthesis Example 1 (1a-Cis) | 1.0 | TMSP | 1.0 | — | — |
| Electrolytic solution No. 10-4 | Synthesis Example 1 (1a-Cis) | 1.0 | TMSP | 1.0 | Synthesis Example 1 (1a-Trans) | 0.004 |
| Electrolytic solution No. 10-5 | Synthesis Example 1 (1a-Cis) | 1.0 | TMSP | 1.0 | Synthesis Example 1 (1a-Trans) | 0.004 |

TABLE 4-continued

| | | | | | |
|---|---|---|---|---|---|
| Electrolytic solution No. 11-1 | Synthesis Example 1 (1a-Cis) | 1.0 | TMSB | 1.0 | — | — |
| Electrolytic solution No. 11-2 | Synthesis Example 1 (1a-Cis) | 1.0 | TMSB | 1.0 | Synthesis Example 1 (1a-Trans) | 0.004 |
| Electrolytic solution No. 11-3 | Synthesis Example 1 (1a-Cis) | 1.0 | TMSB | 1.0 | — | — |
| Electrolytic solution No. 11-4 | Synthesis Example 1 (1a-Cis) | 1.0 | TMSB | 1.0 | Synthesis Example 1 (1a-Trans) | 0.004 |
| Electrolytic solution No. 11-5 | Synthesis Example 1 (1a-Cis) | 1.0 | TMSB | 1.0 | Synthesis Example 1 (1a-Trans) | 0.004 |
| Comparative electrolytic solution No. 1-1 | — | — | — | — | — | — |
| Comparative electrolytic solution No. 1-2 | Synthesis Example 1 (1a-Cis) | 1.0 | — | — | — | — |
| Comparative electrolytic solution No. 6-1 | — | — | Butane-DMS | 1.0 | — | — |
| Comparative electrolytic solution No. 6-2 | — | — | Butane-DMS | 1.0 | Synthesis Example 1 (1a-Trans) | 1.0 |
| Comparative electrolytic solution No. 6-3 | — | — | Butane-DMS | 1.0 | Synthesis Example 1 (1a-Trans) | 1.0 |
| Comparative electrolytic solution No. 7-1 | — | — | 2-Butene-DMS | 1.0 | — | — |
| Comparative electrolytic solution No. 7-2 | — | — | 2-Butene-DMS | 1.0 | Synthesis Example 1 (1a-Trans) | 1.0 |
| Comparative electrolytic solution No. 7-3 | — | — | 2-Butene-DMS | 1.0 | Synthesis Example 1 (1a-Trans) | 1.0 |
| Comparative electrolytic solution No. 7-4 | — | — | 2-Butyne-DMS | 1.0 | — | — |
| Comparative electrolytic solution No. 7-5 | — | — | 2-Butyne-DMS | 1.0 | Synthesis Example 1 (1a-Trans) | 1.0 |
| Comparative electrolytic solution No. 7-6 | — | — | 2-Butyne-DMS | 1.0 | Synthesis Example 1 (1a-Trans) | 1.0 |
| Comparative electrolytic solution No. 8-1 | — | — | Formula (II-5a-1) | 1.0 | — | — |
| Comparative electrolytic solution No. 8-2 | — | — | Formula (II-5a-1) | 1.0 | Synthesis Example 1 (1a-Trans) | 1.0 |
| Comparative electrolytic solution No. 8-3 | — | — | Formula (II-5a-1) | 1.0 | Synthesis Example 1 (1a-Trans) | 1.0 |
| Comparative electrolytic solution No. 9-1 | — | — | Succinonitrile | 1.0 | — | — |
| Comparative electrolytic solution No. 9-2 | — | — | Succinonitrile | 1.0 | Synthesis Example 1 (1a-Trans) | 1.0 |
| Comparative electrolytic solution No. 9-3 | — | — | Succinonitrile | 1.0 | Synthesis Example 1 (1a-Trans) | 1.0 |
| Comparative electrolytic solution No. 10-1 | — | — | TMSP | 1.0 | — | — |
| Comparative electrolytic solution No. 10-2 | — | — | TMSP | 1.0 | Synthesis Example 1 (1a-Trans) | 1.0 |
| Comparative electrolytic solution No. 10-3 | — | — | TMSP | 1.0 | Synthesis Example 1 (1a-Trans) | 1.0 |
| Comparative electrolytic solution No. 11-1 | — | — | TMSB | 1.0 | — | — |
| Comparative electrolytic solution No. 11-2 | — | — | TMSB | 1.0 | Synthesis Example 1 (1a-Trans) | 1.0 |
| Comparative electrolytic solution No. 11-3 | — | — | TMSB | 1.0 | Synthesis Example 1 (1a-Trans) | 1.0 |

TABLE 4-continued

| Electrolytic solution No, | Trans isomer/ Cis isomer (mass ratio) | Group (IV) compound Tetrafluoro complex | Content (mass %) | Tetrafluoro complex/ Cis isomer (mass ratio) | Group (V) compound | Content (mass %) |
|---|---|---|---|---|---|---|
| Electrolytic solution No. 6-1 | — | — | — | — | — | — |
| Electrolytic solution No. 6-2 | 0.004 | — | — | — | — | — |
| Electrolytic solution No. 6-3 | — | Synthesis Example 2 (5a-Tetra) | 0.14 | 0.14 | — | — |
| Electrolytic solution No. 6-4 | 0.004 | Synthesis Example 2 (5a-Tetra) | 0.14 | 0.14 | — | — |
| Electrolytic solution No. 6-5 | 0.004 | Synthesis Example 2 (5a-Tetra) | 0.14 | 0.14 | VC | 1.0 |
| Electrolytic solution No. 7-1 | — | — | — | — | — | — |
| Electrolytic solution No. 7-2 | 0.004 | — | — | — | — | — |
| Electrolytic solution No. 7-3 | — | Synthesis Example 2 (5a-Tetra) | 0.14 | 0.14 | — | — |
| Electrolytic solution No. 7-4 | 0.004 | Synthesis Example 2 (5a-Tetra) | 0.14 | 0.14 | — | — |
| Electrolytic solution No. 7-5 | 0.004 | Synthesis Example 2 (5a-Tetra) | 0.14 | 0.14 | — | — |
| Electrolytic solution No. 7-6 | 0.004 | Synthesis Example 2 (5a-Tetra) | 0.14 | 0.14 | VC | 1.0 |
| Electrolytic solution No. 7-7 | 0.004 | Synthesis Example 2 (5a-Tetra) | 0.14 | 0.14 | VC | 1.0 |
| Electrolytic solution No. 8-1 | — | — | — | — | — | — |
| Electrolytic solution No. 8-2 | 0.004 | — | — | — | — | — |
| Electrolytic solution No. 8-3 | — | Synthesis Example 2 (5a-Tetra) | 0.14 | 0.14 | — | — |
| Electrolytic solution No. 8-4 | 0.004 | Synthesis Example 2 (5a-Tetra) | 0.14 | 0.14 | — | — |
| Electrolytic solution No. 8-5 | 0.004 | Synthesis Example 2 (5a-Tetra) | 0.14 | 0.14 | VC | 1.0 |
| Electrolytic solution No. 9-1 | — | — | — | — | — | — |
| Electrolytic solution No. 9-2 | 0.004 | — | — | — | — | — |
| Electrolytic solution No. 9-3 | — | Synthesis Example 2 (5a-Tetra) | 0.14 | 0.14 | — | — |
| Electrolytic solution No. 9-4 | 0.004 | Synthesis Example 2 (5a-Tetra) | 0.14 | 0.14 | — | — |
| Electrolytic solution No. 9-5 | 0.004 | Synthesis Example 2 (5a-Tetra) | 0.14 | 0.14 | VC | 1.0 |
| Electrolytic solution No. 10-1 | — | — | — | — | — | — |
| Electrolytic solution No. 10-2 | 0.004 | — | — | — | — | — |
| Electrolytic solution No. 10-3 | — | Synthesis Example 2 (5a-Tetra) | 0.14 | 0.14 | — | — |
| Electrolytic solution No. 10-4 | 0.004 | Synthesis Example 2 (5a-Tetra) | 0.14 | 0.14 | — | — |
| Electrolytic solution No. 10-5 | 0.004 | Synthesis Example 2 (5a-Tetra) | 0.14 | 0.14 | VC | 1.0 |
| Electrolytic solution No. 11-1 | — | — | — | — | — | — |
| Electrolytic solution No. 11-2 | 0.004 | — | — | — | — | — |
| Electrolytic solution No. 11-3 | — | Synthesis Example 2 (5a-Tetra) | 0.14 | 0.14 | — | — |
| Electrolytic solution No. 11-4 | 0.004 | Synthesis Example 2 (5a-Tetra) | 0.14 | 0.14 | — | — |
| Electrolytic solution No. 11-5 | 0.004 | Synthesis Example 2 (5a-Tetra) | 0.14 | 0.14 | VC | 1.0 |

TABLE 4-continued

| | | | | | | |
|---|---|---|---|---|---|---|
| Comparative electrolytic solution No. 1-1 | — | — | — | — | — | — |
| Comparative electrolytic solution No. 1-2 | — | — | — | — | — | — |
| Comparative electrolytic solution No. 6-1 | — | — | — | — | — | — |
| Comparative electrolytic solution No. 6-2 | — | — | — | — | — | — |
| Comparative electrolytic solution No. 6-3 | — | Synthesis Example 2 (5a-Tetra) | 0.14 | — | — | — |
| Comparative electrolytic solution No. 7-1 | — | — | — | — | — | — |
| Comparative electrolytic solution No. 7-2 | — | — | — | — | — | — |
| Comparative electrolytic solution No. 7-3 | — | Synthesis Example 2 (5a-Tetra) | 0.14 | — | — | — |
| Comparative electrolytic solution No. 7-4 | — | — | — | — | — | — |
| Comparative electrolytic solution No. 7-5 | — | — | — | — | — | — |
| Comparative electrolytic solution No. 7-6 | — | Synthesis Example 2 (5a-Tetra) | 0.14 | — | — | — |
| Comparative electrolytic solution No. 8-1 | — | — | — | — | — | — |
| Comparative electrolytic solution No. 8-2 | — | — | — | — | — | — |
| Comparative electrolytic solution No. 8-3 | — | Synthesis Example 2 (5a-Tetra) | 0.14 | — | — | — |
| Comparative electrolytic solution No. 9-1 | — | — | — | — | — | — |
| Comparative electrolytic solution No. 9-2 | — | — | — | — | — | — |
| Comparative electrolytic solution No. 9-3 | — | Synthesis Example 2 (5a-Tetra) | 0.14 | — | — | — |
| Comparative electrolytic solution No. 10-1 | — | — | — | — | — | — |
| Comparative electrolytic solution No. 10-2 | — | — | — | — | — | — |
| Comparative electrolytic solution No. 10-3 | — | Synthesis Example 2 (5a-Tetra) | 0.14 | — | — | — |
| Comparative electrolytic solution No. 11-1 | — | — | — | — | — | — |
| Comparative electrolytic solution No. 11-2 | — | — | — | — | — | — |
| Comparative electrolytic solution No. 11-3 | — | Synthesis Example 2 (5a-Tetra) | 0.14 | — | — | — |

In Tables 3 and 4, 1,3-PRS means 1,3-propenesultone. 1,4-BTS means 1,4-butenesultone. Butane-DMS means 1,4-butanediol dimethanesulfonate. Propane-DMS means 1,3-propanediol dimethanesulfonate. 2-Butene-DMS means 2-butene-1,4-diol dimethanesulfonate. 2-Butene-DES means 2-butene-1,4-diol diethanesulfonate. 2-Butyne-DMS means 2-butyne-1,4-diol dimethanesulfonate. TMSP means tris(trimethylsilyl) phosphate. TMSB means tris(trimethylsilyl) borate.

TABLE 5

| | Electrolytic solution No. | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 2-4 | Electrolytic solution No. 2-4 | 134.7 | 128.1 | 125.1 |
| Example 2-13 | Electrolytic solution No. 2-13 | 136.9 | 128.6 | 125.7 |
| Example 2-16 | Electrolytic solution No. 2-16 | 137.1 | 129.0 | 125.9 |
| Example 2-21 | Electrolytic solution No. 2-21 | 137.4 | 130.5 | 126.4 |
| Example 2-33 | Electrolytic solution No. 2-33 | 140.8 | 133.8 | 129.6 |
| Example 3-4 | Electrolytic solution No. 3-4 | 134.0 | 128.8 | 125.0 |
| Example 3-13 | Electrolytic solution No. 3-13 | 136.2 | 129.3 | 125.6 |
| Example 3-16 | Electrolytic solution No. 3-16 | 136.4 | 129.7 | 125.8 |
| Example 3-21 | Electrolytic solution No. 3-21 | 136.7 | 131.3 | 126.3 |
| Example 3-33 | Electrolytic solution No. 3-33 | 140.1 | 134.6 | 129.4 |
| Example 4-4 | Electrolytic solution No. 4-4 | 134.3 | 129.0 | 125.2 |

TABLE 5-continued

| Electrolytic solution No, | | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 4-12 | Electrolytic solution No.4-12 | 133.9 | 128.4 | 124.6 |
| Example 4-14 | Electrolytic solution No.4-14 | 136.5 | 129.5 | 125.8 |
| Example 12-1 | Electrolytic solution No.12-1 | 136.2 | 128.8 | 125.3 |
| Example 4-17 | Electrolytic solution No.4-17 | 136.7 | 129.9 | 126.0 |
| Example 4-22 | Electrolytic solution No.4-22 | 137.0 | 131.5 | 126.5 |
| Example 4-27 | Electrolytic solution No.4-27 | 136.4 | 129.2 | 125.4 |
| Example 4-32 | Electrolytic solution No.4-32 | 136.7 | 130.8 | 125.9 |
| Example 4-41 | Electrolytic solution No.4-41 | 140.4 | 134.7 | 129.7 |
| Example 12-2 | Electrolytic solution No.12-2 | 140.1 | 134.1 | 129.2 |
| Example 5-4 | Electrolytic solution No.5-4 | 133.9 | 128.2 | 124.7 |
| Example 5-13 | Electrolytic solution No.5-13 | 136.1 | 128.7 | 125.3 |
| Example 5-16 | Electrolytic solution No.5-16 | 136.3 | 129.1 | 125.5 |
| Example 5-21 | Electrolytic solution No.5-21 | 136.6 | 130.7 | 126.0 |
| Example 5-30 | Electrolytic solution No.5-30 | 140.0 | 133.9 | 129.2 |
| Comparative Example 1-1 | Comparative electrolytic solution No.1-1 | 100.0 | 100.0 | 100.0 |
| Comparative Example 2-1 | Comparative electrolytic solution No.2-1 | 121.2 | 112.6 | 109.6 |
| Comparative Example 2-2 | Comparative electrolytic solution No. 2-2 | 125.6 | 118.7 | 117.3 |
| Comparative Example 2-3 | Comparative electrolytic solution No.2-3 | 127.7 | 119.6 | 117.6 |
| Comparative Example 3-1 | Comparative electrolytic solution No.3-1 | 120.6 | 113.2 | 109.5 |
| Comparative Example 3-2 | Comparative electrolytic solution No.3-2 | 125.0 | 119.4 | 117.2 |
| Comparative Example 3-3 | Comparative electrolytic solution No.3-3 | 127.1 | 120.3 | 117.5 |
| Comparative Example 4-1 | Comparative electrolytic solution No.4-1 | 120.9 | 113.3 | 109.7 |
| Comparative Example 4-2 | Comparative electrolytic solution No.4-2 | 125.3 | 119.6 | 117.4 |
| Comparative Example 4-3 | Comparative electrolytic solution No.4-3 | 127.3 | 120.4 | 117.7 |
| Comparative Example 4-4 | Comparative electrolytic solution No.4-4 | 120.7 | 112.8 | 109.3 |
| Comparative Example 4-5 | Comparative electrolytic solution No.4-5 | 125.1 | 116.8 | 116.9 |
| Comparative Example 4-6 | Comparative electrolytic solution No.4-6 | 127.1 | 117.0 | 117.3 |
| Comparative Example 5-1 | Comparative electrolytic solution No.5-1 | 120.5 | 112.7 | 109.3 |
| Comparative Example 5-2 | Comparative electrolytic solution No.5-2 | 124.9 | 118.8 | 116.9 |
| Comparative Example 5-3 | Comparative electrolytic solution No.5-3 | 127.0 | 116.9 | 117.3 |

(Positive electrode: NMC, negative electrode: graphite)

TABLE 6

| | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 6-1 | Electrolytic solution No.6-1 | 133.8 | 127.8 | 124.7 |
| Example 6-2 | Electrolytic solution No.6-2 | 135.9 | 128.4 | 125.1 |
| Example 6-3 | Electrolytic solution No.6-3 | 136.1 | 128.8 | 125.3 |
| Example 6-4 | Electrolytic solution No.6-4 | 136.4 | 130.4 | 125.8 |
| Example 6-5 | Electrolytic solution No.6-5 | 139.8 | 133.7 | 128.9 |
| Example 7-1 | Electrolytic solution No.7-1 | 133.6 | 127.7 | 124.3 |
| Example 7-2 | Electrolytic solution No.7-2 | 135.6 | 128.3 | 124.8 |
| Example 7-3 | Electrolytic solution No.7-3 | 135.8 | 128.7 | 125.0 |
| Example 7-4 | Electrolytic solution No.7-4 | 136.1 | 130.3 | 125.5 |
| Example 7-5 | Electrolytic solution No.7-5 | 136.5 | 130.5 | 125.7 |
| Example 7-6 | Electrolytic solution No.7-6 | 139.5 | 133.5 | 128.7 |
| Example 7-7 | Electrolytic solution No.7-7 | 139.9 | 133.8 | 128.8 |
| Example 8-1 | Electrolytic solution No.8-1 | 133.5 | 128.1 | 124.3 |
| Example 8-2 | Electrolytic solution No.8-2 | 135.8 | 128.8 | 124.9 |
| Example 8-3 | Electrolytic solution No.8-3 | 136.0 | 129.2 | 125.1 |
| Example 8-4 | Electrolytic solution No.8-4 | 136.3 | 130.8 | 125.6 |
| Example 8-5 | Electrolytic solution No.8-5 | 139.7 | 134.1 | 128.8 |
| Example 9-1 | Electrolytic solution No.9-1 | 133.4 | 127.6 | 124.2 |
| Example 9-2 | Electrolytic solution No.9-2 | 135.5 | 128.3 | 124.7 |

TABLE 6-continued

| | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 9-3 | Electrolytic solution No.9-3 | 135.7 | 128.7 | 124.9 |
| Example 9-4 | Electrolytic solution No.9-4 | 136.0 | 130.3 | 125.4 |
| Example 9-5 | Electrolytic solution No.9-5 | 139.4 | 133.5 | 128.5 |
| Example 10-1 | Electrolytic solution No.10-1 | 133.4 | 127.4 | 124.0 |
| Example 10-2 | Electrolytic solution No.10-2 | 135.2 | 128.0 | 124.3 |
| Example 10-3 | Electrolytic solution No.10-3 | 135.4 | 128.4 | 124.5 |
| Example 10-4 | Electrolytic solution No.10-4 | 135.7 | 130.0 | 125.0 |
| Example 10-5 | Electrolytic solution No.10-5 | 139.1 | 133.3 | 128.1 |
| Example 11-1 | Electrolytic solution No 11-1 | 133.3 | 127.2 | 123.9 |
| Example 11-2 | Electrolytic solution No.11-2 | 135.1 | 127.9 | 124.4 |
| Example 11-3 | Electrolytic solution No.11-3 | 135.3 | 128.3 | 124.6 |
| Example 11-4 | Electrolytic solution No.11-4 | 135.6 | 129.9 | 125.1 |
| Example 11-5 | Electrolytic solution No.11-5 | 139.0 | 133.1 | 128.3 |
| Comparative Example 1-1 | Comparative electrolytic solution No.1-1 | 100.0 | 100.0 | 100.0 |
| Comparative Example 1-2 | Comparative electrolytic solution No.1-2 | 125.1 | 117.8 | 114.9 |
| Comparative Example 6-1 | Comparative electrolytic solution No.6-1 | 120.4 | 112.4 | 109.1 |
| Comparative Example 6-2 | Comparative electrolytic solution No.6-2 | 124.2 | 114.9 | 115.2 |
| Comparative Example 6-3 | Comparative electrolytic solution No.6-3 | 126.8 | 116.7 | 117.0 |
| Comparative Example 7-1 | Comparative electrolytic solution No.7-1 | 120.2 | 112.3 | 108.9 |
| Comparative Example 7-2 | Comparative electrolytic solution No.7-2 | 123.8 | 114.9 | 114.9 |
| Comparative Example 7-3 | Comparative electrolytic solution No.7-3 | 126.6 | 116.5 | 116.8 |
| Comparative Example 7-4 | Comparative electrolytic solution No.7-4 | 120.5 | 112.5 | 109.0 |
| Comparative Example 7-5 | Comparative electrolytic solution No.7-5 | 124.0 | 115.1 | 115.4 |
| Comparative Example 7-6 | Comparative electrolytic solution No.7-6 | 126.9 | 116.8 | 117.0 |
| Comparative Example 8-1 | Comparative electrolytic solution No.8-1 | 120.3 | 112.8 | 109.0 |
| Comparative Example 8-2 | Comparative electrolytic solution No.8-2 | 124.6 | 115.2 | 115.5 |
| Comparative Example 8-3 | Comparative electrolytic solution No.8-3 | 126.7 | 117.0 | 116.9 |
| Comparative Example 9-1 | Comparative electrolytic solution No.9-1 | 120.0 | 112.3 | 108.7 |
| Comparative Example 9-2 | Comparative electrolytic solution No.9-2 | 124.1 | 114.7 | 115.2 |
| Comparative Example 9-3 | Comparative electrolytic solution No.9-3 | 126.4 | 116.5 | 116.7 |
| Comparative Example 10-1 | Comparative electrolytic solution No.10-1 | 119.8 | 112.1 | 108.4 |
| Comparative Example 10-2 | Comparative electrolytic solution No.10-2 | 124.2 | 114.3 | 114.7 |
| Comparative Example 10-3 | Comparative electrolytic solution No.10-3 | 126.2 | 116.3 | 116.3 |
| Comparative Example 11-1 | Comparative electrolytic solution No.11-1 | 119.7 | 112.0 | 108.5 |
| Comparative Example 11-2 | Comparative electrolytic solution No.11-2 | 123.9 | 114.4 | 114.8 |
| Comparative Example 11-3 | Comparative electrolytic solution No.11-3 | 126.1 | 116.2 | 116.5 |

(Positive electrode: NMC, negative electrode: graphite)

The results shown in Tables 3 to 6 demonstrated that Examples 2 and 3 which included the above group (I) and group (II) compounds as essential ingredients of the non-aqueous electrolytic solution according to the present invention were excellent in various evaluation results as compared with Comparative Example 1-1 in which none of them was included, Comparative Examples 2-1 to 2-3 and 3-1 to 3-3 in which the group (I) compound among these was not included, and Comparative Examples 1-2 and 1-3 in which the group (II) compound among these was not included.

Combined Addition of Group (I) and (II) Compounds

For example, Examples 2-1 and 3-1 in which the difluoro ionic complex in the cis configuration (1a-Cis) from Synthesis Example 1 and 1,3-PRS or the compound represented by the formula (II-2a-4) were included were excellent in various evaluation results as compared with Comparative Example 1-1 in which neither the above ionic complex nor 1,3-PRS or the formula (II-2a-4) was included, Comparative Example 1-2 in which only (1a-Cis) among these was included, Comparative Example 2-1 in which only 1,3-PRS among these was included, and Comparative Example 3-1 in which only the compound represented by the formula (II-2a-4) among these was included.

This can be explained as described above: when the difluoro ionic complex (1a-Cis) and cyclic sulfonic acid ester having an unsaturated bonds such as 1,3-PRS (or cyclic sulfuric acid ester such as the compound represented by the formula (II-2a-4)) were contained in the nonaqueous electrolytic solution according to the present invention, these additives undergo reductive decomposition on the negative electrode in this order of the above (1a-Cis) and then 1,3-PRS (or the compound represented by the formula (II-2a-4)), forming a stable film (SEI) on the surface of the negative electrode. This reaction film layer having a high ion conductivity, and the SEI having long-term stability and covering the surface of the negative electrode can prevent side reactions such as decomposition of a solvent which otherwise occur on the surface of the negative electrode. This, in turn, can reduce the initial irreversible capacity of the nonaqueous electrolytic solution battery, and also improve long-term durability and output characteristics. Moreover, 1,3-RPS (or the compound represented by the formula (II-2a-4)) also appears to form a film in the positive electrode side, enabling reduced oxidative decomposition of a nonaqueous solvent in the positive electrode side under a high-temperature environment.

Moreover, comparison of Example 2-1 with Comparative Example 2-2 and comparison of Example 2-3 with Comparative Example 2-3 reveled that the nonaqueous electrolytic solution battery including the difluoro ionic complex in the cis configuration (1a-Cis) and 1,3-PRS showed higher effects than the nonaqueous electrolytic solution battery including the difluoro ionic complex in the trans configuration (1a-Trans) and 1,3-PRS. Similarly, comparison of Example 3-1 with Comparative Example 3-2 and comparison of Example 3-3 with Comparative Example 3-3 reveled that the nonaqueous electrolytic solution battery including the above (1a-Cis) and the compound represented by the formula (II-2a-4) showed better effects than the nonaqueous electrolytic solution battery including the above (1a-Trans)

and the compound represented by the formula (II-2a-4). This can be explained as follows: the reductive decomposition reaction of (1a-Cis) in the cis conformation and (1a-Trans) in the trans conformation progresses in different rates. This changes the selectivity of the reductive decomposition reaction (the presence or absence of solvent decomposition), which, in turn, changes the main component of the resulting SEI. Therefore, this differently generated final SEI leads to different improving effects on the battery performance.

A similar tendency as described above was also observed for Example 3-1 in which the contents of the difluoro ionic complex (1a-Cis) and the compound represented by the formula (II-2a-4) were each changed.

Further Addition of Group (III) Compound

Examples 2-2 (or Example 3-2) including a nonaqueous electrolytic solution containing the difluoro ionic complex in the cis configuration (1a-Cis) and 1,3-PRS (or the compound represented by the formula (II-2a-4)) as well as the difluoro ionic complex in the trans configuration (1a-Trans) was found to have a tendency to further improve the discharge capacity (0° C.) after stored at 60° C. without deteriorating the discharge capacity (0° C.) after prolonged cycles at 60° C. as compared with the nonaqueous electrolytic solution battery ((Example 2-1 (or Example 3-1)) including the above (1a-Cis), 1,3-PRS (or the compound represented by the formula (II-2a-4)).

Moreover, even when (5a-Tetra) as the group (IV) compound was included, further inclusion of the difluoro ionic complex in the trans conformation (1a-Trans) was found to have a tendency to further improve the discharge capacity (0° C.) after stored at 60° C. without impairing the discharge capacity (0° C.) after prolonged cycles at 60° C. (for example, comparison of Example 2-4 with Example 2-3, and comparison of Example 3-4 with Example 3-3).

Further Addition of Group (IV) Compound

Examples 2-3 (or Example 3-3) including a nonaqueous electrolytic solution containing the difluoro ionic complex (1a-Cis) and 1,3-PRS (or the compound represented by the formula (II-2a-4)) as well as the difluoro ionic complex (5a-Tetra) was found to have a tendency to further reduce the gas yield during storage of the electrolytic solution without deteriorating the discharge capacity (0° C.) after prolonged cycles at 60° C., the 5C-rate characteristic (25° C.), and the discharge capacity (0° C.) after stored at 60° C. as compared with the nonaqueous electrolytic solution battery ((Example 2-1 (or Example 3-1)) including the above (1a-Cis) and 1,3-PRS (or the compound represented by the formula (II-2a-4)).

Further Addition of Group (V) Compound

Examples 2-5 (or Example 3-5) including a nonaqueous electrolytic solution containing the difluoro ionic complex in the cis configuration (1a-Cis) from Synthesis Example 1, 1,3-PRS (or the compound represented by the formula (II-2a-4)), the difluoro ionic complex in the trans configuration (1a-Trans) from Synthesis Example 1, and the tetrafluoro ionic complex (5a-Tetra) from Synthesis Example 2 as well as the group (V) such as VC, VEC, EEC, and FEC was found to have a tendency to improve the discharge capacity (0° C.) after prolonged cycles at 60° C., the 5C-rate characteristic (25° C.), and the discharge capacity (0° C.) after stored at 60° C. depending on the addition amount of the group (V) as compared with the nonaqueous electrolytic solution battery (Example 2-4 (or Example 3-4)) including the above (1a-Cis), 1,3-PRS (or the compound represented by the formula (II-2a-4)), the above (1a-Trans), and the above (5a-Tetra).

The results shown in Tables 5 and 6 demonstrated that Examples 4 to 11 which included the above group (I) and group (II) compounds as essential ingredients of the nonaqueous electrolytic solution according to the present invention were excellent in various evaluation results as compared with Comparative Example 1-1 in which none of them was included, Comparative Examples 4 to 11 in which the group (I) compound among these was not included, and Comparative Examples 1-2 and 1-3 in which the group (II) compound amount these was not included.

Example 12—Positive Electrode

NCA Positive Electrode

A test NCA positive electrode was produced in accordance with the following procedure using a lithium-nickel-cobalt-aluminum composite oxide, $LiNi_{0.85}Co_{0.10}Al_{0.05}O_2$ (NCA) powder instead of the positive-electrode active material (NMC) used in the nonaqueous electrolytic solution batteries according to Example 1 as described above.

Production of NCA Positive Electrode

A $LiNi_{0.85}Co_{0.10}Al_{0.05}O_2$ (NCA) powder (Todakogyo Corp.) and acetylene black (electrically conductive agent) were dry-mixed, and uniformly dispersed and mixed into NMP where PVDF as a binding agent was pre-dissolved, and NMP for adjusting the viscosity was further added to prepare a NCA mixture paste. The resulting paste was applied to an aluminum foil (current collector), dried, and pressurized. Then the aluminum foil was processed into a predetermined size to obtain a test NCA positive electrode. The ratio of solid contents in the positive electrode was NCA:electrically conductive agent:PVDF=85:5:10 (by the mass ratio).

Production of Nonaqueous Electrolytic Solution Batteries

Aluminum laminate housing cells (with a capacity of 30 mAh) including the above test NCA positive electrode, the test graphite negative electrode, and a cellulose separator were each impregnated with one of the various nonaqueous electrolytic solutions and the various comparative nonaqueous electrolytic solutions shown in Table 7 to produce the nonaqueous electrolytic solution batteries according to Examples 12-1 to 12-8 and Comparative Examples 12-1 to 12-10. It is noted that Table 7 summarizes the compositions of the above electrolytic solutions.

TABLE 7

| Electrolytic solution No. | Electrolytic solution No. | Group (I) compound (Cis isomer) | Content (mass %) | Group (II) compound | Content (mass %) | Group (III) compound Trans isomer | Content (mass %) |
|---|---|---|---|---|---|---|---|
| Electrolytic solution No. 1-21 | Electrolytic solution No. 1-21 | Synthesis Example 1 (1a-Cis) | 1.0 | 1,3-PS | 2.0 | Synthesis Example 1 (1a-Trans) | 0.004 |

TABLE 7-continued

| Electrolytic solution No. | Electrolytic solution No. | | | | | | |
|---|---|---|---|---|---|---|---|
| Electrolytic solution No. 2-21 | Electrolytic solution No. 2-4 | Synthesis Example 1 (1a-Cis) | 1.0 | 1,3-PRS | 1.0 | Synthesis Example 1 (1a-Trans) | 0.004 |
| Electrolytic solution No. 3-21 | Electrolytic solution No. 3-4 | Synthesis Example 1 (1a-Cis) | 1.0 | Formula (II-2a-4) | 1.0 | Synthesis Example 1 (1a-Trans) | 0.004 |
| Electrolytic solution No. 4-22 | Electrolytic solution No. 4-6 | Synthesis Example 1 (1a-Cis) | 1.0 | Formula (II-3a-1) | 1.0 | Synthesis Example 1 (1a-Trans) | 0.004 |
| Electrolytic solution No. 5-21 | Electrolytic solution No. 5-4 | Synthesis Example 1 (1a-Cis) | 1.0 | Formula (II-3a-15) | 1.0 | Synthesis Example 1 (1a-Trans) | 0.004 |
| Electrolytic solution No. 6-16 | Electrolytic solution No. 6-4 | Synthesis Example 1 (1a-Cis) | 1.0 | Butane-DMS | 1.0 | Synthesis Example 1 (1a-Trans) | 0.004 |
| Electrolytic solution No. 9-16 | Electrolytic solution No. 9-4 | Synthesis Example 1 (1a-Cis) | 1.0 | Succinonitrile | 1.0 | Synthesis Example 1 (1a-Trans) | 0.004 |
| Electrolytic solution No. 4-32 | Electrolytic solution No. 4-8 | Synthesis Example 1 (1a-Cis) | 1.0 | Formula (II-3b-1) | 1.0 | Synthesis Example 1 (1a-Trans) | 0.004 |
| Comparative electrolytic solution No. 1-1 | Comparative electrolytic solution No. 1-1 | — | — | — | — | — | — |
| Comparative electrolytic solution No. 1-2 | Comparative electrolytic solution No. 1-2 | Synthesis Example 1 (1a-Cis) | 1.0 | — | — | — | — |
| Comparative electrolytic solution No. 1-6 | Comparative electrolytic solution No. 1-6 | — | — | 1,3-PS | 2.0 | Synthesis Example 1 (1a-Trans) | 1.0 |
| Comparative electrolytic solution No. 2-3 | Comparative electrolytic solution No. 2-3 | — | — | 1,3-PRS | 1.0 | Synthesis Example 1 (1a-Trans) | 1.0 |
| Comparative electrolytic solution No. 3-3 | Comparative electrolytic solution No. 3-3 | — | — | Formula (II-2a-4) | 1.0 | Synthesis Example 1 (1a-Trans) | 1.0 |
| Comparative electrolytic solution No. 4-3 | Comparative electrolytic solution No. 4-3 | — | — | Formula (II-3a-1) | 1.0 | Synthesis Example 1 (1a-Trans) | 1.0 |
| Comparative electrolytic solution No. 5-3 | Comparative electrolytic solution No. 5-3 | — | — | Formula (II-3a-15) | 1.0 | Synthesis Example 1 (1a-Trans) | 1.0 |
| Comparative electrolytic solution No. 6-3 | Comparative electrolytic solution No. 6-3 | — | — | Butane-DMS | 1.0 | Synthesis Example 1 (1a-Trans) | 1.0 |
| Comparative electrolytic solution No. 9-3 | Comparative electrolytic solution No. 9-3 | — | — | Succinonitrile | 1.0 | Synthesis Example 1 (1a-Trans) | 1.0 |
| Comparative electrolytic solution No. 4-6 | Comparative electrolytic solution No. 4-6 | — | — | Formula (II-3b-1) | 1.0 | Synthesis Example 1 (1a-Trans) | 1.0 |

| Electrolytic solution No, | Electrolytic solution No, | Trans isomer/ Cis isomer (mass ratio) | Group (IV) compound Tetrafluoro complex | Content (mass %) | Tetrafluoro complex/ Cis isomer (mass ratio) | Group (V) compound | Content (mass %) |
|---|---|---|---|---|---|---|---|
| Electrolytic solution No. 1-21 | Electrolytic solution No. 1-21 | 0.004 | Synthesis Example 2 (5a-Tetra) | 0.14 | 0.14 | — | — |
| Electrolytic solution No. 2-21 | Electrolytic solution No. 2-4 | 0.004 | Synthesis Example 2 (5a-Tetra) | 0.14 | 0.14 | — | — |
| Electrolytic solution No. 3-21 | Electrolytic solution No. 3-4 | 0.004 | Synthesis Example 2 (5a-Tetra) | 0.14 | 0.14 | — | — |
| Electrolytic solution No. 4-22 | Electrolytic solution No. 4-6 | 0.004 | Synthesis Example 2 (5a-Tetra) | 0 14 | 0.14 | — | — |
| Electrolytic solution No. 5-21 | Electrolytic solution No. 5-4 | 0.004 | Synthesis Example 2 (5a-Tetra) | 0.14 | 0.14 | — | — |
| Electrolytic solution No. 6-16 | Electrolytic solution No. 6-4 | 0.004 | Synthesis Example 2 (5a-Tetra) | 0.14 | 0.14 | — | — |
| Electrolytic solution No. 9-16 | Electrolytic solution No. 9-4 | 0.004 | Synthesis Example 2 (5a-Tetra) | 0.14 | 0.14 | — | — |

TABLE 7-continued

| Electrolytic solution No. 4-32 | Electrolytic solution No. 4-8 | 0.004 | Synthesis Example 2 (5a-Tetra) | 0.14 | 0.14 | — | — |
|---|---|---|---|---|---|---|---|
| Comparative electrolytic solution No. 1-1 | Comparative electrolytic solution No. 1-1 | — | — | — | — | — | — |
| Comparative electrolytic solution No. 1-2 | Comparative electrolytic solution No. 1-2 | — | — | — | — | — | — |
| Comparative electrolytic solution No. 1-6 | Comparative electrolytic solution No. 1-6 | — | Synthesis Example 2 (5a-Tetra) | 0.14 | — | — | — |
| Comparative electrolytic solution No. 2-3 | Comparative electrolytic solution No. 2-3 | — | Synthesis Example 2 (5a-Tetra) | 0.14 | — | — | — |
| Comparative electrolytic solution No. 3-3 | Comparative electrolytic solution No. 3-3 | — | Synthesis Example 2 (5a-Tetra) | 0.14 | — | — | — |
| Comparative electrolytic solution No. 4-3 | Comparative electrolytic solution No. 4-3 | — | Synthesis Example 2 (5a-Tetra) | 0.14 | — | — | — |
| Comparative electrolytic solution No. 5-3 | Comparative electrolytic solution No. 5-3 | — | Synthesis Example 2 (5a-Tetra) | 0.14 | — | — | — |
| Comparative electrolytic solution No. 6-3 | Comparative electrolytic solution No. 6-3 | — | Synthesis Example 2 (5a-Tetra) | 0.14 | — | — | — |
| Comparative electrolytic solution No. 9-3 | Comparative electrolytic solution No. 9-3 | — | Synthesis Example 2 (5a-Tetra) | 0.14 | — | — | — |
| Comparative electrolytic solution No. 4-6 | Comparative electrolytic solution No. 4-6 | — | Synthesis Example 2 (5a-Tetra) | 0.14 | — | — | — |

Example 12 and Comparative Example 12

Evaluation of Test Cells
Evaluation 1: Low-Temperature Property (0° C.) after 500 Cycles at 60° C.

Each of the nonaqueous electrolytic solution batteries according to Example 12 and Comparative Example 12 was evaluated as in Evaluation 1 performed for the nonaqueous electrolytic solution battery according to Example 1-1. However, the charge upper limit voltage was changed to 4.2 V from 4.3 V for the initial charge and discharge and the charge-and-discharge cycles as conditioning at an environmental temperature of 25° C. Further, the charge upper limit voltage was changed from 4.3 V to 4.2 V upon performing 500 cycles at an environmental temperature of 60° C. after this conditioning. Moreover, constant-current and constant-voltage charge performed to 4.3 V at 0° C. and a 0.2 C rate was changed to constant-current and constant-voltage charge to 4.2 V. A capacity obtained at this time was considered as the low-temperature property (0° C.) after prolonged cycles at 60° C.

Evaluation 2: 5C-Rate Characteristic after 500 Cycles at 60° C.

Each of the nonaqueous electrolytic solution batteries according to Example 12 and Comparative Example 12 was evaluated for the 5C-rate characteristic after 500 cycles at 60° C. as in Evaluation 2 preformed for the nonaqueous electrolytic solution battery according to Example 1-1. However, constant-current and constant-voltage charge performed to 4.3 V at 25° C. and a 5 C rate was changed to constant-current and constant-voltage charge to 4.2 V. The capacity obtained at that time was considered as the 5C-rate characteristic (25° C.) after prolonged cycles at 60° C.

Evaluation 3: Low-Temperature Property (0° C.) after Stored at 60° C.

Each of the nonaqueous electrolytic solution batteries according to Example 12 and Comparative Example 12 was evaluated for the low-temperature property (0° C.) after stored at 60° C. as in Evaluation 3 performed for the nonaqueous electrolytic solution battery according to Example 1-1. Storage tests were performed at an environmental temperature of 60° C. after constant-current and constant-voltage charge to 4.2 V instead of 4.3 V. Moreover, constant-current and constant-voltage charge performed to 4.3 V at 0° C. and a 0.2 C rate was changed to constant-current and constant-voltage charge to 4.2 V. A capacity obtained at this time was considered as the low-temperature property (0° C.) after stored at 60° C.

Various evaluations of the nonaqueous electrolytic solution batteries according to Example 12 and Comparative Example 12 are shown in Table 8 as relative values when the corresponding evaluations after stored at 60° C. for the nonaqueous electrolytic solution battery according to Comparative Example 12-1 are taken as 100.

TABLE 8

| | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 12-1 | Electrolytic solution No.1-21 | 137.9 | 131.7 | 127.3 |
| Example 12-2 | Electrolytic solution No.2-4 | 137.9 | 131.0 | 126.9 |
| Example 12-3 | Electrolytic solution No.3-4 | 137.0 | 131.6 | 126.5 |
| Example 12-4 | Electrolytic solution No.4-6 | 137.4 | 131.9 | 126.9 |
| Example 12-5 | Electrolytic solution No.5-4 | 136.9 | 131.0 | 126.3 |

TABLE 8-continued

|  | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 12-6 | Electrolytic solution No.6-4 | 136.7 | 130.7 | 126.1 |
| Example 12-7 | Electrolytic solution No.9-4 | 136.3 | 130.5 | 125.6 |
| Example 12-8 | Electrolytic solution No.4-8 | 136.7 | 130.6 | 125.9 |
| Comparative Example 12-1 | Comparative electrolytic solution No.1-1 | 100.0 | 100.0 | 100.0 |
| Comparative Example 12-2 | Comparative electrolytic solution No.1-2 | 125.1 | 117.8 | 114.9 |
| Comparative Example 12-3 | Comparative electrolytic solution No.1-6 | 128.2 | 117.8 | 118.5 |
| Comparative Example 12-4 | Comparative electrolytic solution No.2-3 | 128.2 | 117.2 | 118.1 |
| Comparative Example 12-5 | Comparative electrolytic solution No.3-3 | 127.3 | 117.7 | 117.7 |
| Comparative Example 12-6 | Comparative electrolytic solution No.4-3 | 127.7 | 117.9 | 118.1 |
| Comparative Example 12-7 | Comparative electrolytic solution No.5-3 | 127.3 | 117.2 | 117.6 |
| Comparative Example 12-8 | Comparative electrolytic solution No.6-3 | 127.1 | 116.9 | 117.3 |
| Comparative Example 12-9 | Comparative electrolytic solution No.9-3 | 126.7 | 116.8 | 116.9 |
| Comparative Example 12-10 | Comparative electrolytic solution No.4-6 | 127.3 | 120.5 | 117.8 |

(Positive electrode; NCA and Negative electrode; Graphite)

Example 12

The results shown in Table 8 demonstrated that even in a case where NCA was used instead of NMC as a positive-electrode active material, Example 12 was superior to Comparative Example 12 in various evaluation results.

Example 13—Positive Electrode

LFP Negative Electrode

For the nonaqueous electrolytic solution batteries according to Example 13 and Comparative Example 13, a test LFP positive electrode was produced in accordance with the following procedure using a LiFePO$_4$ (LFP) powder as a lithium-containing olivine-type phosphate salt in place of the positive-electrode active material (NCA) used in the nonaqueous electrolytic solution batteries according to Example 12 as described above.

Production of LFP Positive Electrode

A LiFePO$_4$ (LFP) powder, acetylene black (electrically conductive agent 1), and vapor-grown carbon fiber (VGCF®-H, Showa Denko K. K.) (electrically conductive agent 2) were dry-mixed, and uniformly dispersed and mixed into NMP in which PVDF as a binding agent was pre-dissolved, and NMP for adjusting the viscosity was further added to prepare an LFP mixture paste. The resulting paste was applied to an aluminum foil (current collector), dried, and pressurized. Then the aluminum foil was processed into a predetermined size to obtain a test LFP positive electrode. The ratio of solid contents in the negative electrode was LFP:electrically conductive agent 1:electrically conductive agent 2:PVDF=85:4:1:10 (by the mass ratio).

Production of Nonaqueous Electrolytic Solution Batteries

Aluminum laminate housing cell (with a capacity of 30 mAh) including the above test LFP positive electrode, the test graphite negative electrode, and a microporous polypropylene-polyethylene double layered separator were each impregnated with one of the various nonaqueous electrolytic solutions and the various comparative nonaqueous electrolytic solutions shown in Table 7 to produce the nonaqueous electrolytic solution batteries according to Example 13 and Comparative Example 13 in a similar way as in Example 12 and Comparative Example 12 as described above.

Example 13 and Comparative Example 13

Evaluation of Test Cells
Evaluation 1: Low-Temperature Property (0° C.) after 500 Cycles at 60° C.

Each of the nonaqueous electrolytic solution batteries according to Example 13 and Comparative Example 13 was evaluated as described below.

First, the cells produced as described above were subjected to conditioning at an environmental temperature of 25° C. under the following conditions. That is, constant-current and constant-voltage charge was performed as the initial charge/discharge to a charge upper limit voltage of 4.0 V at a 0.1 C rate (3 mA), and discharge was then performed to a discharge cutoff voltage of 2.0 V at a constant current of a 0.2 C rate (6 mA), and subsequently the following charge-discharge cycle was repeated for 3 times: constant-current and constant-voltage charge was performed to a charge upper limit voltage of 4.0 V at a 0.2 C rate (6 mA), and discharge was then performed to a discharge cutoff voltage of 2.0 V at a constant current of a 0.2 C rate (6 mA).

After this conditioning, charge and discharge tests were performed at an environmental temperature of 60° C. The following charge-discharge cycle was repeated for 500 times: constant-current and constant-voltage charge was performed at a 3 C rate (90 mA) to a charge upper limit voltage of 4.0 V, and discharge was performed at a constant current of a 3 C rate (90 mA) to a discharge cutoff voltage of 2.0 V.

Next, the nonaqueous electrolytic solution batteries were cooled to 25° C., and again discharged to 2.0 V. Then constant-current and constant-voltage charge was performed to 4.0 V at a 0.2 C rate at 0° C. Further, discharge was performed at a constant current of a 5 C rate (150 mA) to a discharge cutoff voltage of 2.0 V, and the capacity obtained at that time was taken as the low-temperature property (0° C.) after prolonged cycles at 60° C.

Evaluation 2: 5C-Rate Characteristic after 500 Cycles at 60° C.

After performing 500 cycles at an environmental temperature of 60° C. in Evaluation 1 as described above, the nonaqueous electrolytic solution batteries were cooled to 25° C., and then again discharged to 2.0 V. Subsequently constant-current and constant-voltage charge was performed to 4.0 V at 25° C. and at a 5 C rate. Further, discharge was performed at a constant current of a 5 C rate (150 mA) to a discharge cutoff voltage of 2.0 V, and the capacity obtained at that time was taken as the 5C-rate characteristic (25° C.) after prolonged cycles at 60° C.

Evaluation 3: Low-Temperature Property (0° C.) after Stored at 60° C.

Each of the nonaqueous electrolytic solution batteries according to Example 13 and Comparative Example 13 was subjected to storage tests (stored for 10 days after charged to 4.0 V) at an environmental temperature of 60° C.

Next, the nonaqueous electrolytic solution batteries were cooled to 25° C., and again discharged to 2.0 V. Then constant-current and constant-voltage charge was performed to 4.0 V at a 0.2 C rate at 0° C. Further, discharge was performed at a constant current of a 5 C rate (150 mA) to a discharge cutoff voltage of 2.0 V while maintaining the temperature at 0° C., and the capacity obtained at that time was taken as the low-temperature property (0° C.) after stored at 60° C.

Various evaluations of the nonaqueous electrolytic solution batteries according to Example 13 and Comparative Example 13 are shown in Table 9 as relative values when the corresponding evaluations of the nonaqueous electrolytic solution battery according to Comparative Example 13-1 are taken as 100.

TABLE 9

|  | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 13-1 | Electrolytic solution No.1-21 | 137.1 | 130.9 | 126.5 |
| Example 13-2 | Electrolytic solution No.2-4 | 137.1 | 130.3 | 126.2 |
| Example 13-3 | Electrolytic solution No.3-4 | 136.1 | 130.8 | 125.8 |
| Example 13-4 | Electrolytic solution No.4-6 | 136.7 | 131.3 | 126.3 |
| Example 13-5 | Electrolytic solution No.5-4 | 136.1 | 130.3 | 125.6 |
| Example 13-6 | Electrolytic solution No.6-4 | 135.9 | 129.9 | 125.3 |
| Example 13-7 | Electrolytic solution No.9-4 | 135.3 | 129.6 | 124.7 |
| Example 13-8 | Electrolytic solution No.4-8 | 139.2 | 133.0 | 128.2 |
| Comparative Example 13-1 | Comparative electrolytic solution No.1-1 | 100.0 | 100.0 | 100.0 |
| Comparative Example 13-2 | Comparative electrolytic solution No.1-2 | 124.8 | 117.6 | 114.7 |
| Comparative Example 13-3 | Comparative electrolytic solution No.1-6 | 127.5 | 117.1 | 117.7 |
| Comparative Example 13-4 | Comparative electrolytic solution No.2-3 | 127.5 | 116.5 | 117.4 |
| Comparative Example 13-5 | Comparative electrolytic solution No.3-3 | 126.6 | 117.0 | 117.0 |
| Comparative Example 13-6 | Comparative electrolytic solution No.4-3 | 127.1 | 117.4 | 117.6 |
| Comparative Example 13-7 | Comparative electrolytic solution No.5-3 | 126.5 | 116.5 | 116.9 |
| Comparative Example 13-8 | Comparative electrolytic solution No.6-3 | 126.4 | 116.2 | 116.6 |
| Comparative Example 13-9 | Comparative electrolytic solution No.9-3 | 125.7 | 115.9 | 116.0 |
| Comparative Example 13-10 | Comparative electrolytic solution No.4-6 | 126.5 | 119.7 | 117.0 |

(Positive electrode; LFP, negative electrode; graphite)

Example 13

As seen from the results in Table 9, Example 13 showed a similar tendency as Example 12. That is, even in a case where LFP was used instead of NCA as a positive-electrode active material, Example 13 was superior to Comparative Example 13 in various evaluations.

Example 14—Positive Electrode

OLO-1 Positive Electrode Preparation of Nonaqueous Electrolytic Solutions Nos. 14-1 to 14-8 and Comparative Electrolytic Solutions Nos. 14-2 to 14-11

In a dry box under a nitrogen atmosphere of a dew point of −50° C. or less, $LiPF_6$ as an electrolyte was dissolved and prepared in a preheated and dissolved nonaqueous solvent of EC and EMC, and FEC as the group (V) compound (volume ratio 25:70:5/mass ratio 29.7:63.6:6.7) so that the concentration of $LiPF_6$ was 1.2 mol/liter, and then various ionic complex/EMC solutions according to the present invention and the group (II), group (III), group (IV), and group (V) compounds were each added in a predetermined amount to prepare the nonaqueous electrolytic solutions Nos. 14-1 to 14-8 according to the present invention and comparative electrolytic solutions Nos. 14-2 to 14-11.

Preparation of comparative electrolytic solution No. 14-1

Comparative electrolytic solution No. 14-1 was prepared as Comparative Example.

In a dry box under a nitrogen atmosphere of a dew point of −50° C. or less, $LiPF_6$ as an electrolyte was dissolved and prepared in a preheated and dissolved nonaqueous solvent of EC and EMC (volume ratio 30:70/mass ratio 35.9:64.1) so that the concentration of $LiPF_6$ was 1.2 mol/liter to prepare the nonaqueous electrolytic solution No. 16-1. It is noted that the comparative electrolytic solution No. 14-1 was prepared in the same way as in the nonaqueous electrolytic solutions Nos. 14-1 to 14-8 according to the present invention except that the various ionic complex/EMC solutions shown in Table 10 below and the group (II) compounds described above were not added.

TABLE 10

| Electrolytic solution No, | Li salt LiPF$_6$ (mol/liter) | Nonaqueous solvent EC (mass %) | Nonaqueous solvent EMC (mass %) | Group (V) compound 1 | Content (mass %) | Group (I) compound (Cis isomer) | Content (mass %) | Group (II) compound | Content (mass %) |
|---|---|---|---|---|---|---|---|---|---|
| Electrolytic solution No. 14-1 | 1.2 | 29.7 | 63.6 | FEC | 6.7 | Synthesis Example 1 (1a-Cis) | 1.2 | 1,3-PS | 2.4 |
| Electrolytic solution No. 14-2 | | | | | | | | 1,3-PRS | 1.2 |
| Electrolytic solution No. 14-3 | | | | | | | | Formula (II-2a-4) | 1.2 |
| Electrolytic solution No. 14-4 | | | | | | | | Formula (II-3a-1) | 1.2 |
| Electrolytic solution No. 14-5 | | | | | | | | Formula (II-3a-15) | 1.2 |
| Electrolytic solution No. 14-6 | | | | | | | | Butane-DMS | 1.2 |
| Electrolytic solution No. 14-7 | | | | | | | | Succinonitrile | 1.2 |
| Electrolytic solution No. 14-8 | | | | | | | | Formula (II-3b-1) | 1.2 |
| Comparative electrolytic solution No. 14-1 | 1.2 | 35.9 | 64.1 | — | — | — | — | — | — |
| Comparative electrolytic solution No. 14-2 | 1.2 | 29.7 | 63.6 | FEC | 6.7 | — | — | — | — |
| Comparative electrolytic solution No. 14-3 | | | | | | Synthesis Example 1 (1a-Cis) | 1.2 | — | — |
| Comparative electrolytic solution No. 14-4 | | | | | | — | — | 1,3-PS | 2.4 |
| Comparative electrolytic solution No. 14-5 | | | | | | — | — | 1,3-PRS | 1.2 |
| Comparative electrolytic solution No. 14-6 | | | | | | — | — | Formula (II-2a-4) | 1.2 |
| Comparative electrolytic solution No. 14-7 | | | | | | — | — | Formula (II-3a-1) | 1.2 |
| Comparative electrolytic solution No. 14-8 | | | | | | — | — | Formula (II-3a-15) | 1.2 |
| Comparative electrolytic solution No. 14-9 | | | | | | — | — | Butane-DMS | 1.2 |
| Comparative electrolytic solution No. 14-10 | | | | | | — | — | Succinonitrile | 1.2 |
| Comparative electrolytic solution No. 14-11 | | | | | | — | — | Formula (II-3b-1) | 1.2 |

TABLE 10-continued

| Electrolytic solution No, | Group (III) compound Trans isomer | Content (mass %) | Trans isomer/ Cis isomer | Group (IV) compound Tetrafluoro complex | Content (mass %) | Tetrafluoro complex/ Cis isomer | Group (V) compound 2 | Content (mass %) |
|---|---|---|---|---|---|---|---|---|
| Electrolytic solution No. 14-1 | Synthesis Example 1 (1a-Trans) | 0.006 | 0.005 | Synthesis Example 2 (5a-Tetra) | 0.144 | 0.12 | EEC | 1.0 |
| Electrolytic solution No. 14-2 | | | | | | | | |
| Electrolytic solution No. 14-3 | | | | | | | | |
| Electrolytic solution No. 14-4 | | | | | | | | |
| Electrolytic solution No. 14-5 | | | | | | | | |
| Electrolytic solution No. 14-6 | | | | | | | | |
| Electrolytic solution No. 14-7 | | | | | | | | |
| Electrolytic solution No. 14-8 | | | | | | | | |
| Comparative electrolytic solution No. 14-1 | — | — | — | — | — | — | — | — |
| Comparative electrolytic solution No. 14-2 | — | — | — | — | — | — | — | — |
| Comparative electrolytic solution No. 14-3 | — | — | — | — | — | — | — | — |
| Comparative electrolytic solution No. 14-4 | Synthesis Example 1 (1a-Trans) | 1.2 | — | Synthesis Example 2 (5a-Tetra) | 0.144 | — | EEC | 1.0 |
| Comparative electrolytic solution No. 14-5 | | | | | | | | |
| Comparative electrolytic solution No. 14-6 | | | | | | | | |
| Comparative electrolytic solution No. 14-7 | | | | | | | | |
| Comparative electrolytic solution No. 14-8 | | | | | | | | |
| Comparative electrolytic solution No. 14-9 | | | | | | | | |
| Comparative electrolytic solution No. 14-10 | | | | | | | | |
| Comparative electrolytic solution No. 14-11 | | | | | | | | |

Example 14 and Comparative Example 14

Production and Evaluation of Nonaqueous Electrolytic Solution Batteries

A test OLO-1 positive electrode was produced as described below using a $0.5[\text{LiNi}_{0.5}\text{Mn}_{0.5}\text{O}_2] \cdot 0.5[\text{Li}_2\text{MnO}_3]$ (OLO-1) powder as a lithium-rich layered transition-metal oxide having the stratified rock-salt structure in place of the positive-electrode active material (NCA) used in the nonaqueous electrolytic solution batteries according to Example 12 as described above.

Production of OLO-1 Positive Electrode

A $0.5[\text{LiNi}_{0.5}\text{Mn}_{0.5}\text{O}_2]$ (OLO-1) powder, acetylene black (electrically conductive agent 1), and vapor-grown carbon fiber (VGCF®-H, Showa Denko K. K.) (electrically conductive agent 2) were dry-mixed, and uniformly dispersed and mixed into NMP in which PVDF as a binding agent was pre-dissolved, and NMP for adjusting the viscosity was then further added to prepare an OLO-1 mixture paste. The resulting paste was applied to an aluminum foil (current collector), dried, and pressurized. Then the aluminum foil was processed into a predetermined size to obtain a test OLO-1 positive electrode. The ratio of solid contents in the positive electrode was OLO-1:electrically conductive agent 1:electrically conductive agent 2:PVDF=85:4:1:10 (by the mass ratio).

Production of Nonaqueous Electrolytic Solution Batteries

Aluminum laminate housing cells (with a capacity of 30 mAh) including the above test OLO-1 positive electrode, the test graphite negative electrode, and a microporous polypropylene-polyethylene double layered separator were each impregnated with one of the various nonaqueous electrolytic solutions and the various comparative nonaqueous electrolytic solutions shown in Table 10 to produce the nonaqueous electrolytic solution batteries according to Example 14 and Comparative Example 14 in a similar way as in Example 12 and Comparative Example 12 as described above.

Example 14 and Comparative Example 14

Evaluation of Test Cells
Evaluation 1: Low-Temperature Property (0° C.) after 300 Cycles at 60° C.

Each of the nonaqueous electrolytic solution batteries according to Example 14 and Comparative Example 14 was evaluated as described below.

First, conditioning was performed at an environmental temperature of 25° C. under the following conditions.

That is, constant-current and constant-voltage charge was performed as the initial charge/discharge at an environmental temperature of 25° C. using the produced cells to a charge upper limit voltage of 4.2 V at a 0.05 C rate (1.5 mA), and discharge was performed at a constant current of a 0.1 C rate (3 mA) to a discharge cutoff voltage of 2.5 V. Then, the following charge-discharge cycle was repeated for 5 times: constant-current and constant-voltage charge was performed at a 0.1 C rate (3 mA) to a charge upper limit voltage of 4.4 V, and then discharge was performed at a constant current of a 0.1 C rate (3 mA) to a discharge cutoff voltage of 2.5 V.

After this conditioning, the following charge-discharge cycle was repeated for 3 times at an environmental temperature of 25° C.: constant-current and constant-voltage charge was performed to a charge upper limit voltage of 4.6 V at a 0.1 C rate (3 mA), and discharge was then performed at a constant current of a 0.2 C rate (6 mA) to a discharge cutoff voltage of 2.5 V.

Then, charge/discharge tests were performed at an environmental temperature of 60° C. The following charge-discharge cycle was repeated for 300 times: constant-current and constant-voltage charge was performed at a 1 C rate (30 mA) to a charge upper limit voltage of 4.6 V, and discharge was performed at a constant current of a 2 C rate (60 mA) to a discharge cutoff voltage of 2.5 V.

Next, the nonaqueous electrolytic solution batteries were cooled to 25° C., and again discharged to 2.5 V. Then constant-current and constant-voltage charge was performed to 4.6 V at a 0.2 C rate at 0° C. Further, discharge was performed at a constant current of a 3 C rate (90 mA) to a discharge cutoff voltage of 2.5 V, and the capacity obtained at that time was taken as the low-temperature property (0° C.) after prolonged cycles at 60° C.

Evaluation 2: 3C-Rate Characteristic (25° C.) after 300 Cycles at 60° C.

After performing 300 cycles at an environmental temperature of 60° C. in Evaluation 1 as described above, the nonaqueous electrolytic solution batteries were cooled to 25° C., and then again discharged to 2.5 V. Subsequently constant-current and constant-voltage charge was performed to 4.6 V at a 0.1 C rate at 25° C. Further, discharge was performed at a constant current of a 3 C rate (90 mA) to a discharge cutoff voltage of 2.5 V, and the capacity obtained at that time was taken as the 3C-rate characteristic (25° C.) after prolonged cycles at 60° C.

Evaluation 3: Low-Temperature Property (0° C.) after Stored at 60° C.

Each of the nonaqueous electrolytic solution batteries according to Example 14 and Comparative Example 14 was subjected to storage tests (stored for 10 days after charged to 4.6 V) at an environmental temperature of 60° C.

Next, the nonaqueous electrolytic solution batteries were cooled to 25° C., and again discharged to 2.5 V. Then constant-current and constant-voltage charge was performed to 4.6 V at a 0.2 C rate at 0° C. Further, discharge was performed at a constant current of a 3 C rate (90 mA) to a discharge cutoff voltage of 2.5 V while maintaining the temperature at 0° C., and the capacity obtained at that time was taken as the low-temperature property (0° C.) after stored at 60° C.

Various evaluations of the nonaqueous electrolytic solution batteries according to Example 14 and Comparative Example 14 are shown in Table 11 as relative values when various evaluations of the nonaqueous electrolytic solution battery according to Comparative Example 14-1 are taken as 100.

TABLE 11

| | Electrolytic solution No, | Low-temperature property (0° C.) after prolonged cycles at 60° C. | 3C-rate characteristic (25° C.) after prolonged cycles at 60° C. | Low-temperature property (0° C.) after stored at 60° C. |
|---|---|---|---|---|
| Example 14-1 | Electrolytic solution No.14-1 | 134.4 | 128.3 | 124.0 |
| Example 14-2 | Electrolytic solution No.14-2 | 134.1 | 128.1 | 123.8 |
| Example 14-3 | Electrolytic solution No.14-3 | 133.3 | 127.3 | 123.0 |
| Example 14-4 | Electrolytic solution No.14-4 | 133.0 | 127.1 | 122.8 |

TABLE 11-continued

|  | Electrolytic solution No, | Low-temperature property (0° C.) after prolonged cycles at 60° C. | 3C-rate characteristic (25° C.) after prolonged cycles at 60° C. | Low-temperature property (0° C.) after stored at 60° C. |
|---|---|---|---|---|
| Example 14-5 | Electrolytic solution No.14-5 | 132.9 | 126.9 | 122.7 |
| Example 14-6 | Electrolytic solution No.14-6 | 133.4 | 127.4 | 123.2 |
| Example 14-7 | Electrolytic solution No.14-7 | 133.2 | 127.2 | 122.9 |
| Example 14-8 | Electrolytic solution No.14-8 | 132.8 | 126.9 | 122.6 |
| Comparative Example 14-1 | Comparative electrolytic solution No.14-1 | 100.0 | 100.0 | 100.0 |
| Comparative Example 14-2 | Comparative electrolytic solution No.14-2 | 118.8 | 113.3 | 110.4 |
| Comparative Example 14-3 | Comparative electrolytic solution No.14-3 | 121.6 | 114.7 | 111.7 |
| Comparative Example 14-4 | Comparative electrolytic solution No.14-4 | 127.2 | 121.5 | 117.4 |
| Comparative Example 14-5 | Comparative electrolytic solution No.14-5 | 127.0 | 121.3 | 117.2 |
| Comparative Example 14-6 | Comparative electrolytic solution No.14-6 | 126.2 | 120.6 | 116.5 |
| Comparative Example 14-7 | Comparative electrolytic solution No.14-7 | 126.0 | 120.3 | 116.3 |
| Comparative Example 14-8 | Comparative electrolytic solution No.14-8 | 125.8 | 120.2 | 116.1 |
| Comparative Example 14-9 | Comparative electrolytic solution No.14-9 | 126.4 | 120.7 | 116.6 |
| Comparative Example 14-10 | Comparative electrolytic solution No.14-10 | 126.1 | 120.4 | 116.4 |
| Comparative Example 14-11 | Comparative electrolytic solution No.14-11 | 125.8 | 120.1 | 116.1 |

(Positive electrode; OLO-1, Negative electrode; Graphite)

Example 14

The results shown in Table 11 revealed that even in a case where OLO-1 was used as a positive-electrode active material, Example 14 was superior to Comparative Example 14 in various evaluation results.

The results as described above demonstrated that the nonaqueous electrolytic solutions according to the present invention showed good effects in any of the cases where the following oxides were used as a positive electrode: a lithium transition-metal composite oxide containing at least one metal of nickel, manganese, and cobalt and having a layered structure; a lithium-manganese composite oxide having the spinel structure; a lithium-containing olivine-type iron phosphate; and a lithium-rich layered transition-metal oxide having the stratified rock-salt structure.

That is, these results clearly demonstrate that the nonaqueous electrolytic solution according to the present invention, and batteries including the nonaqueous electrolytic solution according to the present invention can show high output characteristics at low temperature even after the batteries are used to some extent, and can also show sufficient performance again at low temperature even after stored at high temperature regardless of types of positive electrodes.

Example 15—Negative Electrode

Amorphous Carbon Negative Electrode

A test amorphous carbon negative electrode was produced as described below using an amorphous carbon powder as a carbon material having a d value in the lattice plane (002) of more than 0.340 nm as determined by X ray diffraction in place of the negative-electrode active material (a graphite powder) used in the nonaqueous electrolytic solution batteries according to Example 1 as described above.

Production of Amorphous Carbon Negative Electrode

Carbotron® P from Kureha Corporation as an amorphous carbon powder was uniformly dispersed and mixed into NMP in which PVDF as a binding agent was pre-dissolved, and NMP for adjusting the viscosity was then further added to prepare an amorphous carbon mixture paste. The above paste was applied to a copper foil (current collector), dried, and pressurized. Then the copper foil was processed into a predetermined size to obtain a test amorphous carbon negative electrode. The ratio of solid contents in the negative electrode was amorphous carbon powder:PVDF=90:10 (by the mass ratio).

Preparation of Nonaqueous Electrolytic Solutions Nos. 15-1 to 15-8 and Comparative Electrolytic Solutions Nos. 15-1 to 15-10

In a dry box under a nitrogen atmosphere of a dew point of −50° C. or less, LiPF$_6$ as an electrolyte was dissolved and prepared in a nonaqueous solvent of propylene carbonate (PC), EMC, and DEC (volume ratio 30:40:30/mass ratio 34.1:38.3:27.6) so that the concentration of LiPF$_6$ was 1.1 mol/liter, and various ionic complex/EMC solutions according to the present invention and the group (II) compounds as described above were then added in predetermined amounts as described in Table 12 to prepare the nonaqueous electrolytic solutions Nos. 15-1 to 15-8 according to the present invention and comparative electrolytic solutions Nos. 15-1 to 15-10.

Production of Nonaqueous Electrolytic Solution Batteries

Aluminum laminate housing cells (with a capacity of 30 mAh) including the above test NMC positive electrode, the test amorphous carbon negative electrode, and a microporous polypropylene-polyethylene double layered separator were each impregnated with one of the various nonaqueous electrolytic solutions and the various comparative nonaqueous electrolytic solutions shown in Table 12 to produce the nonaqueous electrolytic solution batteries according to Example 15 and Comparative Example 15.

TABLE 12

| Electrolytic solution No, | Group (I) compound (Cis isomer) | Content (mass %) | Group (II) compound | Content (mass %) | Group (III) compound Trans isomer | Content (mass %) |
|---|---|---|---|---|---|---|
| Electrolytic solution No. 15-1 | Synthesis Example 1 (1a-Cis) | 1.1 | 1,3-PS | 2.0 | Synthesis Example 1 (1a-Trans) | 0.0055 |

TABLE 12-continued

| Electrolytic solution No. | | | | | | |
|---|---|---|---|---|---|---|
| Electrolytic solution No. 15-2 | Synthesis Example 1 (1a-Cis) | 1.1 | 1,3-PRS | 1.0 | Synthesis Example 1 (1a-Trans) | 0.0055 |
| Electrolytic solution No. 15-3 | Synthesis Example 1 (1a-Cis) | 1.1 | Formula (II-2a-4) | 1.0 | Synthesis Example 1 (1a-Trans) | 0.0055 |
| Electrolytic solution No. 15-4 | Synthesis Example 1 (1a-Cis) | 1.1 | Formula (II-3a-1) | 1.0 | Synthesis Example 1 (1a-Trans) | 0.0055 |
| Electrolytic solution No. 15-5 | Synthesis Example 1 (1a-Cis) | 1.1 | Formula (II-3a-15) | 1.0 | Synthesis Example 1 (1a-Trans) | 0.0055 |
| Electrolytic solution No. 15-6 | Synthesis Example 1 (1a-Cis) | 1.1 | Butane-DMS | 1.0 | Synthesis Example 1 (1a-Trans) | 0.0055 |
| Electrolytic solution No. 15-7 | Synthesis Example 1 (1a-Cis) | 1.1 | Succinonitrile | 1.0 | Synthesis Example 1 (1a-Trans) | 0.0055 |
| Electrolytic solution No. 15-8 | Synthesis Example 1 (1a-Cis) | 1.1 | Formula (II-3b-1) | 1.0 | Synthesis Example 1 (1a-Trans) | 0.0055 |
| Comparative electrolytic solution No. 15-1 | — | — | — | — | — | — |
| Comparative electrolytic solution No. 15-2 | Synthesis Example 1 (1a-Cis) | 1.1 | — | — | — | — |
| Comparative electrolytic solution No. 15-3 | — | — | 1,3-PS | 2.0 | Synthesis Example 1 (1a-Trans) | 1.1 |
| Comparative electrolytic solution No. 15-4 | — | — | 1,3-PRS | 1.0 | Synthesis Example 1 (1a-Trans) | 1.1 |
| Comparative electrolytic solution No. 15-5 | — | — | Formula (II-2a-4) | 1.0 | Synthesis Example 1 (1a-Trans) | 1.1 |
| Comparative electrolytic solution No. 15-6 | — | — | Formula (II-3a-1) | 1.0 | Synthesis Example 1 (1a-Trans) | 1.1 |
| Comparative electrolytic solution No. 15-7 | — | — | Formula (II-3a-15) | 1.0 | Synthesis Example 1 (1a-Trans) | 1.1 |
| Comparative electrolytic solution No. 15-8 | — | — | Butane-DMS | 1.0 | Synthesis Example 1 (1a-Trans) | 1.1 |
| Comparative electrolytic solution No. 15-9 | — | — | Succinonitrile | 1.0 | Synthesis Example 1 (1a-Trans) | 1.1 |
| Comparative electrolytic solution No. 15-10 | — | — | Formula (II-3b-1) | 1.0 | Synthesis Example 1 (1a-Trans) | 1.1 |

| Electrolytic solution No. | Trans isomer/Cis isomer (mass ratio) | Group (IV) compound Tetrafluoro complex | Content (mass %) | Tetrafluoro complex/Cis isomer (mass ratio) | Group (V) compound | Content (mass %) |
|---|---|---|---|---|---|---|
| Electrolytic solution No. 15-1 | 0.005 | Synthesis Example 2 (5a-Tetra) | 0.132 | 0.12 | — | — |
| Electrolytic solution No. 15-2 | 0.005 | Synthesis Example 2 (5a-Tetra) | 0.132 | 0.12 | — | — |
| Electrolytic solution No. 15-3 | 0.005 | Synthesis Example 2 (5a-Tetra) | 0.132 | 0.12 | — | — |
| Electrolytic solution No. 15-4 | 0.005 | Synthesis Example 2 (5a-Tetra) | 0.132 | 0.12 | — | — |
| Electrolytic solution No. 15-5 | 0.005 | Synthesis Example 2 (5a-Tetra) | 0.132 | 0.12 | — | — |
| Electrolytic solution No. 15-6 | 0.005 | Synthesis Example 2 (5a-Tetra) | 0.132 | 0.12 | — | — |
| Electrolytic solution No. 15-7 | 0.005 | Synthesis Example 2 (5a-Tetra) | 0.132 | 0.12 | — | — |

TABLE 12-continued

| | | | | | | |
|---|---|---|---|---|---|---|
| Electrolytic solution No. 15-8 | 0.005 | Synthesis Example 2 (5a-Tetra) | 0.132 | 0.12 | — | — |
| Comparative electrolytic solution No. 15-1 | — | — | — | — | — | — |
| Comparative electrolytic solution No. 15-2 | — | — | — | — | — | — |
| Comparative electrolytic solution No. 15-3 | — | Synthesis Example 2 (5a-Tetra) | 0.132 | — | — | — |
| Comparative electrolytic solution No. 15-4 | — | Synthesis Example 2 (5a-Tetra) | 0.132 | — | — | — |
| Comparative electrolytic solution No. 15-5 | — | Synthesis Example 2 (5a-Tetra) | 0.132 | — | — | — |
| Comparative electrolytic solution No. 15-6 | — | Synthesis Example 2 (5a-Tetra) | 0.132 | — | — | — |
| Comparative electrolytic solution No. 15-7 | — | Synthesis Example 2 (5a-Tetra) | 0.132 | — | — | — |
| Comparative electrolytic solution No. 15-8 | — | Synthesis Example 2 (5a-Tetra) | 0.132 | — | — | — |
| Comparative electrolytic solution No. 15-9 | — | Synthesis Example 2 (5a-Tetra) | 0.132 | — | — | — |
| Comparative electrolytic solution No. 15-10 | — | Synthesis Example 2 (5a-Tetra) | 0.132 | — | — | — |

Example 15 and Comparative Example 15—Evaluation of Test Cells

Evaluation 1: Low-Temperature Property (0° C.) after 500 Cycles at 60° C.

For each of the nonaqueous electrolytic solution batteries according to Example 15 and Comparative Example 15, conditioning was performed at an environmental temperature of 25° C. under the following conditions as in Evaluation 1 performed for the nonaqueous electrolytic solution batteries according to Example 12.

That is, constant-current and constant-voltage charge was performed as the initial charge/discharge at an environmental temperature of 25° C. using the produced cells to a charge upper limit voltage of 4.2 V at a 0.1 C rate (3 mA), and discharge was performed at a constant current of a 0.2 C rate (6 mA) to a discharge cutoff voltage of 2.7 V. Subsequently, the following charge-discharge cycle was repeated for 3 times: constant-current and constant-voltage charge was performed to a charge upper limit voltage of 4.2 V at a 0.2 C rate (6 mA), and discharge was performed at a constant current of a 0.2 C rate (6 mA) to a discharge cutoff voltage of 2.7 V.

After this conditioning, similar evaluation was performed except that when 500 cycles at an environmental temperature of 60° C. were performed, the discharge cutoff voltage was changed from 3.0 V to 2.7 V, and when constant-current and constant-voltage charge was performed to 4.2 V at a 0.2 C rate at 0° C., and then discharge was performed while maintaining the temperature at 0° C., the discharge cutoff voltage was changed from 3.0 V to 2.7 V, and discharge was performed at a constant current of a 5 C rate (150 mA). The capacity obtained at that time was considered as the low-temperature property (0° C.) after prolonged cycles at 60° C.

Evaluation 2: 5C-Rate Characteristic after 500 Cycles at 60°

Each of the nonaqueous electrolytic solution batteries according to Example 15 and Comparative Example 15 was evaluated as in Evaluation 2 performed for the nonaqueous electrolytic solution batteries according to Example 14 except that the discharge cutoff voltage was changed from 3.0 V to 2.7 V upon discharge at a 5 C rate at 25° C. The capacity obtained at that time was considered as the 5C-rate characteristic (25° C.) after prolonged cycles at 60° C.

Evaluation 3: Low-Temperature Property (0° C.) after Stored at 60° C.

Each of the nonaqueous electrolytic solution batteries according to Example 15 and Comparative Example 15 was subjected to storage tests (stored for 10 days after charged to 4.2 V at a constant current and a constant voltage) at an environmental temperature of 60° C. as in Evaluation 3 performed for the nonaqueous electrolytic solution batteries according to Example 14 except that the discharge cutoff voltage was changed from 3.0 V to 2.7 V upon discharge at a 5 C rate while maintaining the temperature at 0° C. The capacity obtained at that time was considered as the low-temperature property (0° C.) after stored at 60° C.

Various evaluations of the nonaqueous electrolytic solution batteries according to Example 15 and Comparative Example 15 are shown in Table 13 as relative values when various evaluations of the nonaqueous electrolytic solution battery according to Comparative Example 15-1 are taken as 100.

TABLE 13

| | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 15-1 | Electrolytic solution No.15-1 | 135.3 | 129.2 | 124.9 |
| Example 15-2 | Electrolytic solution No.15-2 | 135.3 | 128.6 | 124.5 |
| Example 15-3 | Electrolytic solution No.15-3 | 134.4 | 129.1 | 124.1 |
| Example 15-4 | Electrolytic solution No 15-4 | 135.0 | 129.5 | 124.7 |
| Example 15-5 | Electrolytic solution No.15-5 | 134.3 | 128.6 | 124.0 |
| Example 15-6 | Electrolytic solution No.15-6 | 134.1 | 128.2 | 123.7 |
| Example 15-7 | Electrolytic solution No.15-7 | 133.5 | 127.9 | 123.1 |
| Example 15-8 | Electrolytic solution No.15-8 | 134.3 | 128.5 | 123.7 |
| Comparative Example 15-1 | Comparative electrolytic solution No.15-1 | 100.0 | 100.0 | 100.0 |
| Comparative Example 15-2 | Comparative electrolytic solution No.15-2 | 122.6 | 115.4 | 112.6 |
| Comparative Example 15-3 | Comparative electrolytic solution No.15-3 | 125.8 | 115.6 | 116.2 |
| Comparative Example 15-4 | Comparative electrolytic solution No.15-4 | 125.8 | 115.0 | 115.9 |
| Comparative Example 15-5 | Comparative electrolytic solution No.15-5 | 124.9 | 115.5 | 115.5 |
| Comparative Example 15-6 | Comparative electrolytic solution No.15-6 | 125.5 | 115.9 | 116.0 |
| Comparative Example 15-7 | Comparative electrolytic solution No.15-7 | 124.9 | 115.0 | 115.4 |
| Comparative Example 15-8 | Comparative electrolytic solution No.15-8 | 124.7 | 114.7 | 115.1 |
| Comparative Example 15-9 | Comparative electrolytic solution No.15-9 | 124.1 | 114.4 | 114.5 |
| Comparative Example 15-10 | Comparative electrolytic solution No.15-10 | 124.9 | 117.6 | 115.1 |

(Positive electrode; NMC, Negative electrode; Amorphous carbon)

Example 15

The results shown in Table 13 revealed that even in a case where an amorphous carbon powder (Carbotron® P) was used instead of a graphite powder as a negative-electrode active material, Example 15 was superior to Comparative Example 15 in various evaluation results.

Example 16—Negative Electrode (Mixture of Artificial Graphite+Natural Graphite) Negative Electrode Preparation of Nonaqueous Electrolytic Solutions Nos. 16-1 to 16-8 and Comparative Electrolytic Solution Nos. 16-1 to 16-10

In a dry box under a nitrogen atmosphere of a dew point of −50° C. or less, $LiPF_6$ as an electrolyte was dissolved and prepared in a preheated and dissolved nonaqueous solvent of EC, EMC, and DEC (volume ratio 25:45:30/mass ratio 30.7:42.2:27.1) so that the concentration of $LiPF_6$ was 1.2 mol/liter, and then various ionic complex/EMC solutions according to the present invention and the group (II) compounds as described above were added in predetermined amounts as shown in Table 14 to prepare the nonaqueous electrolytic solutions Nos. 16-1 to 16-8 and comparative electrolytic solutions Nos. 16-1 to 16-10 according to the present invention.

TABLE 14

| Electrolytic solution No, | Group (I) compound (Cis isomer) | Content (mass %) | Group (II) compound | Content (mass %) | Group (III) compound Trans isomer | Content (mass %) |
|---|---|---|---|---|---|---|
| Electrolytic solution No. 16-1 | Synthesis Example 1 (1a-Cis) | 1.1 | 1,3-PS | 2.0 | Synthesis Example 1 (1a-Trans) | 0.0055 |
| Electrolytic solution No. 16-2 | Synthesis Example 1 (1a-Cis) | 1.1 | 1,3-PRS | 1.0 | Synthesis Example 1 (1a-Trans) | 0.0055 |
| Electrolytic solution No. 16-3 | Synthesis Example 1 (1a-Cis) | 1.1 | Formula (II-2a-4) | 1.0 | Synthesis Example 1 (1a-Trans) | 0.0055 |
| Electrolytic solution No. 16-4 | Synthesis Example 1 (1a-Cis) | 1.1 | Formula (II-3a-1) | 1.0 | Synthesis Example 1 (1a-Trans) | 0.0055 |

TABLE 14-continued

| Electrolytic solution No. | Synthesis Example (Cis) | Cis content | Group (II) compound | Content (mass %) | Synthesis Example (Trans) | Trans content | Trans isomer/Cis isomer (mass ratio) | Group (IV) compound Tetrafluoro complex | Content (mass %) | Tetrafluoro complex/Cis isomer (mass ratio) | Group (V) compound | Content (mass %) |
|---|---|---|---|---|---|---|---|---|---|---|---|---|
| Electrolytic solution No. 16-5 | Synthesis Example 1 (1a-Cis) | 1.1 | Formula (II-3a-15) | 1.0 | Synthesis Example 1 (1a-Trans) | 0.0055 | 0.005 | Synthesis Example 2 (5a-Tetra) | 0.132 | 0.12 | — | — |
| Electrolytic solution No. 16-6 | Synthesis Example 1 (1a-Cis) | 1.1 | Butane-DMS | 1.0 | Synthesis Example 1 (1a-Trans) | 0.0055 | 0.005 | Synthesis Example 2 (5a-Tetra) | 0.132 | 0.12 | — | — |
| Electrolytic solution No. 16-7 | Synthesis Example 1 (1a-Cis) | 1.1 | Succinonitrile | 1.0 | Synthesis Example 1 (1a-Trans) | 0.0055 | 0.005 | Synthesis Example 2 (5a-Tetra) | 0.132 | 0.12 | — | — |
| Electrolytic solution No. 16-8 | Synthesis Example 1 (1a-Cis) | 1.1 | Formula (II-3b-1) | 1.0 | Synthesis Example 1 (1a-Trans) | 0.0055 | 0.005 | Synthesis Example 2 (5a-Tetra) | 0.132 | 0.12 | — | — |
| Comparative electrolytic solution No. 16-1 | — | — | — | — | — | — | — | — | — | — | — | — |
| Comparative electrolytic solution No. 16-2 | Synthesis Example 1 (1a-Cis) | 1.1 | — | — | — | — | — | — | — | — | — | — |
| Comparative electrolytic solution No. 16-3 | — | — | 1,3-PS | 2.0 | Synthesis Example 1 (1a-Trans) | 1.1 | — | Synthesis Example 2 (5a-Tetra) | 0.132 | — | — | — |
| Comparative electrolytic solution No. 16-4 | — | — | 1,3-PRS | 1.0 | Synthesis Example 1 (1a-Trans) | 1.1 | | | | | | |
| Comparative electrolytic solution No. 16-5 | — | — | Formula (II-2a-4) | 1.0 | Synthesis Example 1 (1a-Trans) | 1.1 | | | | | | |
| Comparative electrolytic solution No. 16-6 | — | — | Formula (II-3a-1) | 1.0 | Synthesis Example 1 (1a-Trans) | 1.1 | | | | | | |
| Comparative electrolytic solution No. 16-7 | — | — | Formula (II-3a-15) | 1.0 | Synthesis Example 1 (1a-Trans) | 1.1 | | | | | | |
| Comparative electrolytic solution No. 16-8 | — | — | Butane-DMS | 1.0 | Synthesis Example 1 (1a-Trans) | 1.1 | | | | | | |
| Comparative electrolytic solution No. 16-9 | — | — | Succinonitrile | 1.0 | Synthesis Example 1 (1a-Trans) | 1.1 | | | | | | |
| Comparative electrolytic solution No. 16-10 | — | — | Formula (II-3b-1) | 1.0 | Synthesis Example 1 (1a-Trans) | 1.1 | | | | | | |

TABLE 14-continued

| | | | | | |
|---|---|---|---|---|---|
| Comparative electrolytic solution No. 16-4 | — | Synthesis Example 2 (5a-Tetra) | 0.132 | — | — | — |
| Comparative electrolytic solution No. 16-5 | — | Synthesis Example 2 (5a-Tetra) | 0.132 | — | — | — |
| Comparative electrolytic solution No. 16-6 | — | Synthesis Example 2 (5a-Tetra) | 0.132 | — | — | — |
| Comparative electrolytic solution No. 16-7 | — | Synthesis Example 2 (5a-Tetra) | 0.132 | — | — | — |
| Comparative electrolytic solution No. 16-8 | — | Synthesis Example 2 (5a-Tetra) | 0.132 | — | — | — |
| Comparative electrolytic solution No. 16-9 | — | Synthesis Example 2 (5a-Tetra) | 0.132 | — | — | — |
| Comparative electrolytic solution No. 16-10 | — | Synthesis Example 2 (5a-Tetra) | 0.132 | — | — | — |

Example 16 and Comparative Example 16—Production and Evaluation of Nonaqueous Electrolytic Solution Batteries A test (mixture of artificial graphite+natural graphite) negative electrode was produced as described below using a negative-electrode active material in which an artificial graphite is mixed with natural graphite instead of the negative-electrode active material (an amorphous carbon powder) used in the nonaqueous electrolytic solution batteries according to Example 15 as described above.

Production of Test (Mixture of Artificial Graphite+Natural Graphite) Negative Electrode An SCMG®-AR powder from Showa Denko K. K. as artificial graphite and natural graphite particles (the mean particle size: 25 μm) from Kansai Coke and Chemicals Company, Limited. as natural graphite were uniformly dispersed and mixed into NMP in which PVDF as a binding agent was pre-dissolved, and NMP for adjusting the viscosity was then further added to prepare a mixture paste of (artificial graphite+natural graphite) mixture. The above paste was applied to a copper foil (current collector), dried, and pressurized. Then the copper foil was processed into a predetermined size to obtain a test (mixture of artificial graphite+natural graphite) negative electrode. The ratio of solid contents in the negative electrode was artificial graphite powder:natural graphite powder:PVDF=72:18:10 (by the mass ratio).

Production of Nonaqueous Electrolytic Solution Batteries

Aluminum laminate housing cells (with a capacity of 30 mAh) including the above test NMC positive electrode, the test (mixture of artificial graphite+natural graphite) negative electrode, and a microporous polypropylene-polyethylene double layered separator were each impregnated with one of the various nonaqueous electrolytic solutions and the various comparative nonaqueous electrolytic solutions shown in Table 14 to produce the nonaqueous electrolytic solution batteries according to Example 16 and Comparative Example 16 in a similar way as in Example 15 and Comparative Example 15 as described above.

Production of Nonaqueous Electrolytic Solution Batteries

Each of these nonaqueous electrolytic solution batteries was subjected to the following evaluations as described above as in Example 1 above.

Evaluation 1: Low-temperature property (0° C.) after 500 cycles at 60° C.

Evaluation 2: 5C-rate characteristic after 500 cycles at 60° C.

Evaluation 3: Low-temperature property (0° C.) after stored at 60° C.

Various evaluations of the nonaqueous electrolytic solution batteries according to Example 16 and Comparative Example 16 are shown in Table 15 as relative values when the corresponding evaluation results of the nonaqueous electrolytic solution battery according to Comparative Example 16-1 are taken as 100.

TABLE 15

| | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 16-1 | Electrolytic solution No.16-1 | 135.6 | 129.5 | 125.1 |
| Example 16-2 | Electrolytic solution No.16-2 | 135.6 | 128.8 | 124.8 |
| Example 16-3 | Electrolytic solution No.16-3 | 134.6 | 129.4 | 124.4 |
| Example 16-4 | Electrolytic solution No.16-4 | 135.2 | 129.8 | 124.9 |
| Example 16-5 | Electrolytic solution No.16-5 | 134.6 | 128.8 | 124.2 |
| Example 16-6 | Electrolytic solution No.16-6 | 134.4 | 128.5 | 123.9 |
| Example 16-7 | Electrolytic solution No.16-7 | 133.8 | 128.1 | 123.3 |
| Example 16-8 | Electrolytic solution No.16-8 | 134.4 | 128.6 | 123.8 |
| Comparative Example 16-1 | Comparative electrolytic solution No.16-1 | 100.0 | 100.0 | 100.0 |
| Comparative Example 16-2 | Comparative electrolytic solution No.16-2 | 123.1 | 115.9 | 113.1 |
| Comparative Example 16-3 | Comparative electrolytic solution No.16-3 | 126.1 | 115.8 | 116.4 |
| Comparative Example 16-4 | Comparative electrolytic solution No.16-4 | 126.1 | 115.3 | 116.1 |
| Comparative Example 16-5 | Comparative electrolytic solution No.16-5 | 125.2 | 115.7 | 115.7 |
| Comparative Example 16-6 | Comparative electrolytic solution No.16-6 | 125.7 | 116.1 | 116.3 |

TABLE 15-continued

|  | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Comparative Example 16-7 | Comparative electrolytic solution No.16-7 | 125.1 | 115.2 | 115.6 |
| Comparative Example 16-8 | Comparative electrolytic solution No.16-8 | 125.0 | 114.9 | 115.3 |
| Comparative Example 16-9 | Comparative electrolytic solution No.16-9 | 124.4 | 114.6 | 114.8 |
| Comparative Example 16-10 | Comparative electrolytic solution No.16-10 | 125.0 | 117.8 | 115.2 |

(Positive electrode; NMC, Negative electrode; Mixture of artificial graphite + natural graphite)

Example 16

As seen from the results in Table 15, Example 16 showed a similar tendency as Example 15. That is, even in a case where a mixed powder of artificial graphite and natural graphite was used as a negative-electrode active material, Example 16 was superior to Comparative Example 16 in various evaluation results.

Example 17—Negative Electrode $SiO_x$ Negative Electrode Preparation of Nonaqueous Electrolytic Solutions Nos. 17-1 to 17-8 and Comparative Electrolytic Solutions Nos. 17-2 to 17-11

In a dry box under a nitrogen atmosphere of a dew point of −50° C. or less, $LiPF_6$ as an electrolyte was dissolved and prepared in a preheated and dissolved nonaqueous solvent of EC and EMC, and FEC as the group (II) compound described above (volume ratio 20:70:10/mass ratio 23.6:63.1:13.3) so that the concentration of $LiPF_6$ was 1.2 mol/liter, and then various ionic complex/EMC solutions according to the present invention, and the group (II), group (III), group (IV), and group (V) compounds described above were added each in a predetermined amount as shown in Table 16 to prepare the nonaqueous electrolytic solutions Nos. 17-1 to 17-8 according to the present invention and comparative electrolytic solutions Nos. 17-2 to 17-11.

Preparation of Comparative Electrolytic Solution No. 17-1

Comparative electrolytic solution No. 17-1 was prepared as Comparative Example. In a dry box under a nitrogen atmosphere of a dew point of −50° C. or less, $LiPF_6$ as an electrolyte was dissolved and prepared in a preheated and dissolved nonaqueous solvent of EC and EMC (volume ratio 30:70/mass ratio 35.9:64.1) so that the concentration of $LiPF_6$ was 1.2 mol/liter to prepare the comparative electrolytic solution No. 17-1. It is noted that the comparative electrolytic solution No. 17-1 was prepared in the same way as in the nonaqueous electrolytic solutions 17-1 to 17-8 according to the present invention except that the various ionic complex/EMC solutions and the group (II) compounds shown in Table 16 as shown below were not added.

TABLE 16

| Electrolytic solution No, | Li salt $LiPF_6$ (mol/liter) | Nonaqueous solvent | | Group (V) compound 1 | Content (mass %) | Group (I) compound | | Group (II) compound | Content (mass %) |
|---|---|---|---|---|---|---|---|---|---|
| | | EC (mass %) | EMC (mass %) | | | (Cis isomer) | Content (mass %) | | |
| Electrolytic solution No. 17-1 | 1.2 | 23.6 | 63.1 | FEC | 13.3 | Synthesis Example 1 (1a-Cis) | 1.2 | 1,3-PS | 2.4 |
| Electrolytic solution No. 17-2 | | | | | | | | 1,3-PRS | 1.2 |
| Electrolytic solution No. 17-3 | | | | | | | | Formula (II-2a-4) | 1.2 |
| Electrolytic solution No. 17-4 | | | | | | | | Formula (II-3a-1) | 1.2 |
| Electrolytic solution No. 17-5 | | | | | | | | Formula (II-3a-15) | 1.2 |
| Electrolytic solution No. 17-6 | | | | | | | | Butane-DMS | 1.2 |
| Electrolytic solution No. 17-7 | | | | | | | | Succinonitrile | 1.2 |
| Electrolytic solution No. 17-8 | | | | | | | | Formula (II-3b-1) | 1.2 |
| Comparative electrolytic solution No. 17-1 | 1.2 | 35.9 | 64.1 | — | — | — | — | — | — |
| Comparative electrolytic solution No. 17-2 | 1.2 | 23.6 | 63.1 | FEC | 13.3 | — | — | — | — |

TABLE 16-continued

| | | | | | | | |
|---|---|---|---|---|---|---|---|
| Comparative electrolytic solution No. 17-3 | | | Synthesis Example 1 (1a-Cis) | 1.2 | — | | — |
| Comparative electrolytic solution No. 17-4 | | | — | — | 1,3-PS | | 2.4 |
| Comparative electrolytic solution No. 17-5 | | | — | — | 1,3-PRS | | 1.2 |
| Comparative electrolytic solution No. 17-6 | | | — | — | Formula (II-2a-4) | | 1.2 |
| Comparative electrolytic solution No. 17-7 | | | — | — | Formula (II-3a-1) | | 1.2 |
| Comparative electrolytic solution No. 17-8 | | | — | — | Formula (II-3a-15) | | 1.2 |
| Comparative electrolytic solution No. 17-9 | | | — | — | Butane-DMS | | 1.2 |
| Comparative electrolytic solution No. 17-10 | | | — | — | Succinonitrile | | 1.2 |
| Comparative electrolytic solution No. 17-11 | | | — | — | Formula (II-3b-1) | | 1.2 |

| Electrolytic solution No. | Group (III) compound Trans isomer | Content (mass %) | Trans isomer/ Cis isomer | Group (IV) compound Tetrafluoro Comdex | Content (mass %) | Tetrafluoro complex/ Cis isomer | Group (V) compound 2 | Content (mass %) |
|---|---|---|---|---|---|---|---|---|
| Electrolytic solution No. 17-1 | Synthesis Example 1 (1a-Trans) | 0.006 | 0.005 | Synthesis Example 2 (5a-Tetra) | 0.144 | 0.12 | VC | 1.0 |
| Electrolytic solution No. 17-2 | | | | | | | | |
| Electrolytic solution No. 17-3 | | | | | | | | |
| Electrolytic solution No. 17-4 | | | | | | | | |
| Electrolytic solution No. 17-5 | | | | | | | | |
| Electrolytic solution No. 17-6 | | | | | | | | |
| Electrolytic solution No. 17-7 | | | | | | | | |
| Electrolytic solution No. 17-8 | | | | | | | | |
| Comparative electrolytic solution No. 17-1 | — | — | — | — | — | — | — | — |
| Comparative electrolytic solution No. 17-2 | — | — | — | — | — | — | — | — |
| Comparative electrolytic solution No. 17-3 | — | — | — | — | — | — | — | — |

TABLE 16-continued

| | | | | | | | | |
|---|---|---|---|---|---|---|---|---|
| Comparative electrolytic solution No. 17-4 | Synthesis Example 1 (1a-Trans) | 1.2 | — | Synthesis Example 2 (5a-Tetra) | 0.144 | — | VC | 1.0 |
| Comparative electrolytic solution No. 17-5 | | | | | | | | |
| Comparative electrolytic solution No. 17-6 | | | | | | | | |
| Comparative electrolytic solution No. 17-7 | | | | | | | | |
| Comparative electrolytic solution No. 17-8 | | | | | | | | |
| Comparative electrolytic solution No. 17-9 | | | | | | | | |
| Comparative electrolytic solution No. 17-10 | | | | | | | | |
| Comparative electrolytic solution No. 17-11 | | | | | | | | |

Example 17 and Comparative Example 17—Production and Evaluation of Nonaqueous Electrolytic Solution Batteries A test $SiO_x$ negative electrode was produced as described below using a powder mixture of a silicon oxide powder and an aggregated artificial graphite powder as a negative-electrode active material in place of the negative-electrode active material (a powder mixture of artificial graphite and natural graphite) used in the nonaqueous electrolytic solution batteries according to Example 16.

Production of $SiO_x$ Negative Electrode

A powder mixture of a silicon oxide powder disproportioned by heat treatment ($SiO_x$ wherein x is 0.3 to 1.6, the mean particle size: 5 µm, Sigma Aldrich Japan, Co. LLC.) as a silicon oxide powder and MAG-D (the particle size: 20 µm or less) from Hitachi Chemical Co., Ltd. as an aggregated artificial graphite powder was uniformly dispersed and mixed into NMP in which PVDF as a binding agent was pre-dissolved, and Ketjen black (electrically conductive agent) was further added and mixed, and NMP for adjusting the viscosity was then further added to prepare an $SiO_x$ mixture paste.

The above paste was applied to a copper foil (current collector), dried, and pressurized. Then the copper foil was processed into a predetermined size to obtain a test $SiO_x$ negative electrode. The ratio of solid contents in the negative electrode was $SiO_x$:MAG-D:electrically conductive agent:PVDF=35:47:8:10 (by the mass ratio).

It is noted that the amounts of the NMC positive-electrode active material and the $SiO_x$ powder were adjusted so that the charging capacity of the $SiO_x$ negative electrode is larger than that of the NMC positive electrode, and the applied amount was also adjusted so that a lithium metal does not deposit on the $SiO_x$ negative electrode during charging.

Production of Nonaqueous Electrolytic Solution Batteries

Aluminum laminate housing cells (with a capacity of 30 mAh) including the above test NMC positive electrode, the test $SiO_x$ negative electrode, and a microporous polypropylene-polyethylene double layered separator were each impregnated with one of the various nonaqueous electrolytic solutions and the various comparative nonaqueous electrolytic solutions shown in Table 16 to produce the nonaqueous electrolytic solution batteries according to Example 17 and Comparative Example 17 in a similar way as in Example 16 and Comparative Example 16 as described above It is noted that the microporous polypropylene-polyethylene double layered separator was arranged so that the polypropylene side thereof is positioned in the side of the positive electrode to allow the positive electrode to face the negative electrode.

Evaluation of Nonaqueous Electrolytic Solution Batteries

Evaluation 1: Low-Temperature Property (0° C.) after 200 Cycles at 60° C.

Each of the nonaqueous electrolytic solution batteries according to Example 17 and Comparative Example 17 was evaluated as described below.

First, conditioning was performed at an environmental temperature of 25° C. under the following conditions. That is, constant-current and constant-voltage charge was performed as the initial charge/discharge at an environmental temperature of 25° C. using the produced cells to a charge upper limit voltage of 4.2 V at a 0.05 C rate (1.5 mA), and discharge was performed at a constant current of a 0.1 C rate (3 mA) to a discharge cutoff voltage of 2.5 V. Subsequently, the following charge-discharge cycle was repeated for 5 times: constant-current and constant-voltage charge was performed at a 0.1 C rate (3 mA) to a charge upper limit voltage of 4.2 V, and discharge was performed at a constant current of a 0.1 C rate (3 mA) to a discharge cutoff voltage of 2.5 V.

After this conditioning, the following charge-discharge cycle was repeated for 3 times at an environmental temperature of 25° C.: constant-current and constant-voltage charge was performed at 0.2 C rate (6 mA) to a charge upper limit voltage of 4.2 V, and discharge was then performed at a constant current of a 0.2 C rate (6 mA) to a discharge cutoff voltage of 2.5 V.

Then, charge/discharge tests were performed at an environmental temperature of 60° C. The following charge-discharge cycle was repeated for 200 times: constant-current and constant-voltage charge was performed at a 1 C rate (30 mA) to a charge upper limit voltage of 4.2 V, and discharge was performed at a constant current of a 2 C rate (60 mA) to a discharge cutoff voltage of 2.5 V.

Next, the nonaqueous electrolytic solution batteries were cooled to 25° C., and again discharged to 2.5 V. Then constant-current and constant-voltage charge was performed to 4.2 V at a 0.2 C rate at 0° C. Further, discharge was performed at a constant current of a 3 C rate (900 mA) to a discharge cutoff voltage of 2.5 V while maintaining the temperature at 0° C., and the capacity obtained at that time was taken as the low-temperature property (0° C.) after stored at 60° C.

Various evaluations of the nonaqueous electrolytic solution batteries according to Example 17 and Comparative Example 17 are shown in Table 17 as relative values when various evaluations of the nonaqueous electrolytic solution battery according to Comparative Example 17-1 are taken as 100.

TABLE 17

| | Electrolytic solution No, | Low-temperature property (0° C.) after prolonged cycles at 60° C. | 3C-rate characteristic (25° C.) after prolonged cycles at 60° C. | Low-temperature property (0° C.) after stored at 60° C. |
|---|---|---|---|---|
| Example 17-1 | Electrolytic solution No.17-1 | 133.5 | 127.5 | 123.2 |
| Example 17-2 | Electrolytic solution No.17-2 | 133.1 | 126.4 | 122.4 |
| Example 17-3 | Electrolytic solution No.17-3 | 131.5 | 126.4 | 121.5 |
| Example 17-4 | Electrolytic solution No.17-4 | 132.7 | 127.3 | 122.6 |
| Example 17-5 | Electrolytic solution No.17-5 | 132.0 | 126.4 | 121.9 |
| Example 17-6 | Electrolytic solution No.17-6 | 131.4 | 125.6 | 121.1 |
| Example 17-7 | Electrolytic solution No.17-7 | 130.1 | 124.6 | 120.0 |
| Example 17-8 | Electrolytic solution No.17-8 | 130.6 | 125.0 | 120.4 |
| Comparative Example 17-1 | Comparative electrolytic solution No.17-1 | 100.0 | 100.0 | 100.0 |
| Comparative Example 17-2 | Comparative electrolytic solution No.17-2 | 113.0 | 106.9 | 105.2 |
| Comparative Example 17-3 | Comparative electrolytic solution No.17-3 | 115.3 | 110.4 | 107.2 |
| Comparative Example 17-4 | Comparative electrolytic solution No.17-4 | 127.6 | 121.9 | 117.7 |
| Comparative Example 17-5 | Comparative electrolytic solution No.17-5 | 127.2 | 120.8 | 117.0 |
| Comparative Example 17-6 | Comparative electrolytic solution No.17-6 | 125.7 | 120.8 | 116.1 |
| Comparative Example 17-7 | Comparative electrolytic solution No.17-7 | 126.8 | 121.7 | 117.1 |
| Comparative Example 17-8 | Comparative electrolytic solution No.17-8 | 126.2 | 120.8 | 116.5 |
| Comparative Example 17-9 | Comparative electrolytic solution No.17-9 | 125.6 | 120.1 | 115.8 |
| Comparative Example 17-10 | Comparative electrolytic solution No.17-10 | 124.3 | 119.1 | 114.6 |
| Comparative Example 17-11 | Comparative electrolytic solution No.17-11 | 125.3 | 119.9 | 115.5 |

(Positive electrode; NMC, Negative electrode; $SiO_x$ negative electrode)

constant-current and constant-voltage charge was performed to 4.2 V at a 0.2 C rate at 0° C. Further, discharge was performed at a constant current of a 3 C rate (90 mA) to a discharge cutoff voltage of 2.5 V, and the capacity obtained at that time was taken as the low-temperature property (0° C.) after prolonged cycles at 60° C.

Evaluation 2: 3C-Rate Characteristic after 200 Cycles at 60° C.

After performing 200 cycles at an environmental temperature of 60° C. in Evaluation 1 as described above, the nonaqueous electrolytic solution batteries were cooled to 25° C., and then again discharged to 2.5 V. Subsequently, constant-current and constant-voltage charge was performed to 4.2 V at a 0.1 C rate at 25° C. Further, discharge was performed at a constant current of a 3 C rate (90 mA) to a discharge cutoff voltage of 2.5 V, and the capacity obtained at that time was taken as the 3C-rate characteristic (25° C.) after prolonged cycles at 60° C.

Evaluation 3: Low-Temperature Property (0° C.) after Stored at 60° C.

Each of the nonaqueous electrolytic solution batteries according to Example 17 and Comparative Example 17 was subjected to storage tests (stored for 10 days after charged to 4.2 V) at an environmental temperature of 60° C.

Example 17

As seen from the results shown in Table 17, even when the powder mixture of a silicon oxide powder and an aggregated artificial graphite powder was used in place of the powder mixture of artificial graphite and natural graphite as a negative-electrode active material, Example 17 was superior to Comparative Example 17 in various evaluation results.

Example 18 and Comparative Example 18—Production and Evaluation of Nonaqueous Electrolytic Solution Batteries A test Si negative electrode was produced as described below using an Si powder as a negative-electrode active material in place of the negative-electrode active material (a powder mixture of a silicon oxide powder and an aggregated artificial graphite powder) used in the nonaqueous electrolytic solution batteries according to Example 17.

Production of Test Si Negative Electrode

An Si powder (a powder mixture with the mean particle size: 10 μm/6 μm=9/1 by the mass ratio) as an Si powder was uniformly dispersed and mixed into NMP in which PVDF as a binding agent was pre-dissolved, and Ketjen black (electrically conductive agent 1) and vapor-grown carbon fiber (VGCF®-H, Showa Denko K. K.) (electrically conductive agent 2) were further added and mixed, and NMP for adjusting the viscosity was then further added to prepare an Si mixture paste.

The above paste was applied to a copper foil (current collector), dried, and pressurized. Then the copper foil was processed into a predetermined size to obtain a test Si negative electrode. The ratio of solid contents in the negative electrode was Si powder:electrically conductive agent 1:electrically conductive agent 2:PVDF=78:7:3:12 (by the mass ratio).

It is noted that the amounts of the NMC positive-electrode active material and the Si powder were adjusted so that the charging capacity of the Si negative electrode is larger than that of the NMC positive electrode, and the applied amount was adjusted so that a lithium metal does not deposit on the Si negative electrode during charging.

Production of Nonaqueous Electrolytic Solution Batteries

Aluminum laminate housing cells (with a capacity of 30 mAh) including the above test NMC positive electrode, the test Si negative electrode, and a microporous polypropylene-polyethylene double layered separator were each impregnated with one of the various nonaqueous electrolytic solutions and the various comparative nonaqueous electrolytic solutions shown in Table 16 to produce the nonaqueous electrolytic solution batteries according to Example 18 and Comparative Example 18 as in Example 17 and Comparative Example 17 described above.

Example 18 and Comparative Example 18

Evaluation of Nonaqueous Electrolytic Solution Batteries

The following evaluations were performed as described above with regard to the nonaqueous electrolytic solution batteries according to the aforementioned Example 17.
Evaluation 1: Low-temperature property (0° C.) after 200 cycles at 60° C.
Evaluation 2: 3C-rate characteristic after 200 cycles at 60° C.
Evaluation 3: Low-temperature property (0° C.) after stored at 60° C.

Various evaluations of the nonaqueous electrolytic solution batteries according to Example 18 and Comparative Example 18 are shown in Table 18 as relative values when the corresponding evaluation results of the nonaqueous electrolytic solution battery according to Comparative Example 18-1 are taken as 100.

Example 18

As seen from the results shown in Table 18, even when the powder mixture of a silicon oxide powder was used as a negative-electrode active material, Example 18 was superior to Comparative Example 18 in various evaluation results.

Example 19—Negative Electrode

LTO Negative Electrode Preparation of Nonaqueous Electrolytic Solutions Nos. 19-1 to 19-8 and Comparative Electrolytic Solutions Nos. 19-2 to 24-9

In a dry box under a nitrogen atmosphere of a dew point of −50° C. or less, $LiPF_6$ and $LiPF_4$ as electrolytes were dissolved and prepared in a nonaqueous solvent of PC and EMC (volume ratio 30:70/mass ratio 33.8:66.2) so that the concentrations of $LiPF_6$ and $LiPF_4$ were 1.1 mol/liter and 0.4 mol/liter, respectively, and then the various ionic complex/EMC solutions according to the present invention and the group (II) compounds described above were added each in a predetermined amount as shown in Table 19 to prepare the nonaqueous electrolytic solutions Nos. 19-1 to 19-8 according to the present invention and the comparative electrolytic solutions Nos. 19-2 to 19-9.

Preparation of Comparative Electrolytic Solution No. 19-1

Comparative electrolytic solution No. 19-1 was prepared as Comparative Example.

In a dry box under a nitrogen atmosphere of a dew point of −50° C. or less, $LiPF_6$ and $LiPF_4$ as electrolytes were dissolved and prepared in a nonaqueous solvent of PC and EMC (volume ratio 30:70/mass ratio 33.8:66.2) so that the concentrations of $LiPF_6$ and $LiPF_4$ were 1.1 mol/liter and 0.4 mol/liter, respectively, to prepare the comparative electrolytic solution No. 19-1. It is noted that the comparative electrolytic solution No. 19-1 was prepared in the same way as in the nonaqueous electrolytic solutions 19-1 to 19-8 according to the present invention except that the various ionic complex/EMC solutions, the aforementioned group (II) compounds shown in Table 19 below were not added.

TABLE 18

|  | Electrolytic solution No, | Low-temperature property (0° C.) after prolonged cycles at 60° C. | 3C-rate characteristic (25° C.) after prolonged cycles at 60° C. | Low-temperature property (0° C.) after stored at 60° C. |
| --- | --- | --- | --- | --- |
| Example 18-1 | Electrolytic solution No.17-1 | 130.2 | 124.3 | 120.1 |
| Example 18-2 | Electrolytic solution No.17-2 | 129.7 | 123.3 | 119.4 |
| Example 18-3 | Electrolytic solution No.17-3 | 128.3 | 123.2 | 118.5 |
| Example 18-4 | Electrolytic solution No.17-4 | 129.3 | 124.1 | 119.5 |
| Example 18-5 | Electrolytic solution No.17-5 | 128.7 | 123.2 | 118.8 |
| Example 18-6 | Electrolytic solution No.17-6 | 128.1 | 122.5 | 118.1 |
| Example 18-7 | Electrolytic solution No.17-7 | 126.9 | 121.5 | 117.0 |
| Example 18-8 | Electrolytic solution No.17-8 | 127.3 | 121.8 | 117.4 |
| Comparative Example 18-1 | Comparative electrolytic solution No.17-1 | 100.0 | 100.0 | 100.0 |
| Comparative Example 18-2 | Comparative electrolytic solution No.17-2 | 110.1 | 104.1 | 102.5 |
| Comparative Example 18-3 | Comparative electrolytic solution No.17-3 | 112.4 | 107.6 | 104.4 |
| Comparative Example 18-4 | Comparative electrolytic solution No.17-4 | 124.4 | 118.8 | 114.8 |
| Comparative Example 18-5 | Comparative electrolytic solution No.17-5 | 124.0 | 117.8 | 114.1 |
| Comparative Example 18-6 | Comparative electrolytic solution No.17-6 | 122.6 | 117.8 | 113.2 |
| Comparative Example 18-7 | Comparative electrolytic solution No.17-7 | 123.6 | 118.7 | 114.2 |
| Comparative Example 18-8 | Comparative electrolytic solution No.17-8 | 123.0 | 117.8 | 113.6 |
| Comparative Example 18-9 | Comparative electrolytic solution No.17-9 | 122.4 | 117.0 | 112.9 |
| Comparative Example 18-10 | Comparative electrolytic solution No.17-10 | 121.2 | 116.1 | 111.8 |
| Comparative Example 18-11 | Comparative electrolytic solution No.17-11 | 122.1 | 116.9 | 112.6 |

(Positive electrode; NMC, Negative electrode; Si negative electrode)

TABLE 19

| Electrolytic solution No. | Group (I) compound (Cis isomer) | Content (mass %) | Group (II) compound | Content (mass %) | Group (II) compound 2 | Content (mass %) | Trans isomer | Content (mass %) | Trans isomer/Cis isomer (mass ratio) | Tetrafluoro complex | Content (mass %) | Tetrafluoro complex/Cis isomer (mass ratio) |
|---|---|---|---|---|---|---|---|---|---|---|---|---|
| Electrolytic solution No. 19-1 | Synthesis Example 1 (1a-Cis) | 1.2 | TMSP | 1.0 | — | — | Synthesis Example 1 (1a-Trans) | 0.005 | 0.004 | Synthesis Example 2 (5a-Tetra) | 0.144 | 0.12 |
| Electrolytic solution No. 19-2 | | | | | 1,3-PS | 2.0 | | 0.005 | 0.004 | | 0.144 | 0.12 |
| Electrolytic solution No. 19-3 | | | | | 1,3-PRS | 1.0 | | 0.005 | 0.004 | | 0.144 | 0.12 |
| Electrolytic solution No. 19-4 | | | | | Formula (II-2a-4) | 1.0 | | 0.005 | 0.004 | | 0.144 | 0.12 |
| Electrolytic solution No. 19-5 | | | | | Formula (II-3a-1) | 1.0 | | 0.005 | 0.004 | | 0.144 | 0.12 |
| Electrolytic solution No. 19-6 | | | | | Formula (II-3a-15) | 1.0 | | 0.005 | 0.004 | | 0.144 | 0.12 |
| Electrolytic solution No. 19-7 | | | | | Formula (II-5a-1) | 1.0 | | 0.005 | 0.004 | | 0.144 | 0.12 |
| Electrolytic solution No. 19-8 | | | | | Formula (II-3b-1) | 1.0 | | 0.005 | 0.004 | | 0.144 | 0.12 |
| Comparative electrolytic solution No. 19-1 | — | — | — | — | — | — | — | — | — | — | — | — |
| Comparative electrolytic solution No. 19-2 | Synthesis Example 1 (1a-Cis) | 1.2 | — | — | — | — | Synthesis Example 1 (1a-Trans) | 0.005 | 0.004 | Synthesis Example 2 (5a-Tetra) | 0.144 | 0.12 |
| Comparative electrolytic solution No. 19-3 | — | — | TMSP | 1.0 | 1,3-PS | 2.0 | | 0.005 | — | | 0.144 | — |
| Comparative electrolytic solution No. 19-4 | — | — | — | — | 1,3-PRS | 1.0 | | 0.005 | — | | 0.144 | — |
| Comparative electrolytic solution No. 19-5 | — | — | — | — | Formula (II-2a-4) | 1.0 | | 0.005 | — | | 0.144 | — |
| Comparative electrolytic solution No. 19-6 | — | — | — | — | Formula (II-3a-1) | 1.0 | | 0.005 | — | | 0.144 | — |
| Comparative electrolytic solution No. 19-7 | — | — | — | — | Formula (II-3a-15) | 1.0 | | 0.005 | — | | 0.144 | — |
| Comparative electrolytic solution No. 19-8 | — | — | — | — | Formula (II-5a-1) | 1.0 | | | | | | |
| Comparative electrolytic solution No. 19-9 | — | — | — | — | Formula (II-3b-1) | 1.0 | | | | | | |

TABLE 19-continued

| | | | | |
|---|---|---|---|---|
| Comparative electrolytic solution No. 19-8 | 0.005 | — | 0.144 | — |
| Comparative electrolytic solution No. 19-9 | 0.005 | — | 0.144 | — |

Example 19 and Comparative Example 19

Production and Evaluation of Nonaqueous Electrolytic Solution Batteries

A test LTO-alloy negative electrode was produced as described below using a $Li_4Ti_5O_{12}$ (LTO) powder as a negative-electrode active material according to the following procedures.

Production of Test LTO Negative Electrode

An LTO powder (a powder mixture with the mean particle size: 0.90 μm/3.40 μm=9/1 by the mass ratio) as an $Li_4Ti_5O_{12}$ (LTO) powder was uniformly dispersed and mixed into NMP in which PVDF as a binding agent was pre-dissolved, and Ketjen black (electrically conductive agent 1) and vapor-grown carbon fiber (VGCF®-H, Showa Denko K. K.) (electrically conductive agent 2) were further added and mixed, and NMP for adjusting the viscosity was then further added to prepare an LTO mixture paste.

The resulting paste was applied to an aluminum foil (current collector), dried, and pressurized. Then the aluminum foil was processed into a predetermined size to obtain a test LTO negative electrode. The ratio of solid contents in the negative electrode was LTO powder:electrically conductive agent 1:electrically conductive agent 2:PVDF=83:5:2:10 (by the mass ratio).

Production of Nonaqueous Electrolytic Solution Batteries

Aluminum laminate housing cells (with a capacity of 30 mAh) including the above test NMC positive electrode, the test LTO negative electrode, and a cellulose separator were each impregnated with one of the various nonaqueous electrolytic solutions and the various comparative nonaqueous electrolytic solutions shown in Table 20 to produce the nonaqueous electrolytic solution batteries according to Examples 19-1 to 19-8 and Comparative Examples 19-1 to 19-9 as in Example 12 and Comparative Example 12 described above.

Evaluation of Nonaqueous Electrolytic Solution Batteries
Evaluation 1: Low-Temperature Property (0° C.) after 500 Cycles at 60° C.

Each of the nonaqueous electrolytic solution batteries according to Example 19 and Comparative Example 19 was evaluated as described below.

First, conditioning was performed at an environmental temperature of 25° C. under the following conditions. That is, constant-current and constant-voltage charge was performed as the initial charge/discharge at an environmental temperature of 25° C. using the produced cells to a charge upper limit voltage of 2.8 V at a 0.1 C rate (3 mA), and discharge was performed at a constant current of a 0.1 C rate (3 mA) to a discharge cutoff voltage of 1.5 V. Subsequently, the following charge-discharge cycle was repeated for 3 times: constant-current and constant-voltage charge was performed to a charge upper limit voltage of 2.8 V at a 0.1 C rate (3 mA), and discharge was performed at a constant current of a 0.1 C rate (3 mA) to a discharge cutoff voltage of 1.5 V.

After this conditioning, the following charge-discharge cycle was repeated for 3 times at an environmental temperature of 25° C.: constant-current and constant-voltage charge was performed at 0.2 C rate (6 mA) to a charge upper limit voltage of 2.8 V, and discharge was then performed at a constant current of a 0.2 C rate (6 mA) to a discharge cutoff voltage of 1.5 V.

Then, charge/discharge tests were performed at an environmental temperature of 60° C. The following charge-discharge cycle was repeated for 500 times: constant-current and constant-voltage charge was performed at a 2 C rate (30 mA) to a charge upper limit voltage of 2.8 V, and discharge was performed at a constant current of a 2 C rate (60 mA) to a discharge cutoff voltage of 1.5 V.

Next, the nonaqueous electrolytic solution batteries were cooled to 25° C., and again discharged to 1.5 V. Then constant-current and constant-voltage charge was performed to 2.8 V at a 0.2 C rate at 0° C. Further, discharge was performed at a constant current of a 5 C rate (150 mA) to a discharge cutoff voltage of 1.5 V, and the capacity obtained at that time was taken as the low-temperature property (0° C.) after prolonged cycles at 60° C.

Evaluation 2: 5C-Rate Characteristic after 500 Cycles at 60° C.

After performing 500 cycles at an environmental temperature of 60° C. in Evaluation 1 as described above, the nonaqueous electrolytic solution batteries were cooled to 25° C., and then again discharged to 1.5 V. Subsequently constant-current and constant-voltage charge was performed to 2.8 V at a 0.1 C rate at 25° C. Further, discharge was performed at a constant current of a 5 C rate (150 mA) to a discharge cutoff voltage of 1.5 V while maintaining the temperature at 25° C., and the capacity obtained at that time was taken as the 5C-rate characteristic (25° C.) after prolonged cycles at 60° C.

Evaluation 3: Low-Temperature Property (0° C.) after Stored at 60° C.

Each of the nonaqueous electrolytic solution batteries according to Example 19 and Comparative Example 19 was subjected to storage tests (stored for 10 days after charged to 2.8 V) at an environmental temperature of 60° C.

Next, the nonaqueous electrolytic solution batteries were cooled to 25° C., and again discharged to 1.5 V. Then constant-current and constant-voltage charge was performed to 2.8 V at a 0.2 C rate at 0° C. Further, discharge was performed at a constant current of a 5 C rate (150 mA) to a discharge cutoff voltage of 1.5 V while maintaining the temperature at 0° C., and the capacity obtained at that time was taken as the low-temperature property (0° C.) after stored at 60° C.

Various evaluations of the nonaqueous electrolytic solution batteries according to Example 19 and Comparative Example 19 are shown in Table 20 as relative values when various evaluations of the nonaqueous electrolytic solution battery according to Comparative Example 19-1 are taken as 100.

TABLE 20

|  | Electrolytic solution No, | Low-temperature property (0° C.) after prolonged cycles at 60° C. | 5C-rate characteristic (25° C.) after prolonged cycles at 60° C. | Low-temperature property (0° C.) after stored at 60° C. |
|---|---|---|---|---|
| Example 19-1 | Electrolytic solution No.19-1 | 135.2 | 129.5 | 124.5 |
| Example 19-2 | Electrolytic solution No.19-2 | 136.5 | 130.8 | 125.8 |
| Example 19-3 | Electrolytic solution No.19-3 | 136.8 | 131.1 | 126.0 |
| Example 19-4 | Electrolytic solution No.19-4 | 136.1 | 130.4 | 125.4 |
| Example 19-5 | Electrolytic solution No.19-5 | 136.4 | 130.7 | 125.6 |
| Example 19-6 | Electrolytic solution No.19-6 | 136.0 | 130.3 | 125.3 |
| Example 19-7 | Electrolytic solution No.19-7 | 135.7 | 130.0 | 125.0 |
| Example 19-8 | Electrolytic solution No.19-8 | 135.9 | 130.1 | 125.1 |
| Comparative Example 19-1 | Comparative electrolytic solution No.19-1 | 100.0 | 100.0 | 100.0 |
| Comparative Example 19-2 | Comparative electrolytic solution No.19-2 | 125.6 | 115.8 | 115.6 |
| Comparative Example 19-3 | Comparative electrolytic solution No.19-3 | 126.9 | 116.9 | 116.7 |
| Comparative Example 19-4 | Comparative electrolytic solution No.19-4 | 127.2 | 117.2 | 117.0 |
| Comparative Example 19-5 | Comparative electrolytic solution No.19-5 | 126.5 | 116.6 | 116.4 |
| Comparative Example 19-6 | Comparative electrolytic solution No.19-6 | 126.8 | 116.8 | 116.6 |
| Comparative Example 19-7 | Comparative electrolytic solution No.19-7 | 126.4 | 116.5 | 116.3 |
| Comparative Example 19-8 | Comparative electrolytic solution No.19-8 | 126.2 | 116.2 | 116.0 |
| Comparative Example 19-9 | Comparative electrolytic solution No.19-9 | 126.3 | 116.3 | 116.1 |

(Positive electrode; NMC, Negative electrode; LTO negative electrode)

Example 19

As seen from the results shown in Table 20, even when LTO was used as a negative-electrode active material, Example 19 was superior to Comparative Example 19 in various evaluation results.

The above results demonstrated that the nonaqueous electrolytic solutions according to the present invention can show similar effects as Example 1-1 to 1-56 in any of the cases where the following materials were used as a negative electrode: a carbon material having a d value in the lattice plane (002) of more than 0.340 nm as determined by X ray diffraction; a carbon material having a d value in the lattice plane (002) of 0.340 nm or less as determined by X ray diffraction; an oxide of one or more metals selected from Si, Sn, and Al; one or more metals selected from Si, Sn, and Al or an alloy comprising the one or more metals, or an alloy of lithium and the one or more metals or the alloy; and a lithium titanium oxide.

That is, it is clear that the nonaqueous electrolytic solution according to the present invention and a battery including the nonaqueous electrolytic solution according to the present invention have effects of improving cycle characteristics regardless of the types of negative electrodes as in the case of the positive electrode described above.

The invention claimed is:

1. An electrolytic solution for nonaqueous electrolytic solution secondary batteries, the electrolytic solution comprising:
a nonaqueous solvent,
an electrolyte dissolved in the nonaqueous solvent,
(I) a difluoro ionic complex (1) represented by the general formula (1), and
(II) at least one compound selected from the group consisting of cyclic sulfonic acid ester, cyclic sulfonic acid ester having an unsaturated bond, cyclic sulfuric acid ester, cyclic disulfonic acid ester, chain disulfonic acid ester, cyclic disulfonic acid anhydride, nitrile group-containing compound, silyl phosphate ester derivative, and silyl borate ester derivative:
wherein 95 mol % or more of the difluoro ionic complex (1) is a difluoro ionic complex (1-Cis) in a cis conformation represented by the general formula (1-Cis),

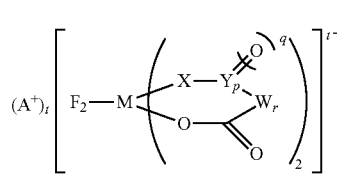
(1)

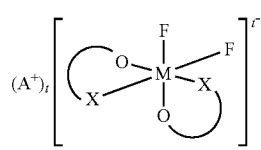
(1-Cis)

wherein in (1-Cis),

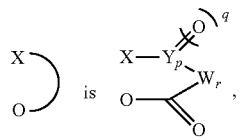

wherein in the general formulas (1) and (1-Cis), A⁺ is any one selected from the group consisting of a metal ion, a proton, and an onium ion, and M is any one selected from the group consisting of Si, P, As, and Sb;
F is a fluorine atom; O is an oxygen atom;
t is 2 when M is Si, and t is 1 when M is P, As, or Sb;
X is an oxygen atom or —N(R¹)—; N is a nitrogen atom; R₁ is a hydrocarbon group having 1 to 10 carbon atoms and optionally having a hetero atom and/or a halogen atom (the hydrocarbon group optionally having a branched-chain or ring structure when the number of carbon atoms is 3 or more);
when X is —N(R¹)—, and p is 0, X and W are bonded directly and optionally form a structure as shown in the general formulas (1-Cis-1) to (1-Cis-3) below; in the case of the general formula (1-Cis-2) below where the direct bond is a double bond, R¹ is not present;

Y is a carbon atom or a sulfur atom; q is 1 when Y is a carbon atom, and q is 1 or 2 when Y is a sulfur atom;

W represents a hydrocarbon group having 1 to 10 carbon atoms and optionally having a hetero atom and/or a halogen atom (the hydrocarbon group optionally having a branched-chain or ring structure when the number of carbon atoms is 3 or more), or —N(R$^2$)—; wherein, R$^2$ represents a hydrogen atom, an alkaline metal, or a hydrocarbon group having 1 to 10 carbon atoms and optionally having a hetero atom and/or a halogen atom; when the number of carbon atoms is 3 or more, R$^2$ optionally has a branched-chain or ring structure; and p is 0 or 1, q is an integer of 0 to 2, r is an integer of 0 to 2, and p+r≥1:

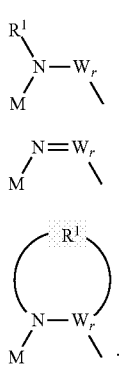

(1-Cis-1)

(1-Cis-2)

(1-Cis-3)

2. The electrolytic solution according to claim 1, wherein in a case where the compound stated in the (II) comprises the cyclic sulfonic acid ester, the cyclic sulfonic acid ester is represented by the formula (II-1a),
in a case where the compound stated in the (II) comprises the cyclic sulfonic acid ester having an unsaturated bond, the cyclic sulfonic acid ester having an unsaturated bond is represented by the formula (II-1b),
in a case where the compound stated in the (II) comprises the cyclic sulfuric acid ester, the cyclic sulfuric acid ester is represented by the formulae (II-2a) and/or (II-2b),
in a case where the compound stated in the (II) comprises the cyclic disulfonic acid ester, the cyclic disulfonic acid ester is represented by any one or more of the groups selected from the formulae (II-3a), (II-3b), and (II-3c),
in a case where the compound stated in the (II) comprises the chain disulfonic acid ester, the chain disulfonic acid ester is represented by the formulae (II-4a) and/or (II-4b),
in a case where the compound stated in the (II) comprises the cyclic disulfonic acid anhydride, the cyclic disulfonic acid anhydride is represented by the formula (II-5a),
in a case where the compound stated in the (II) comprises the nitrile group-containing compound, the nitrile group-containing compound is represented by the formula (II-6a),
in a case where the compound stated in the (II) comprises the silyl phosphate ester derivative, the silyl phosphate ester derivative is represented by the formula (II-7a), and
in a case where the compound stated in the (II) comprises the silyl borate ester derivative, the silyl borate ester derivative is represented by the formula (II-7b):

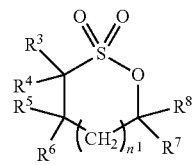

(II-1a)

wherein in the formula (II-1a), O represents an oxygen atom, S represents a sulfur atom, $n^1$ is an integer of 0 or more and 2 or less, and $R^3$, $R^4$, $R^5$, $R^6$, $R^7$, and $R^8$ are each independently a hydrogen atom, a substituted or unsubstituted alkyl group having 1 to 6 carbon atoms, or a substituted or unsubstituted fluoroalkyl group having 1 to 4 carbon atoms;

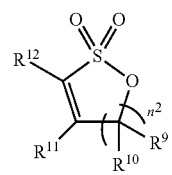

(II-1b)

wherein in the formula (II-1b), O represents an oxygen atom, S represents a sulfur atom, $n^2$ is an integer of 1 or more and 3 or less, and $R^9$, $R^{10}$, $R^{11}$, and $R^{12}$ are each independently a hydrogen atom, a substituted or unsubstituted alkyl group having 1 to 5 carbon atoms, or a substituted or unsubstituted fluoroalkyl group having 1 to 4 carbon atoms;

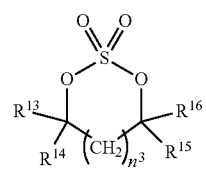

(II-2a)

wherein in the formula (II-2a), O represents an oxygen atom, S represents a sulfur atom, C represents a carbon atom, $n^3$ is an integer of 0 or more and 1 or less, and $R^{13}$, $R^{14}$, $R^{15}$, and $R^{16}$ are each independently a hydrogen atom, a substituted or unsubstituted alkyl group having 1 to 5 carbon atoms, a substituted or unsubstituted alkenyl group having 2 to 5 carbon atoms, a substituted or unsubstituted alkynyl group having 2 to 5 carbon atoms, or a substituted or unsubstituted fluoroalkyl group having 1 to 4 carbon atoms, provided that $R^{13}$ or $R^{14}$ and $R^{15}$ or $R^{16}$ optionally form a single bond with each other when $n^3$ is 0;

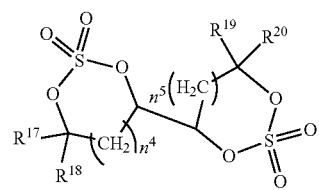

(II-2b)

wherein in the formula (II-2b), O represents an oxygen atom, S represents a sulfur atom, C represents a carbon atom, $n^4$ and $n^5$ are each an integer of 0 or more and 1 or less, and $R^{17}$, $R^{18}$, $R^{19}$, and $R^{20}$ are each independently a hydrogen atom, a substituted or unsubstituted alkyl group having 1 to 5 carbon atoms, or a substituted or unsubstituted fluoroalkyl group having 1 to 4 carbon atoms;

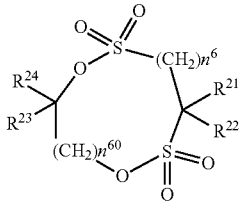

(II-3a)

wherein in the formula (II-3a), O represents an oxygen atom, S represents a sulfur atom, $n^6$ is an integer of 0 or more and 4 or less, and $R^{21}$ and $R^{22}$ are each independently a hydrogen atom, a halogen atom, or a substituted or unsubstituted alkyl group having 1 to 5 carbon atoms, $R^{23}$ and $R^{24}$ are each independently a hydrogen atom, a halogen atom, a substituted or unsubstituted alkyl group having 1 to 5 carbon atoms, or a substituted or unsubstituted fluoroalkyl group having 1 to 4 carbon atoms, and $n^{60}$ is an integer of 0 or more and 4 or less;

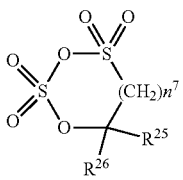

(II-3b)

wherein in the formula (II-3b), O represents an oxygen atom, S represents a sulfur atom, $n^7$ is an integer of 0 to 3, and $R^{25}$ and $R^{26}$ are each independently a hydrogen atom, a halogen atom, a substituted or unsubstituted alkyl group having 1 to 5 carbon atoms, or a substituted or unsubstituted fluoroalkyl group having 1 to 4 carbon atoms;

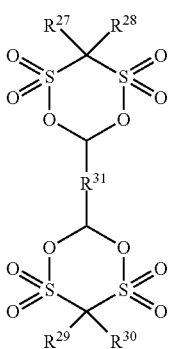

(II-3c)

wherein in the formula (II-3c), O represents an oxygen atom, S represents a sulfur atom, $R^{27}$, $R^{28}$, $R^{29}$ and $R^{30}$ are each independently a hydrogen atom, or a substituted or unsubstituted alkyl group having 1 to 5 carbon atoms, and $R^{31}$ is a substituted or unsubstituted alkyl group having 1 to 5 carbon atoms or a substituted or unsubstituted fluoroalkyl group having 1 to 4 carbon atoms;

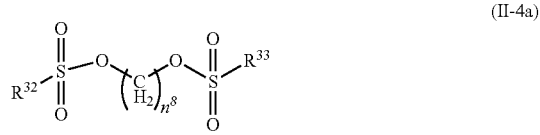

(II-4a)

wherein in the formula (II-4a), O represents an oxygen atom, S represents a sulfur atom, C represents a carbon atom, $n^8$ is an integer of 1 or more and 4 or less, and $R^{32}$ and $R^{33}$ are each independently an optionally branched alkyl group having 1 to 6 carbon atoms;

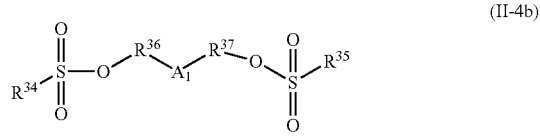

(II-4b)

wherein in the formula (II-4b), O represents an oxygen atom, S represents a sulfur atom, $R^{34}$ and $R^{35}$ are each independently an optionally branched alkyl group having 1 to 6 carbon atoms, $R^{36}$ and $R^{37}$ represent an unsubstituted methylene group or methylene group having an alkyl group having 1 to 4 carbon atoms, and Ai is a vinylene group, a 2-butenylene group, or an ethynylene group;

(II-5a)

wherein in the formula (II-5a), O represents an oxygen atom, S represents a sulfur atom, and $R^{38}$ is an alkylene group or fluorinated alkylene group having 2 to 4 carbon atoms, an alkenylene group or fluorinated alkenylene group having 2 to 4 carbon atoms, or an arylene group or a fluorinated arylene group;

NCR≡C—$R^{39}$—C≡N (II-6a)

wherein in the formula (II-6a), N represents a nitrogen atom, C represents a carbon atom, and $R^{39}$ is a compound represented by a linear or branched hydrocarbon chain having 1 to 10 carbon atoms;

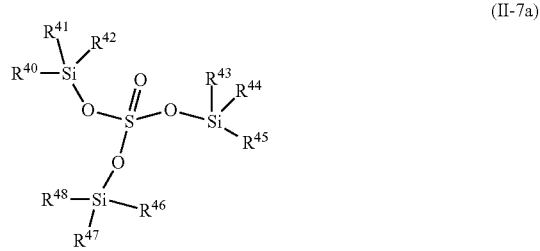

(II-7a)

wherein in the formula (II-7a), O represents an oxygen atom, P represents a phosphorus atom, Si represents a silicon atom, and $R^{40}$ to $R^{48}$ are each independently a hydrogen atom, or a substituted or unsubstituted alkyl group having 1 to 5 carbon atoms;

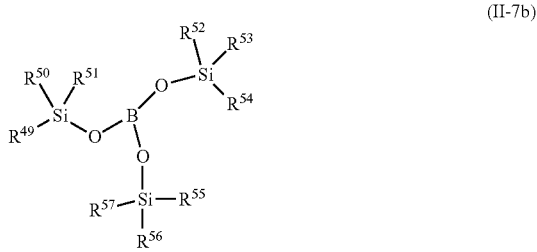

(II-7b)

wherein in the formula (II-7b), O represents an oxygen atom, B represents a boron atom, Si represents a silicon atom, and $R^{49}$ to $R^{57}$ are each independently a hydrogen atom, or a substituted or unsubstituted alkyl group having 1 to 5 carbon atoms.

3. The electrolytic solution according to claim 1, wherein elements in an anion moiety of the difluoro ionic complex (1-Cis) stated in the (I) are at least one combination selected from (Cis-a), (Cis-b), (Cis-c), and (Cis-d):
(Cis-a) M=P; X=O; Y=C; p, q, and t=1; and r=0;
(Cis-b) M=P; X=O; W=C(CF$_3$)$_2$; p and q=0; and r and t=1;
(Cis-c) M=Si; X=O; Y=C; p and q=1; t=2; and r=0; and
(Cis-d) M=P; X=N(R$^1$); Y=C; R$^1$=CH$_3$; p, q, and t=1; and r=0.

4. The electrolytic solution according to claim 1, wherein $A^+$ comprises one or more selected from the group consisting of a lithium ion, a sodium ion, a potassium ion, and a quaternary alkylammonium ion.

5. The electrolytic solution according to claim 1, wherein the total content of the difluoro ionic complex (1-Cis) stated in the (I) is 0.001 mass % or more and 20 mass % or less relative to the electrolytic solution, and
the total content of the compound stated in the (II) is 0.01 mass % or more and 10 mass % or less relative to the electrolytic solution, and
in a case where the compound stated in the (II) comprises the cyclic sulfonic acid ester, the content of the cyclic sulfonic acid ester is 0.01 mass % or more and 5 mass % or less relative to the electrolytic solution, and
in a case where the compound stated in the (II) comprises the cyclic sulfonic acid ester having an unsaturated bond, the content of the cyclic sulfonic acid ester having an unsaturated bond is 0.01 mass % or more and 3 mass % or less relative to the electrolytic solution, and
in a case where the compound stated in the (II) comprises the cyclic sulfuric acid ester, the content of the cyclic sulfuric acid ester is 0.01 mass % or more and 5 mass % or less relative to the electrolytic solution, and
in a case where the compound stated in the (II) comprises the cyclic disulfonic acid ester, the content of the cyclic disulfonic acid ester is 0.01 mass % or more and 5 mass % or less relative to the electrolytic solution, and
in a case where the compound stated in the (II) comprises the chain disulfonic acid ester, the content of the chain disulfonic acid ester is 0.01 mass % or more and 5 mass % or less relative to the electrolytic solution, and
in a case where the compound stated in the (II) comprises the cyclic disulfonic acid anhydride, the content of the cyclic disulfonic acid anhydride is 0.01 mass % or more and 3 mass % or less relative to the electrolytic solution, and
in a case where the compound stated in the (II) comprises the nitrile group-containing compound, the content of the nitrile group-containing compound is 0.01 mass % or more and 5 mass % or less relative to the electrolytic solution, and
in a case where the compound stated in the (II) comprises the silyl phosphate ester derivative, the content of the silyl phosphate ester derivative is 0.01 mass % or more and 5 mass % or less relative to the electrolytic solution, and
in a case where the compound stated in the (II) comprises the silyl borate ester derivative, the content of the silyl borate ester derivative is 0.01 mass % or more and 5 mass % or less relative to the electrolytic solution.

6. The electrolytic solution according to claim 1, wherein the difluoro ionic complex (1) further comprises (III) a difluoro ionic complex (1-Trans) in a trans conformation represented by the general formula (1-Trans):

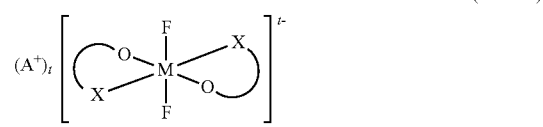

(1-Trans)

wherein in (1-Trans)

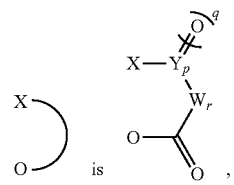

is wherein in the general formula (1-Trans),
$A^+$ is any one selected from the group consisting of a metal ion, a proton, and an onium ion, and M is any one selected from the group consisting of Si, P, As, and Sb;
F is a fluorine atom; 0 is an oxygen atom; t is 2 when M is Si, and t is 1 when M is P, As, or Sb;
X is an oxygen atom or —N(R$^1$)—; N is a nitrogen atom; and R$^1$ is a hydrocarbon group having 1 to 10 carbon atoms and optionally having a hetero atom and/or a halogen atom (the hydrocarbon group optionally having a branched-chain or ring structure when the number of carbon atoms is 3 or more); when X is —N(R$^1$)—, and p is 0, X and W are bonded directly and optionally form any one or more structures selected from the general formulas (1-Trans-1) to (1-Trans-3) below; in the case of the general formula (1-Trans-2) below where the direct bond is a double bond, R$^1$ is not present,
Y is a carbon atom or a sulfur atom; q is 1 when Y is a carbon atom; q is 1 or 2 when Y is a sulfur atom;
W represents a hydrocarbon group having 1 to 10 carbon atoms and optionally having a hetero atom and/or a halogen atom (the hydrocarbon group optionally having a branched-chain or ring structure when the number of carbon atoms is 3 or more), or —N($R^2$)—; wherein $R^2$ represents a hydrogen atom, an alkaline metal, or a hydrocarbon group having 1 to 10 carbon atoms and optionally having a hetero atom and/or a halogen atom; when the number of carbon atoms is 3 or more, $R^2$ optionally has a branched-chain or ring structure; p is 0 or 1, q is an integer of 0 to 2, r is an integer of 0 to 2, and further, p+r≥1:

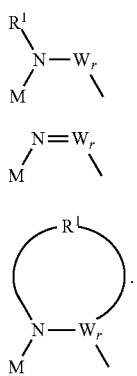

(1-Trans-1)

(1-Trans-2)

(1-Trans-3)

7. The electrolytic solution according to claim 6, wherein elements in an anion moiety of the difluoro ionic complex (1-Trans) are at least one combination selected from (Trans-a), (Trans-b), (Trans-c), and (Trans-d):

(Trans-a) M=P; X=O; Y=C; p, q, and t=1; and r=0,
(Trans-b) M=P; X=O; W=C($CF_3$)$_2$; p and q=0; and r and t=1,
(Trans-c) M=Si; X=O; Y=C; p and q=1; t=2; and r=0, and
(Trans-d) M=P; X=N($R^1$); Y=C; $R^1$=$CH_3$; p, q, and t=1; and r=0.

8. The electrolytic solution according to claim 6, wherein the $A^+$ in the difluoro ionic complex (1-Trans) comprises one or more selected from the group consisting of a lithium ion, a sodium ion, a potassium ion, and a quaternary alkylammonium ion.

9. The electrolytic solution according to claim 6, wherein the mass ratio (1-Trans)/(1-Cis) of the difluoro ionic complex (1-Trans) to the difluoro ionic complex (1-Cis) is 0.0001 or more and 0.05 or less.

10. The electrolytic solution according to claim 1, further comprising (IV) a tetrafluoro ionic complex represented by the general formula (1-Tetra):

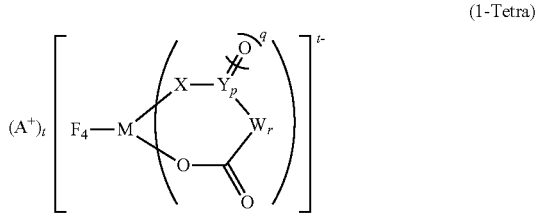

(1-Tetra)

wherein in the general formula (1-Tetra), $A^+$ is any one selected from the group consisting of a metal ion, a proton, and an onium ion, and M is any one selected from the group consisting of Si, P, As, and Sb;
F is a fluorine atom; 0 is an oxygen atom;
t is 2 when M is Si, and t is 1 when M is P, As, or Sb;
X is an oxygen atom or —N($R^1$)—; N is a nitrogen atom; and $R^1$ is a hydrocarbon group having 1 to 10 carbon atoms and optionally having a hetero atom and/or a halogen atom (the hydrocarbon group optionally having a branched-chain or ring structure when the number of carbon atoms is 3 or more);
when X is —N($R^1$)—, and p is 0, X and W are bonded directly and optionally form one or more structures selected from the general formulas (1-Tetra-1) to (1-Tetra-3) below; in the case of the general formula (1-Tetra-2) below where the direct bond is a double bond, $R^1$ is not present,
Y is a carbon atom or a sulfur atom, q is 1 when Y is a carbon atom, q is 1 or 2 when Y is a sulfur atom; W represents a hydrocarbon group having 1 to 10 carbon atoms and optionally having a hetero atom and/or a halogen atom (the hydrocarbon group optionally having a branched-chain or ring structure when the number of carbon atoms is 3 or more), or —N($R^2$)—; wherein $R^2$ represents a hydrogen atom, an alkaline metal, or a hydrocarbon group having 1 to 10 carbon atoms and optionally having a hetero atom and/or a halogen atom; when the number of carbon atoms is 3 or more, $R^2$ optionally has a branched-chain or ring structure;
p is 0 or 1, q is an integer of 0 to 2, r is an integer of 0 to 2, and further, p+r≥1:

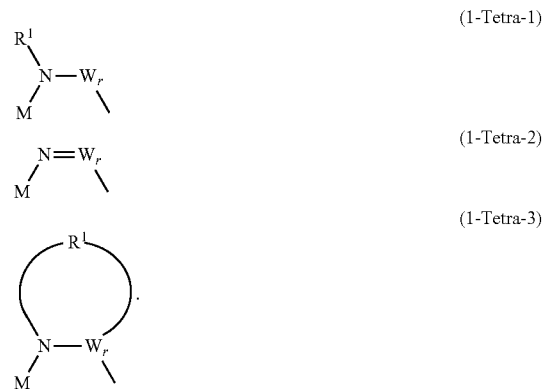

(1-Tetra-1)

(1-Tetra-2)

(1-Tetra-3)

11. The electrolytic solution according to claim 10, wherein elements in an anion moiety of the tetrafluoro ionic complex (1-Tetra) are at least one combination selected from (Tetra-a), (Tetra-b), (Tetra-c), and (Tetra-d):

(Tetra-a) M=P; X=O; Y=C; p, q, and t=1; and r=0,
(Tetra-b) M=P; X=O; W=C($CF_3$)$_2$; p and q=0; and r and t=1,
(Tetra-c) M=Si; X=O; Y=C; p and q=1; t=2; and r=0, and
(Tetra-d) M=P; X=N($R^1$); Y=C; $R^1$=$CH_3$; p, q, and t=1; and r=0.

12. The electrolytic solution according to claim 10, wherein the $A^+$ in the tetrafluoro ionic complex comprises one or more selected from the group consisting of a lithium ion, a sodium ion, a potassium ion, and a quaternary alkylammonium ion.

13. The electrolytic solution according to claim 10, wherein the mass ratio (1-Tetra)/(1-Cis) of the tetrafluoro ionic complex (1-Tetra) to the difluoro ionic complex (1-Cis) is 0.02 or more and 0.25 or less.

14. The electrolytic solution according to claim 1, wherein the nonaqueous solvent comprises at least one selected from the group consisting of a cyclic carbonate and a chain carbonate.

15. A nonaqueous electrolytic solution secondary battery comprising the electrolytic solution according to claim 1, a positive electrode, a negative electrode, and a separator.

16. A nonaqueous electrolytic solution secondary battery, comprising: (a) the electrolytic solution according to claim 1;
- (b) a positive electrode including at least one oxide and/or a polyanion compound as a positive-electrode active material;
- (c) a negative electrode including a negative-electrode active material; and
- (d) a separator including polyolefin or cellulose as a main component, wherein the positive-electrode active material is at least one selected from the group consisting of (A) a lithium-transition metal composite oxide containing at least one metal of nickel, manganese, and cobalt, and having a layered structure, (B) a lithium-manganese composite oxide having a spinel structure, (C) a lithium-containing olivine-type phosphate salt, and (D) a lithium-rich layered transition-metal oxide having a stratified rock-salt structure, and the negative-electrode active material is at least one selected from the group consisting of (E) a carbon material having a d value in a lattice plane (002) of 0.340 nm or less as determined by X ray diffraction, (F) a carbon material having a d value in the lattice plane (002) of more than 0.340 nm as determined by X ray diffraction, (G) an oxide of one or more metals selected from Si, Sn, and Al, (H) one or more metals selected from Si, Sn, and Al or an alloy comprising the one or more metals, or an alloy of lithium and the one or more metals or the alloy, and (I) a lithium titanium oxide.

* * * * *